US012036190B2

(12) United States Patent
Kishnani et al.

(10) Patent No.: US 12,036,190 B2
(45) Date of Patent: Jul. 16, 2024

(54) METHODS AND COMPOSITIONS FOR THE TREATMENT OF CYTOPLASMIC GLYCOGEN STORAGE DISORDERS

(71) Applicant: Duke University, Durham, NC (US)

(72) Inventors: Priya Kishnani, Durham, NC (US); Baodong Sun, Durham, NC (US); Dwight D. Koeberl, Durham, NC (US)

(73) Assignee: Duke University, Durham, NC (US)

( * ) Notice: Subject to any disclaimer, the term of this patent is extended or adjusted under 35 U.S.C. 154(b) by 127 days.

(21) Appl. No.: 17/408,397

(22) Filed: Aug. 21, 2021

(65) Prior Publication Data

US 2022/0040126 A1 Feb. 10, 2022

Related U.S. Application Data

(60) Continuation of application No. 17/190,018, filed on Mar. 2, 2021, now Pat. No. 11,690,812, which is a (Continued)

(30) Foreign Application Priority Data

Aug. 31, 2016 (WO) ................ PCT/US2016/049680

(51) Int. Cl.
*A61K 38/47* (2006.01)
*A61K 31/05* (2006.01)
*A61K 31/12* (2006.01)
*A61K 31/137* (2006.01)
*A61K 31/155* (2006.01)
*A61K 31/167* (2006.01)
*A61K 31/192* (2006.01)
*A61K 31/198* (2006.01)
*A61K 31/216* (2006.01)
*A61K 31/277* (2006.01)
*A61K 31/352* (2006.01)
*A61K 31/355* (2006.01)
*A61K 31/385* (2006.01)
*A61K 31/436* (2006.01)
*A61K 31/519* (2006.01)
(Continued)

(52) U.S. Cl.
CPC ............ *A61K 31/137* (2013.01); *A61K 31/05* (2013.01); *A61K 31/12* (2013.01); *A61K 31/155* (2013.01); *A61K 31/167* (2013.01); *A61K 31/192* (2013.01); *A61K 31/198* (2013.01); *A61K 31/216* (2013.01); *A61K 31/277* (2013.01); *A61K 31/352* (2013.01); *A61K 31/355* (2013.01); *A61K 31/385* (2013.01); *A61K 31/436* (2013.01); *A61K 31/519* (2013.01); *A61K 31/522* (2013.01); *A61K 31/5415* (2013.01); *A61K 31/55* (2013.01); *A61K 31/575* (2013.01); *A61K 31/7016* (2013.01); *A61K 33/00* (2013.01); *A61K 38/465* (2013.01); *A61K 38/47* (2013.01); *A61P 3/00* (2018.01); *C12Y 301/04012* (2013.01); *C12Y 302/0102* (2013.01); *C12Y 302/01022* (2013.01); *C12Y 302/01045* (2013.01); *C12Y 302/01049* (2013.01); *C12Y 302/01076* (2013.01)

(58) Field of Classification Search
CPC .... A61K 31/137; A61K 31/05; A61K 31/155; A61K 31/192; A61K 31/277; A61K 31/355; A61K 31/436; A61K 31/385; A61K 3/519; A61K 31/5415; A61K 31/55; A61K 33/00; A61K 38/47; A61K 38/465; C12Y 302/01; C12Y 302/0102
See application file for complete search history.

(56) References Cited

U.S. PATENT DOCUMENTS 5,236,838 A 8/1993 Rasmussen et al.
5,382,524 A 1/1995 Desnick et al.
(Continued)

FOREIGN PATENT DOCUMENTS

WO 9310244 A1 5/1993
WO 0012740 A2 3/2000
(Continued)

OTHER PUBLICATIONS

Koeberl et al., Molecular Genetics and Metabolism, 2012, vol. 105, p. 221-227. (Year: 2012).*

(Continued)

*Primary Examiner* — Kade Ariani
(74) *Attorney, Agent, or Firm* — POLSINELLI PC

(57) ABSTRACT

The present disclosure is directed to methods of treating a steatosis-associated disorder and methods of treating a cytoplasmic glycogen storage disorder, including glycogen storage disease I, glycogen storage disease III, glycogen storage disease IV, and/or conditions associated with a PRKAG2 mutation, by administering a therapeutic agent selected from a lysosomal enzyme, an autophagy-inducing agent, or a combination thereof. Steatosis-associated disorders discussed herein include GSD Ia, GSD Ib, GSD Ic, NAFLD, and NASH. Other embodiments are directed to methods of reversing steatosis, modulating autophagy, inducing autophagy, and reversing glycogen storage. Methods of treating a cytoplasmic glycogen storage disorder by administering a lysosomal enzyme and a second therapeutic agent are also described. Other embodiments are directed to methods of treating a cytoplasmic glycogen storage disorder by administering a therapeutic agent as an adjunctive therapy to lysosomal enzyme replacement therapy.

14 Claims, 38 Drawing Sheets

Related U.S. Application Data division of application No. 15/760,156, filed as application No. PCT/US2016/052249 on Sep. 16, 2016, now Pat. No. 10,940,125.

(60) Provisional application No. 62/220,701, filed on Sep. 18, 2015.

(51) Int. Cl.

| | |
|---|---|
| A61K 31/522 | (2006.01) |
| A61K 31/5415 | (2006.01) |
| A61K 31/55 | (2006.01) |
| A61K 31/575 | (2006.01) |
| A61K 31/7016 | (2006.01) |
| A61K 33/00 | (2006.01) |
| A61K 38/46 | (2006.01) |
| A61P 3/00 | (2006.01) |

(56) References Cited

U.S. PATENT DOCUMENTS

| | | | |
|---|---|---|---|
| 5,401,650 | A | 3/1995 | Desnick et al. |
| 5,686,240 | A | 11/1997 | Schuchman et al. |
| 5,879,680 | A | 3/1999 | Ginns et al. |
| 7,056,712 | B2 | 6/2006 | Chen |
| 10,940,125 | B2 | 3/2021 | Koeberl et al. |
| 2002/0110551 | A1 | 8/2002 | Chen |
| 2004/0081645 | A1 | 4/2004 | Van Bree et al. |
| 2006/0069070 | A1 | 3/2006 | Fiorucci et al. |
| 2009/0182022 | A1 | 7/2009 | Rongen et al. |
| 2009/0232879 | A1 | 9/2009 | Cable et al. |
| 2011/0104187 | A1 | 5/2011 | Chen et al. |
| 2012/0082653 | A1 | 4/2012 | Koeberl |
| 2014/0315781 | A1 | 10/2014 | Lee et al. |
| 2018/0326021 | A1 | 11/2018 | Kishnani et al. |
| 2021/0251922 | A1 | 3/2021 | Koeberl et al. |

FOREIGN PATENT DOCUMENTS

| | | | |
|---|---|---|---|
| WO | 2013134530 | A1 | 9/2013 |
| WO | 2014130722 | A1 | 8/2014 |
| WO | 2014130723 | A1 | 8/2014 |
| WO | 2014151950 | A1 | 9/2014 |
| WO | 2015062738 | A1 | 5/2015 |
| WO | 2015157697 | A1 | 10/2015 |

OTHER PUBLICATIONS

Farah B, et al. (2016) Induction of autophagy improves hepatic lipid metabolism in glucose-6-phosphatase deficiency. Journal of Hepatology. 64(2):370-379.
Grygiel-Górniak B, et al. (2014) Peroxisome proliferator-activated receptors and their ligands: nutritional and clinical implications—a review. Nutrition Journal. 13:17.
Jiao M, et al. (2014) Peroxisome proliferator-activated receptor a activation attenuates the inflammatory response to protect the liver from acute failure by promoting the autophagy pathway. Cell Death & Disease. 5:e1397.
Amalfitano A., et al., "Recombinant Human Acid Alpha-glucosidase Enzyme Therapy for Infantile Glycogen Storage Disease Type II: Results of a Phase I/II Clinical Trial," Genet. Med. 2001 3(2):132-138.
Arad et al., "Constitutively active AMP kinase mutations cause glycogen storage disease mimicking hypertrophic cardiomyopathy," J Clin Invest, 109(3):357-62, Feb. 2002.
Bandsma R.H.J., et al., "Disturbed Lipid Metabolism in Glycogen Storage Disease Type 1," European Journal of Pediatrics, vol. 161, 2002, pp. S65-S69.
Buhrer et al., "Fetal bradycardia at 28 weeks of gestation associated with cardiac glycogen phosphorylase b kinase deficiency," Acta Paediatr, 92(11): 1352-3, Nov. 2003.
Burwinkel et al."Fatal congenital heart glycogenosis caused by a recurrent activating R531Q mutation in the gamma 2-subunit of AMP-activated protein kinase (PRKAG2), not by phosphorylase kinase deficiency," Am J Hum Genet, 76 (6):1034-49, May 2005.
Chou et al., "Glycogen storage disease type I and G6Pase-β deficiency: etiology and therapy", Nat Rev Endocrinol., Dec. 2010, vol. 6, No. 12, pp. 676-688.
Coppola M., et al., "Thyroid Hormone Analogues and Derivatives: Actions in Fatty Liver," World Journal of Hepatology, 2014, vol. 6(3), pp. 114-129.
Extended European Search Report for Application No. EP16842895. 1, mailed Jan. 31, 2019, 9 pages.
Fuller, M. et al., "Isolation and characterisation of a recombinant, precursor form of lysosomal acid alpha-glucosidase," Eur. J. Biochem. 234:903 909 (1995).
Gollob et al., "Novel PRKAG2 mutation responsible for the genetic syndrome of ventricular preexcitation and conduction system disease with childhood onset and absence of cardiac hypertrophy," Circulation, 104(25): 3030-3, Dec. 2001.
International Preliminary Report on Patentability for International Application No. PCT/US2016/049680, mailed Mar. 15, 2018, 7 pages.
International Search Report and Written Opinion for International Application No. PCT/US2016/049680, mailed Nov. 16, 2016, 7 pages.
International Preliminary Report on Patentability for the Application No. PCT/US2016/052249, dated Mar. 29, 2018, Applicant—Duke University, Inventors—Dwight Koeberl, et al., 9 pages.
International Search Report and Written Opinion for PCT/US2016/052249 mailed Dec. 7, 2016, Applicant—Duke University, Inventors—Dwight Koeberl, et al., 10 pages.
Laforet et al. "A new mutation in PRKAG2 gene causing hypertrophic cardiomyopathy with conduction system disease and muscular glycogenosis," Neuromuscul Disord, 16(3):178-82, Mar. 2006.
Lin C., et al., "Pharmacological Promotion of Autophagy Alleviates Steatosis and Injury in Alcoholic and Non-alcoholic Fatty Liver Conditions in Mice," Journal of Hepatology, vol. 58(5), May 2013, pp. 993-999, doi: 10.1016/j.jhep.2013.01.011.
Mendelsohn N.J., et al., "Elimination of Antibodies to Recombinant Enzyme in Pompe's Disease," The New England Journal Medicine, Jan. 8, 2009, vol. 360(2), pp. 194-195.
Ozen et al., "Glycogen storage diseases: New perspectives", World J Gastroenterol., May 14, 2007, vol. 13, No. 18, pp. 2541-2553.
Raben et al: "Enzyme replacement therapy in the mouse model of Pompe disease," Molecular Genetics and Metabolism, vol. 80, No. 1-2,Sep. 1, 2003 (Sep. 1, 2003), pp. 159-169.
Regalado et al., "Infantile hypertrophic cardiomyopathy of glycogenosis type IX: isolated cardiac phosphorylase kinase deficiency," Pediatr Cardiol. Jul.-Aug. 1999; 20(4):304-7.
Rodriguez G.A., et al., "Impaired Autophagic Flux is Associated with Increased Endoplasmic Reticulum Stress during the Development of NAFLD," Cell Death and Disease, vol. 5, 2014, pp. 1-13, e1179.
Silva B.D., et al., "Singular Effects of PPAR Agonists on Nonalcoholic Fatty Liver Disease of Diet-Induced Obese Mice," Life Sciences, 2015, vol. 127, pp. 73-81.
Strothotte et al: "Enzyme replacement 1-15 therapy with alglucosidase alfa in 44 patients with late-onset glycogen storage disease type 2:12-month results of an observational clinical trial",Journal of Neurology—Zeitschrift Fuer Neurologie, vol. 257, No. 1, Aug. 1, 2009 (Aug. 1, 2009), pp. 91-97.
Sun et al., "Alglucosidase alfa enzyme replacement therapy as a therapeutic approach for glycogen storage disease type III", Molecular Genetics and Metabolism, Feb. 2013, vol. 108, No. 2, pp. 145-147.
Van Hove, J. L. K. et al., "High-level production of recombinant human lysosomal acid alpha-glucosidase in Chinese hamster ovary cells which targets to heart muscle and corrects glycogen accumulation in fibroblasts from patients with Pompe disease," Proc. Natl. Acad. Sci. USA 93:65 70 (1996).
Weledji: "Paediatric Metabolic Conditions of the Liver", EMJ Hepatology, Jan. 2015, vol. 3, No. 1, pp. 55-62.

(56) References Cited

OTHER PUBLICATIONS

Wermuth C.G., "Similarity in Drugs: Reflections on Analogue Design," Drug discovery Today, 2006, vol. 11, No. 7/8, pp. 348-354.
Xu et al: "Improved efficacy of gene therapy approaches for Pompe disease using a new, immune-deficient GSD-II mouse model", Gene Therapy, vol. 11, No. 21, Nov. 1, 2004 (Nov. 1, 2004), pp. 1590-1598.
Zhang et al., "Single-nucleotide polymorphisms of the PRKCG gene and osteosarcoma susceptibility," Tumour Bio, 35 (12): 12671-7, Sep. 2014.
Zhang et al. "Overexpression of G100S mutation in PRKAG2 causes Wolff-Parkinson-White syndrome in zebrafish," ClinGenet, 86(3):287-91, Oct. 2013.

* cited by examiner

FIG. 4A
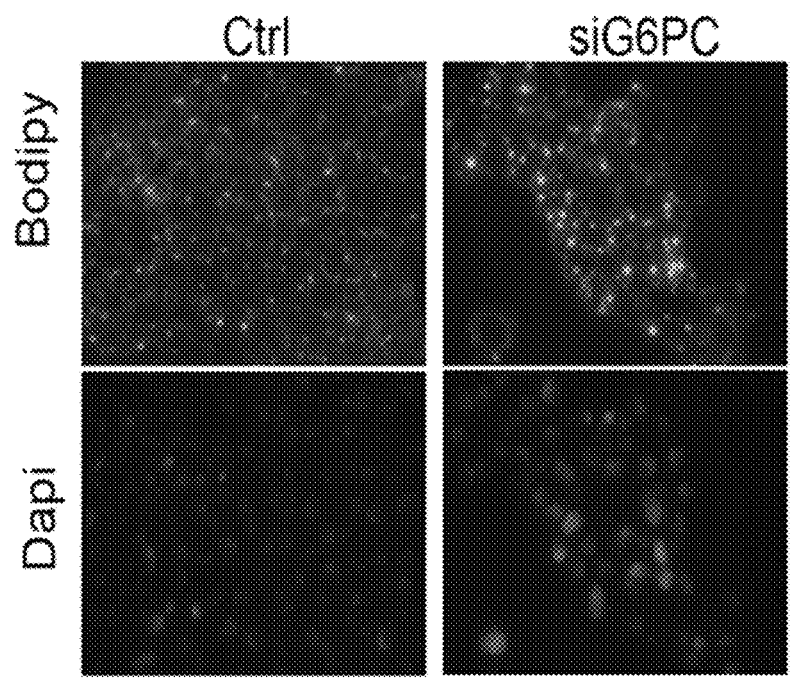
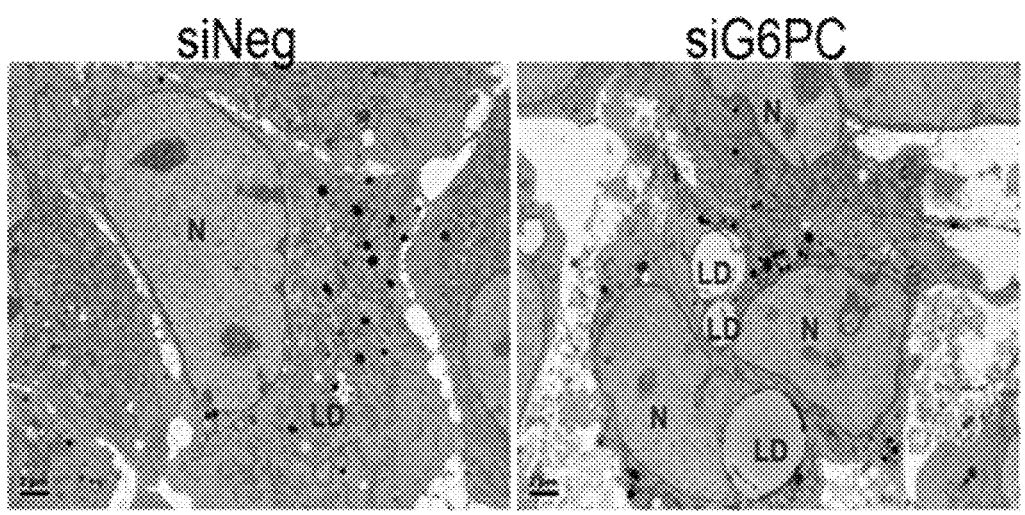
FIG. 4B

FIG. 7A
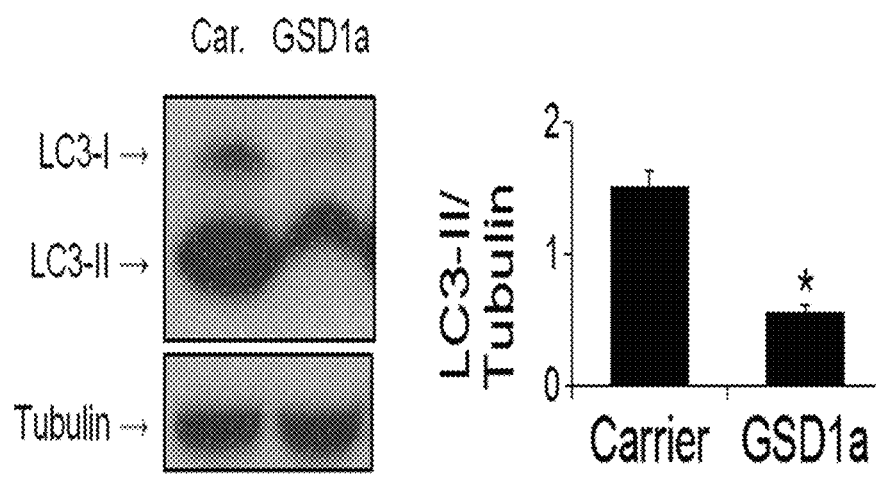
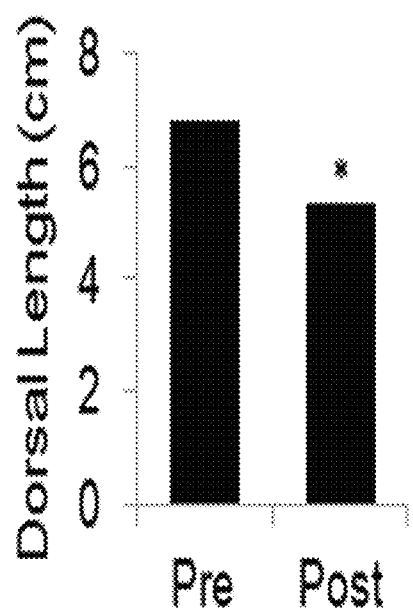
FIG. 7B
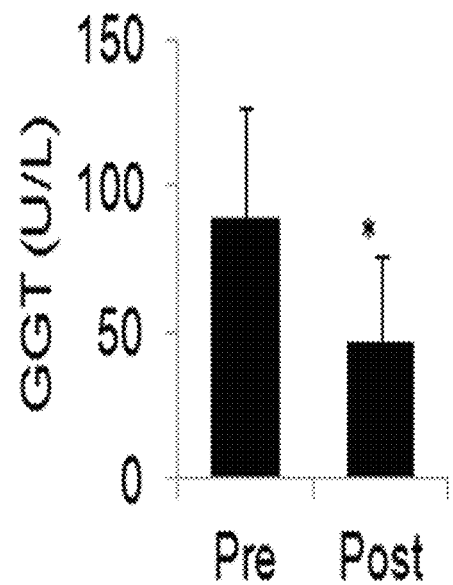
FIG. 7C

FIG. 8A
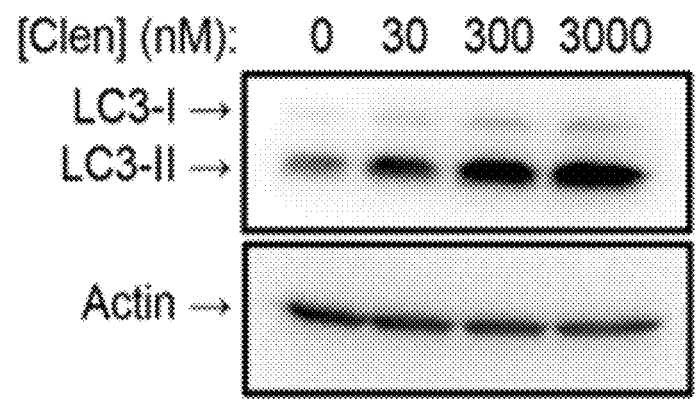
FIG. 8B
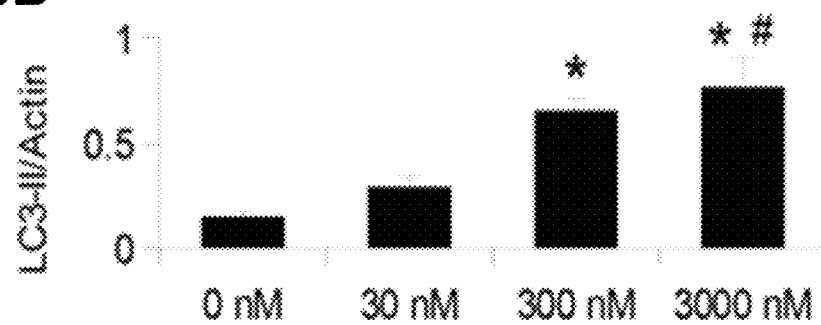
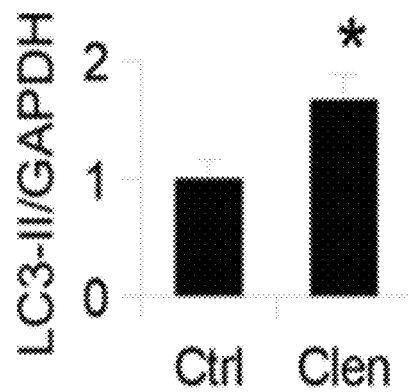
FIG. 8C

FIG. 9A
ERT Depends Upon Mannose-6-phosphate Receptor Targeting
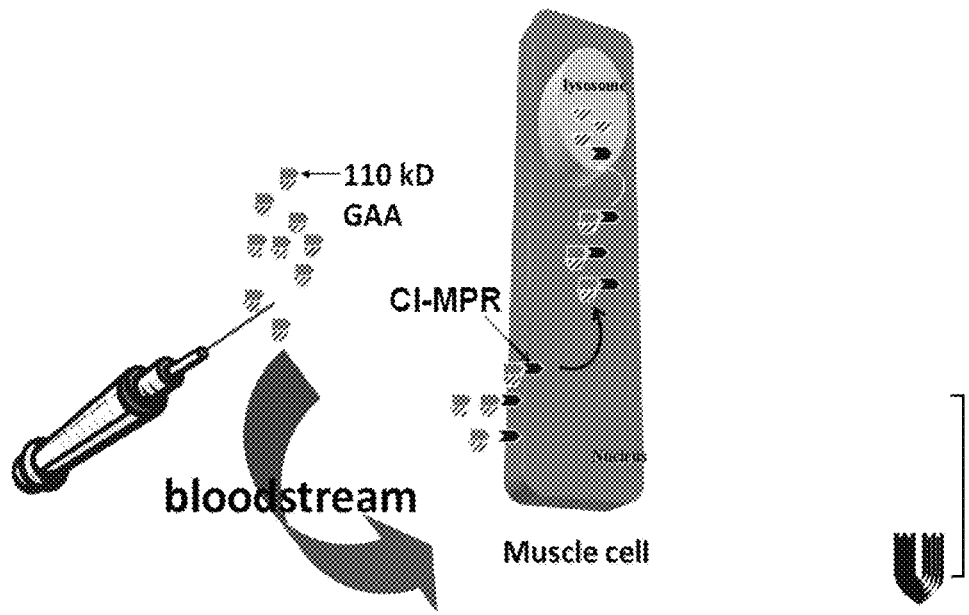
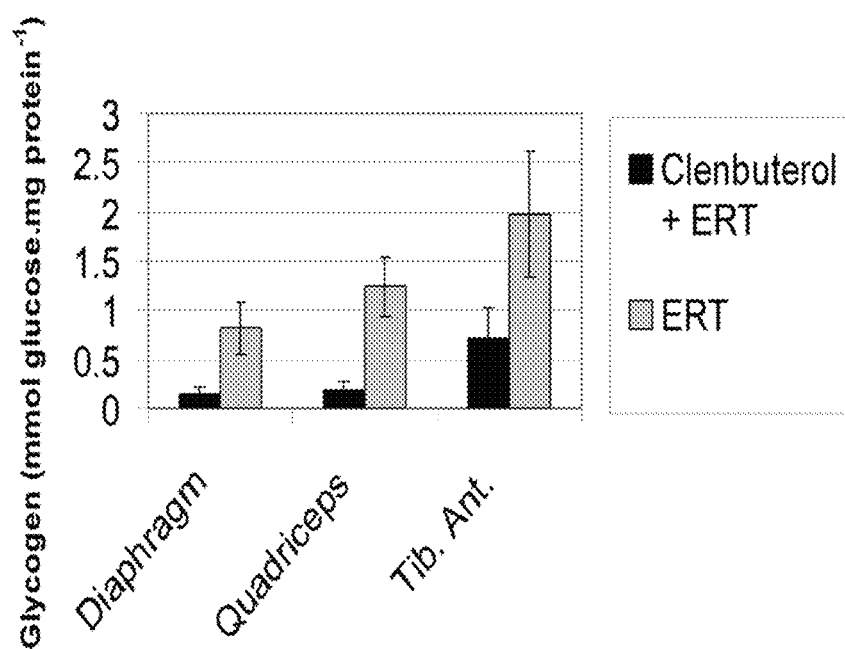
FIG. 9B FIG. 19
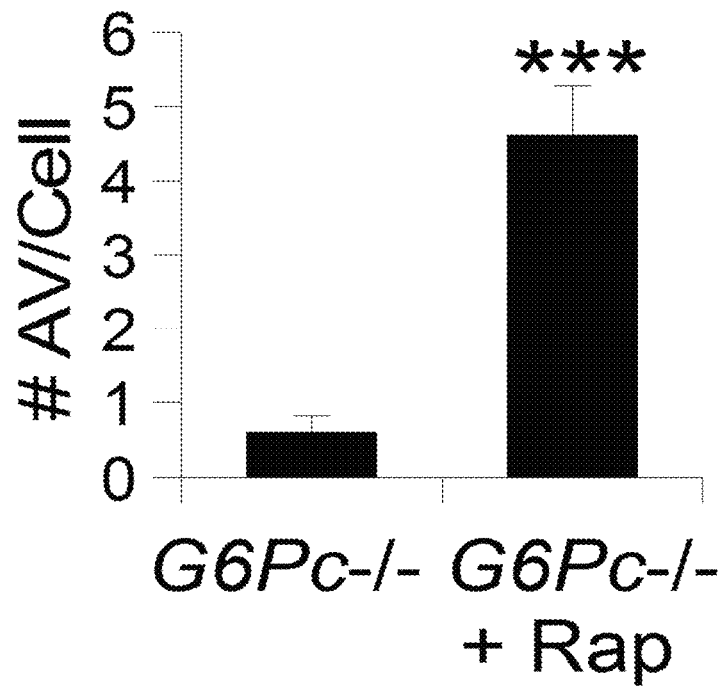
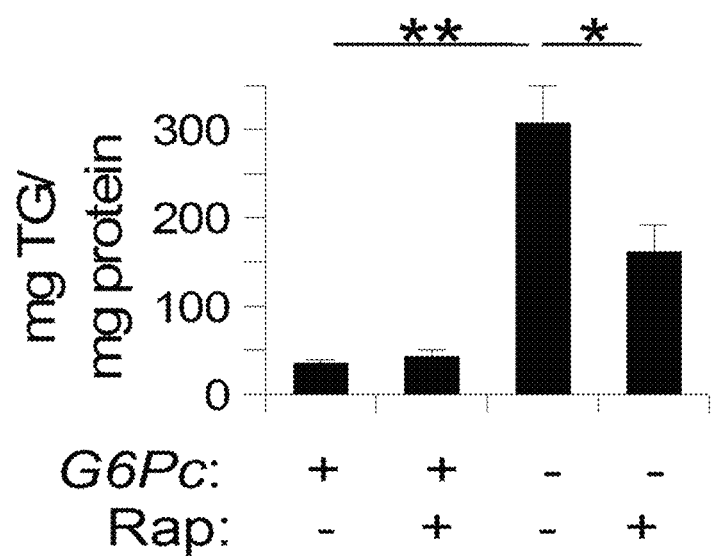
FIG. 20

FIG. 29A
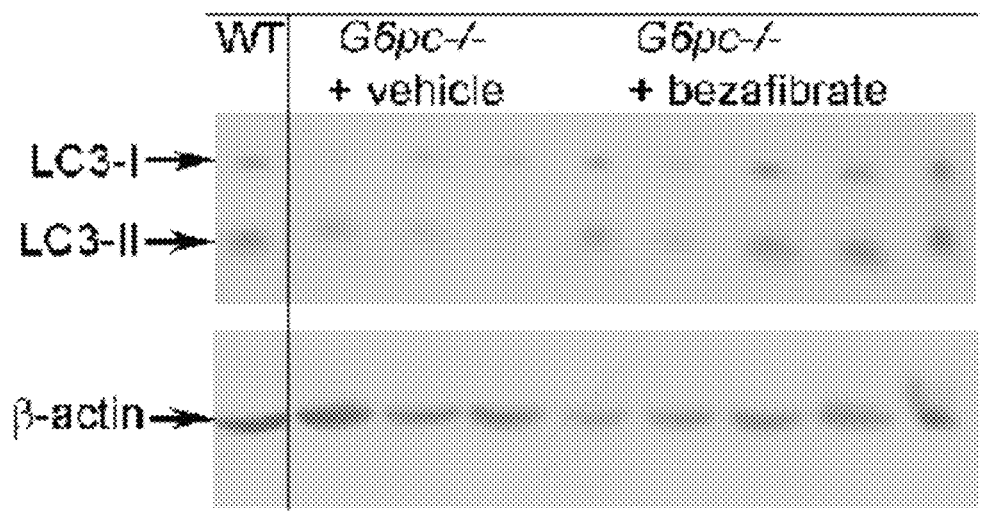
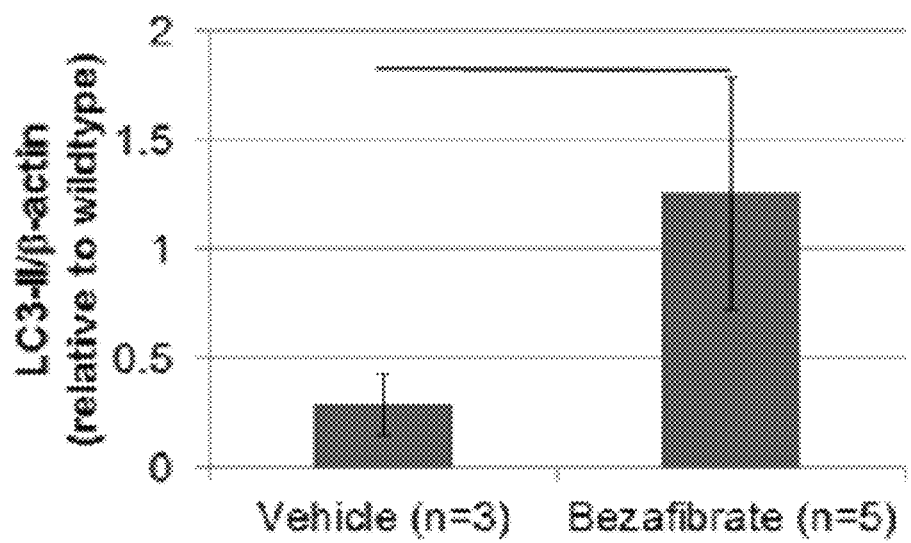
FIG. 29B

FIG. 30A
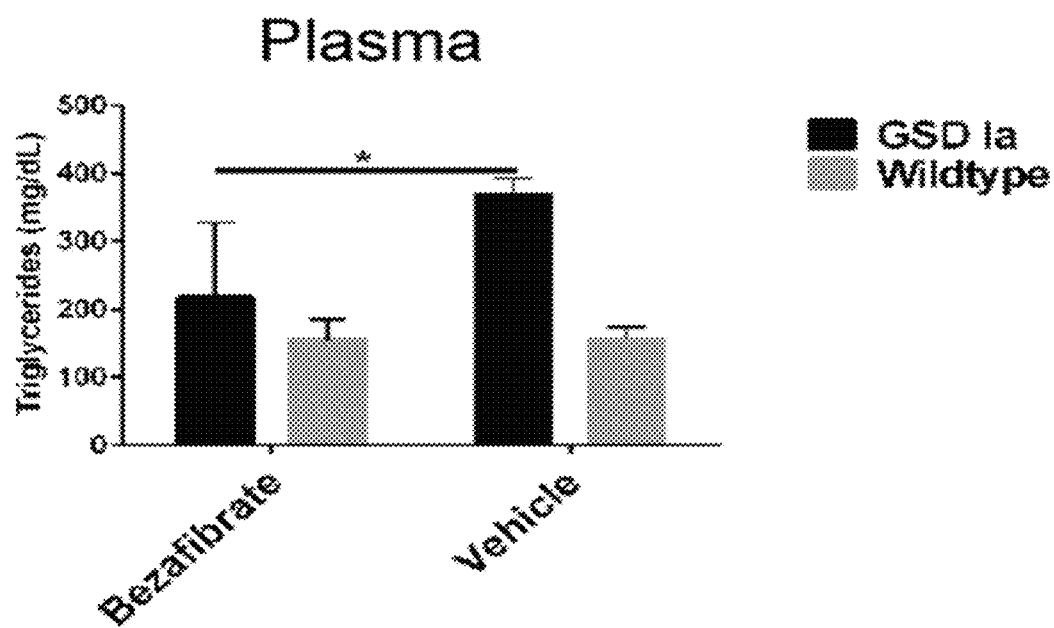
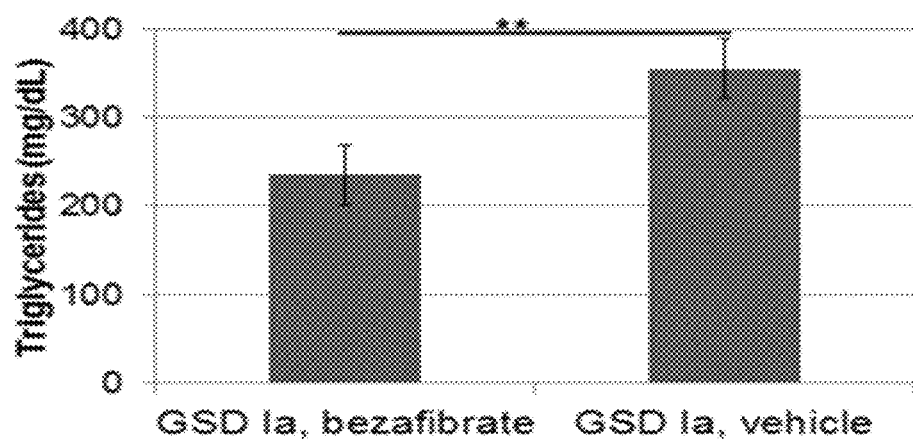
FIG. 30B

FIG. 31A
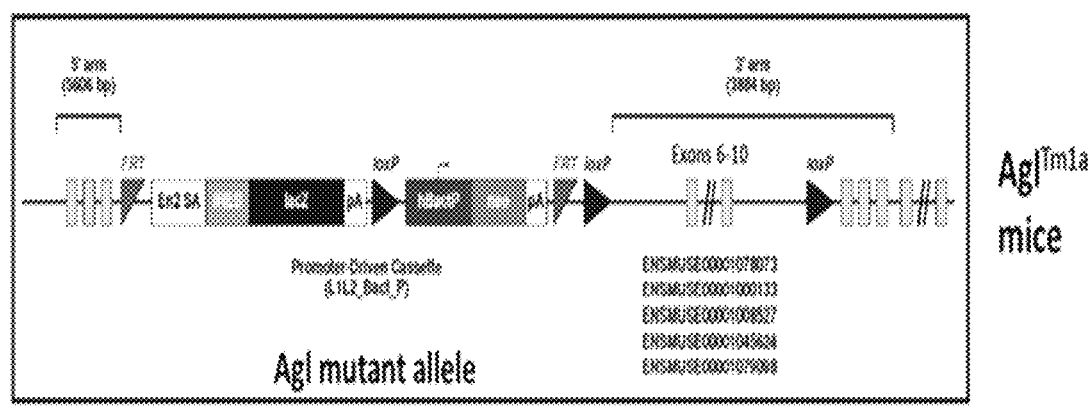
Agl^Tm1a mice
Agl mutant allele
↓ Cre-deleter
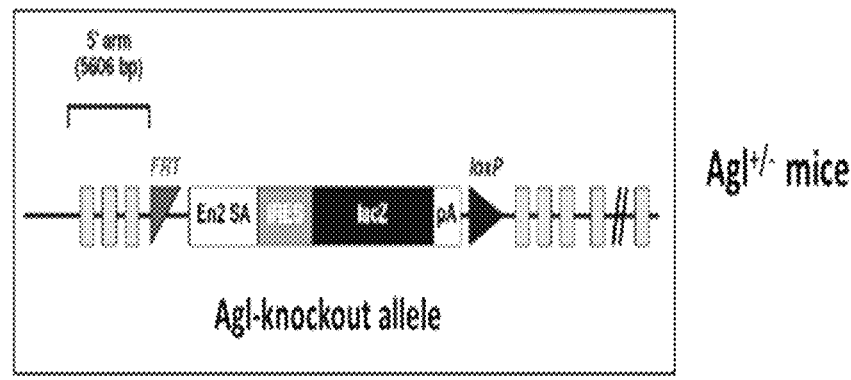
Agl^+/- mice
Agl-knockout allele
FIG. 31B FIG. 33A
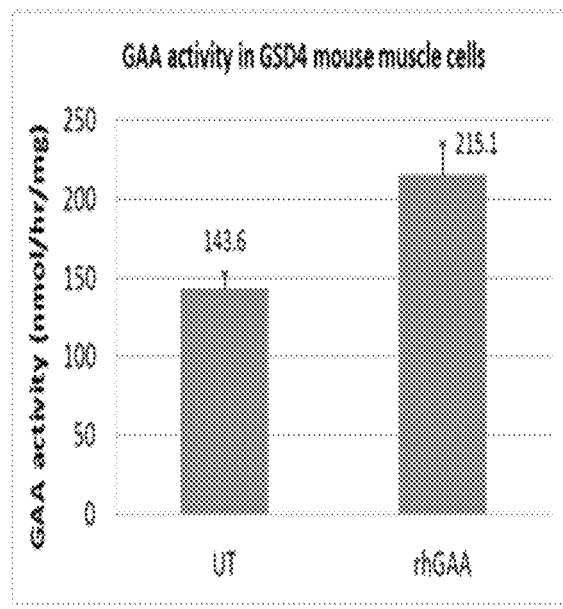
FIG. 33B
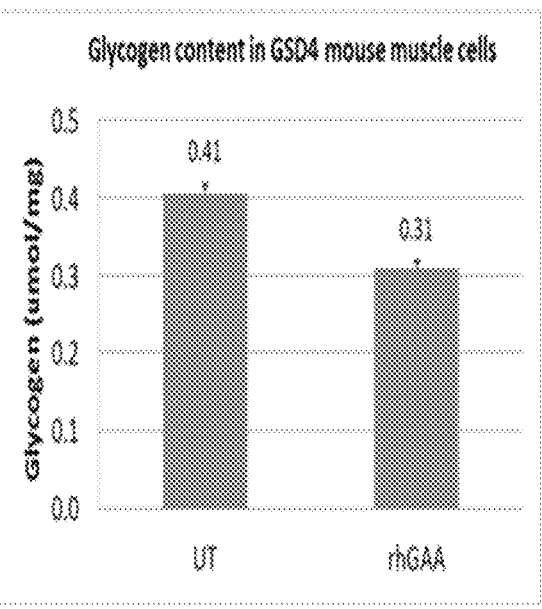
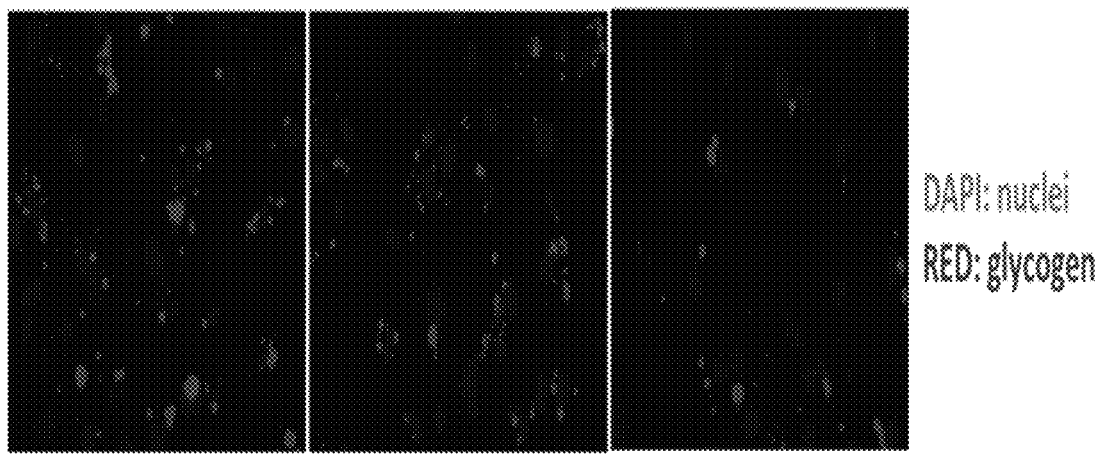
FIG. 34

FIG. 38A
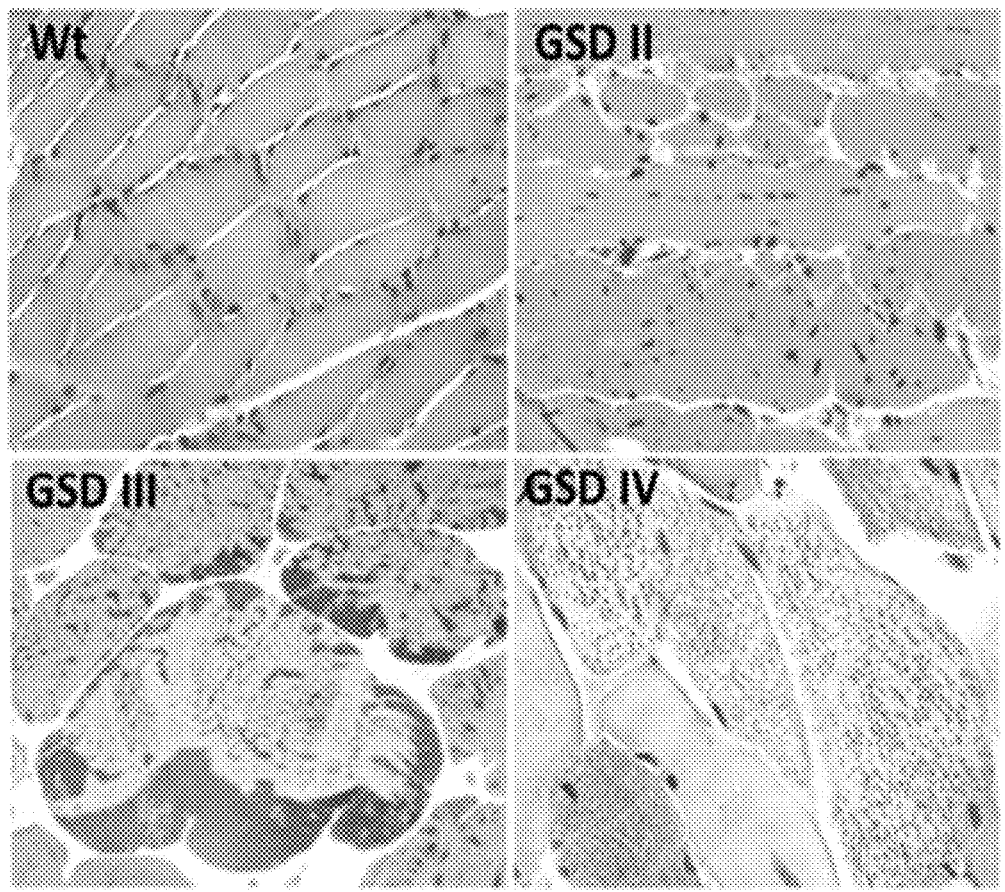
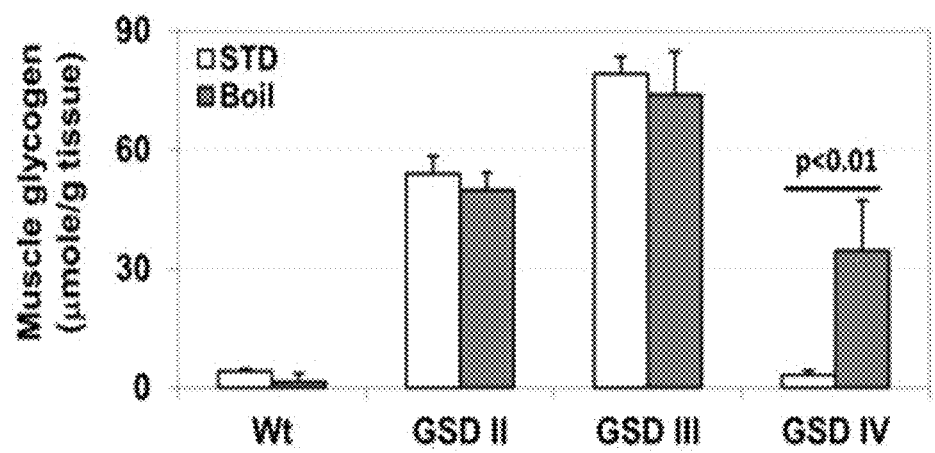
FIG. 38B

FIG. 39A
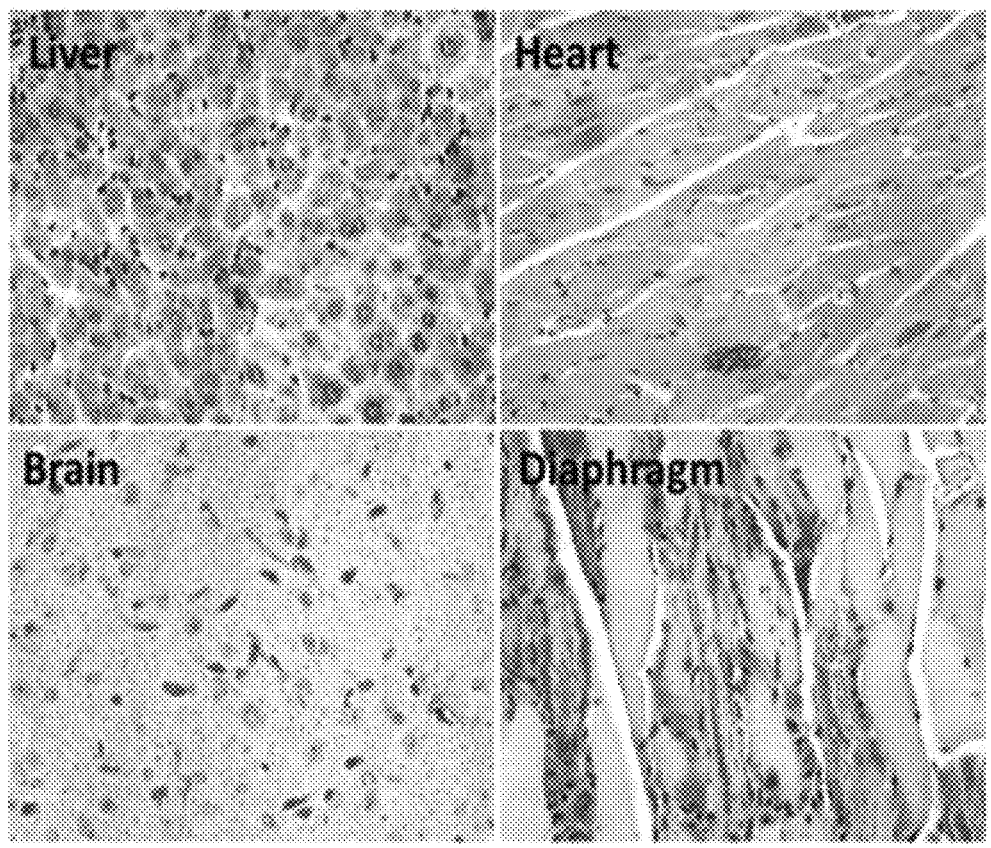
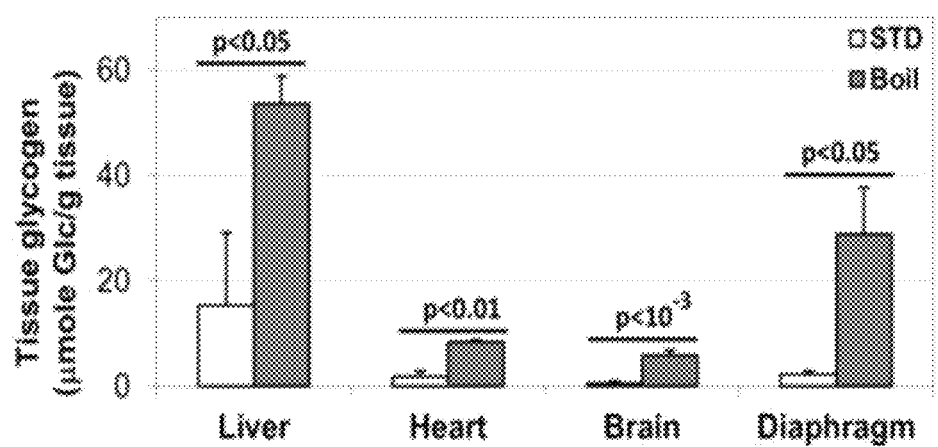
FIG. 39B

FIG. 41A
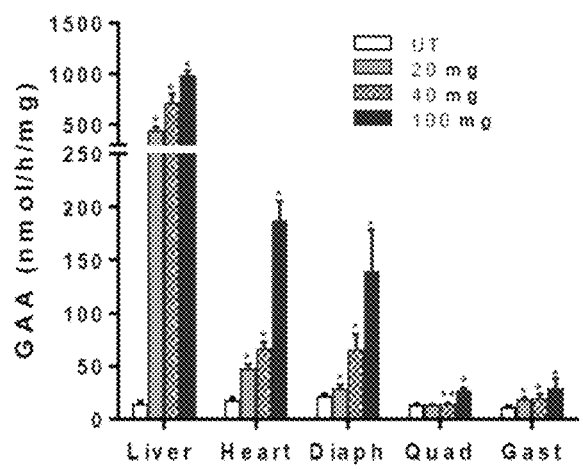
FIG. 41B
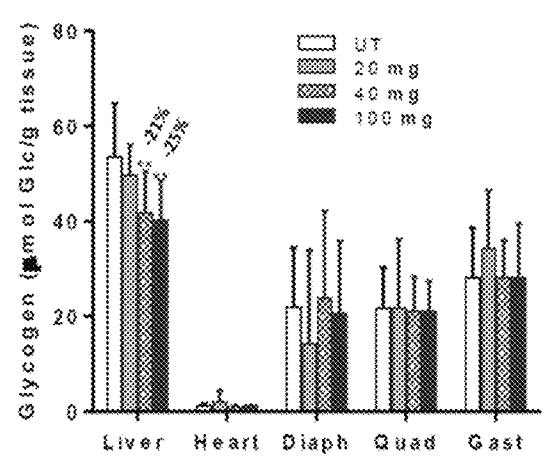
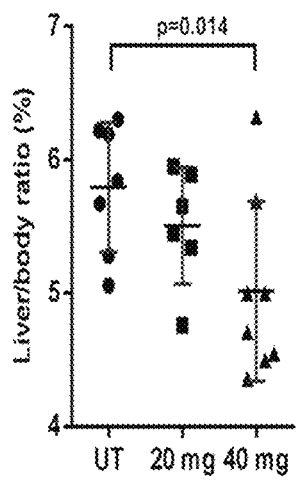
FIG. 41C
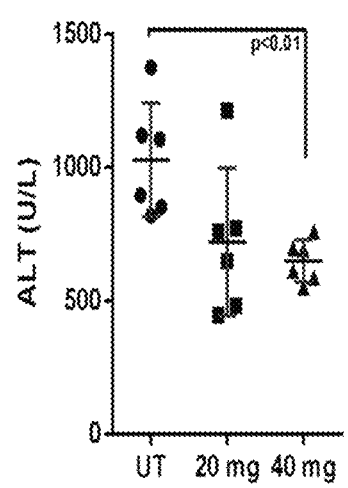
FIG. 41D
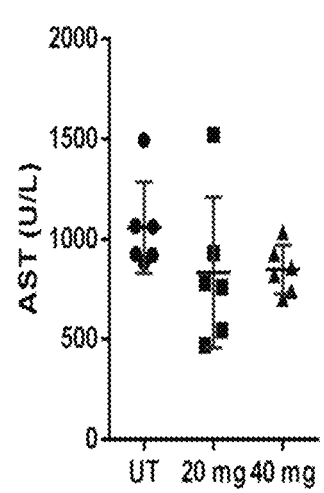
FIG. 41E

FIG. 42A
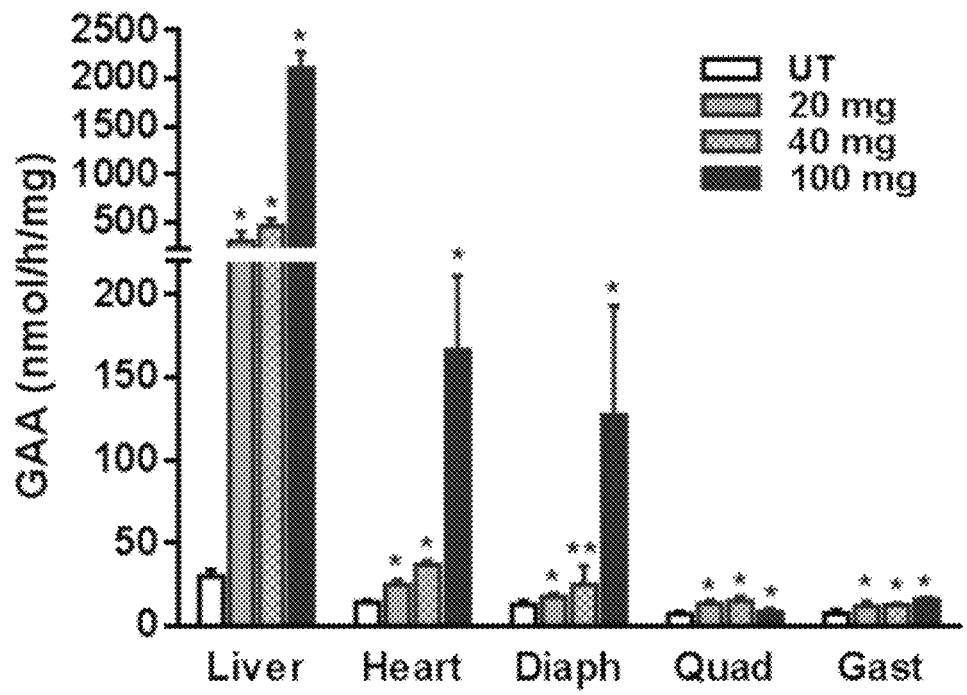
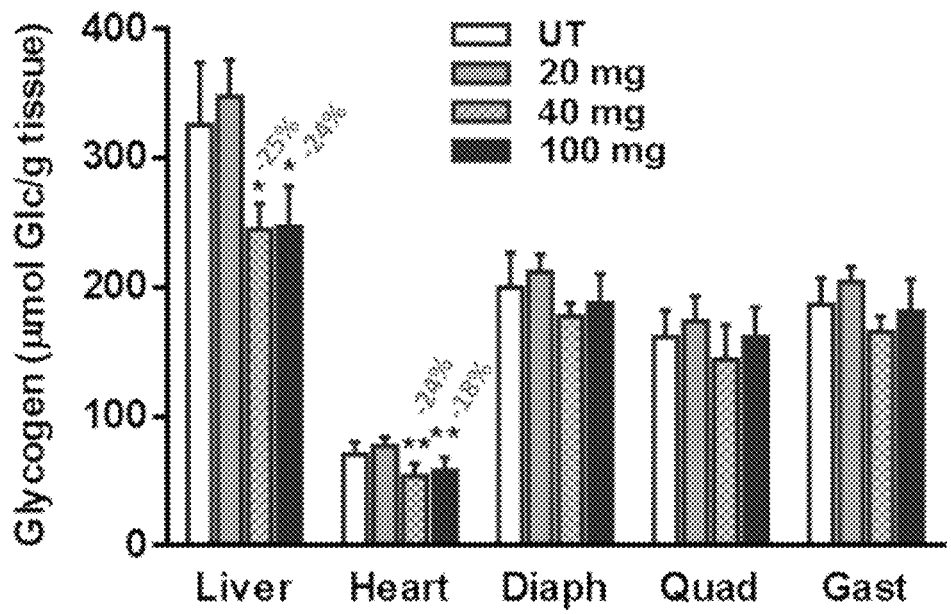
FIG. 42B

METHODS AND COMPOSITIONS FOR THE TREATMENT OF CYTOPLASMIC GLYCOGEN STORAGE DISORDERS

CROSS-REFERENCE TO RELATED APPLICATIONS

This application is a continuation of U.S. application Ser. No. 17/190,018 filed Mar. 2, 2021, which is a divisional application of U.S. application Ser. No. 15/760,156 filed Mar. 14, 2018, which is a U.S. national phase application under 35 U.S.C. § 371 of International Application No. PCT/US2016/052249 filed Sep. 16, 2016, which claims the benefit of priority to both U.S. Provisional Application No. 62/220,701 filed Sep. 18, 2015 and International Application No. PCT/US2016/049680 filed on Aug. 31, 2016, the disclosure of each of which is incorporated by reference herein in its entirety.

SUMMARY

Embodiments herein are directed to treating a steatosis-associated disorder in a subject in need thereof, the method comprising administering to the subject a therapeutic agent of embodiments herein. In some embodiments, the therapeutic agent is an autophagy-inducing agent, a lysosomal enzyme, or a combination thereof. Some embodiments herein are directed to a method of reversing steatosis in a subject in need thereof, the method comprising administering to the subject a therapeutic agent of embodiments herein. Some embodiments herein are directed to a method of reversing glycogen storage in a subject in need thereof, the method comprising administering to the subject a therapeutic agent of embodiments herein. Some embodiments herein are directed to a method of modulating autophagy in a subject in need thereof, the method comprising administering to the subject a therapeutic agent of embodiments herein. Some embodiments herein are directed to a method of inducing autophagy in a subject in need thereof, the method comprising administering to the subject a therapeutic agent of embodiments herein. In some embodiments, the subject has a steatosis-associated disorder.

Some embodiments herein are directed to a method of treating Glycogen Storage Disease Type I (GSD I) to a subject in need thereof, the method comprising administering to the subject a therapeutic agent of embodiments described herein. In some embodiments, the GSD I is selected from GSD Ia, GSD Ib, or GSD Ic. In some embodiments, the GSD I is GSD Ia. Some embodiments herein are directed to a method of treating non-alcoholic fatty liver disease (NAFLD) to a subject in need thereof, the method comprising administering to the subject a therapeutic agent of embodiments described herein. Some embodiments herein are directed to a method of treating non-alcoholic steatohepatitis (NASH) to a subject in need thereof, the method comprising administering to the subject a therapeutic agent of embodiments described herein.

In some embodiments, the therapeutic agent may be a lysosomal enzyme, an autophagy-inducing agent, or a combination thereof. In some embodiments, the above methods may comprise administering a lysosomal enzyme and an autophagy-inducing agent.

In some embodiments, the autophagy-inducing agent may be selected from a thyroid hormone, mTOR inhibitor, caffeine (trimethylxanthine), PPAR-α agonist, AMPK activator, a beta 2 adrenergic agonist (β2 agonist), calcium channel blocker, chemical chaperone, intracellular isositol reducer, Sirtuin-1 activator, sarnesoid X receptor suppressor, or a combination thereof. In some embodiments, the mTOR inhibitor may be selected from rapamycin, Torin1, temsirolimus (CCI-779), everolimus (RAD001), and ridaforolimus (AP-23573), Deforolimus (AP23573, MK-8669), mTORC1/mTORC2 dual inhibitor (e.g. PP242 WYE354), mTOR/P13K dual inhibitor (e.g. PI103 NVP-BEZ235), an analog thereof, or a combination thereof. In some embodiments, the AMPK activator may be selected from 5-Aminoimidazole-4-carboxamide ribonucleotide (AICAR), quercetin, α-lipoic acid, R-lipoic acid, metformin, resveratrol, guanidine, biguanidine, galegine, ginsenoside, curcumin, berberine, epigallocatechin gallate, theaflavin, hispidulin, a salicylate, a prodrug thereof, or a combination thereof. In some embodiments, the PPAR-α agonist may be selected from bezafibrate, genofibrate, ciprofibrate, gemfibrozil, clofibrate, an analog thereof, or a combination thereof. In some embodiments, the thyroid hormone may be selected from thyroxine (T4), triiodothyronine (T3), an analog thereof, or a combination thereof. In some embodiments, the β2 agonist is albuterol, arbutamine, bambuterol, befunolol, bitolterol, bromoacetylalprenololmenthane, broxaterol, carbuterol, cimaterol, cirazoline, clenbuterol, clorprenaline, denopamine, dioxethedrine, dopexamine, ephedrine, epinephrine, etafedrine, ethylnorepinephrine, etilefrine, fenoterol, formoterol, hexoprenaline, higenamine, ibopamine, isoetharine, isoproterenol, isoxsuprine, mabuterol, metaproterenol, methoxyphenamine, norepinephrine, nylidrin, oxyfedrine, pirbuterol, prenalterol, procaterol, propranolol, protokylol, quinterenol, ractopamine, reproterol, rimiterol, ritodrine, salmefamol, soterenol, salmeterol, terbutaline, tretoquinol, tulobuterol, xamoterol, zilpaterol, zinterol, or a combination thereof. In some embodiments, the β2 agonist may be clenbuterol. In some embodiments, the calcium channel blocker may be verapamil. In some embodiments, the chemical chaperone may be trehalose. In some embodiments, the intracellular inositol reducer may be carbamazepine, lithium chloride, or a combination thereof. In some embodiments, the Sirtuin-1 activator may be methylene blue, resveratrol, or a combination thereof. In some embodiments, samesoid X receptor suppressor may be mifepristone. In some embodiments, the autophagy inducing agent is not a B2 agonist. In some embodiments, the autophagy inducing agent induces autophagy. In some embodiments, the β2 agonist induces autophagy.

Some embodiments herein are directed to treating a steatosis-associated disorder, the method comprising administering a β2 agonist to a subject in need thereof. Some embodiments herein are directed to a method of treating GSD I, the method comprising administering a β2 agonist to a subject in need thereof. Some embodiments herein are directed to a method of treating GSD Ia, the method comprising administering a β2 agonist to a subject in need thereof. Some embodiments herein are directed to a method of treating GSD Ib, the method comprising administering a β2 agonist to a subject in need thereof. Some embodiments herein are directed to a method of treating GSD Ic, the method comprising administering a β2 agonist to a subject in need thereof. Some embodiments herein are directed to a method of treating NAFLD, the method comprising administering a β2 agonist to a subject in need thereof. Some embodiments herein are directed to a method of treating NASH, the method comprising administering a β2 agonist to a subject in need thereof.

Embodiments herein are directed to treating a cytoplasmic glycogen storage disorder in an individual comprising administering to the individual a lysosomal enzyme (e.g. an acid alpha-glucosidase (acid α-glucosidase or GAA)). Accordingly, some embodiments of the present disclosure provide for a method of treating a cytoplasmic glycogen storage disorder comprising administering a lysosomal enzyme to an individual in need thereof. In some embodiments, the method further comprises administering a therapeutic agent in addition to the lysosomal enzyme. Some embodiments herein are directed to a method of treating a cytoplasmic glycogen storage disorder in an individual in need thereof comprising administering to the individual a therapeutic agent as an adjunctive therapy to a lysosomal enzyme.

In some embodiments, the therapeutic agent may be selected from a growth hormone, an autocrine glycoprotein, a β2 agonist, an agent to treat or prevent hypoglycemia (e.g. cornstarch), an agent to treat or prevent hyperlipidemia (e.g. HMG-CoA; ACE inhibitors), an agent to treat or prevent neutropenia, an agent to suppress glycogen synthase (e.g. RNAi; 20(S)-protopanaxadiol), an agent to prevent or reverse glycogen synthesis, an agent to treat or prevent fibrosis, an agent to improve mitochondrial function, an agent to treat any other symptom, such as those described herein, of the cytoplasmic storage disorders of embodiments herein, or a combination thereof.

Some embodiments herein are directed to methods of treating a cytoplasmic glycogen storage disorder comprising administering a β2 agonist and an acid α-glucosidase to a subject in need thereof. In some embodiments, the β2 agonist is a selective β2 agonist. In some embodiments, the β2 agonist is albuterol, arbutamine, bambuterol, befunolol, bitolterol, bromoacetylalprenololmenthane, broxaterol, carbuterol, cimaterol, cirazoline, clenbuterol, clorprenaline, denopamine, dioxethedrine, dopexamine, ephedrine, epinephrine, etafedrine, ethylnorepinephrine, etilefrine, fenoterol, formoterol, hexoprenaline, higenamine, ibopamine, isoetharine, isoproterenol, isoxsuprine, mabuterol, metaproterenol, methoxyphenamine, norepinephrine, nylidrin, oxyfedrine, pirbuterol, prenalterol, procaterol, propranolol, protokylol, quinterenol, ractopamine, reproterol, rimiterol, ritodrine, salmefamol, soterenol, salmeterol, terbutaline, tretoquinol, tulobuterol, xamoterol, zilpaterol, zinterol, or a combination thereof. In some embodiments, the β2 agonist may be clenbuterol.

In some embodiments, the lysosomal enzyme may be selected from glucocerebrosidase (for the treatment of Gaucher disease; U.S. Pat. Nos. 5,879,680 and 5,236,838), alpha-glucosidase (acid alpha-glucosidase or GAA) (for the treatment of Pompe disease; PCT International Publication No. WO 00/12740), alpha-galactosidase (e.g., alpha-gal, alpha-galactosidase or alpha-gal) (for the treatment of Fabry Disease; U.S. Pat. No. 5,401,650), alpha-n-acetylgalactosaminidase (for the treatment of Schindler Disease; U.S. Pat. No. 5,382,524), acid sphingomyelinase (for the treatment of Niemann-Pick disease; U.S. Pat. No. 5,686,240), alpha-iduronidase (for the treatment of Hurler, Scheie, or Hurler-Scheie disease; PCT International Publication No. WO 93/10244A1), or a combination thereof. In some embodiments, the lysosomal enzyme may be acid α-glucosidase. In some embodiments, the acid alpha-glucosidase may be selected from a GAA, recombinant human acid alpha-glucosidase (rhGAA), alglucosidase alfa, neorhGAA, reveglucosidase alpha, an rhGAA administered with a chaperone (e.g. 1-deoxynojirimycin (DNJ), α-homonojirimycin, or castanospermine), a chimeric polypeptide comprising any of the foregoing (e.g. a chimeric polypeptide of GAA and a 3E10 anitbody, or GAA tagged with a moiety that promotes transit via an equilibrative nucleoside transporter 2 (ENT2)), a portion thereof, or a combination thereof.

Some embodiments are directed to a composition comprising a therapeutic agent of embodiments herein, and a pharmaceutically acceptable excipient. In some embodiments, the therapeutic agent may be an autophagy-inducing agent, a lysosomal enzyme or a combination thereof. In some embodiments, the composition may include a lysosomal enzyme of embodiments herein and an autophagy-inducing agent of embodiments herein. Some embodiments are directed to a composition comprising an autophagy-inducing agent of embodiments herein, and a pharmaceutically acceptable excipient. Some embodiments are directed to a composition comprising a lysosomal enzyme of embodiments herein, and a pharmaceutically acceptable excipient. Some embodiments are directed to a composition comprising a β2 agonist and an acid alpha-glucosidase. Some embodiments are directed to a method of treating a steatosis-associated disorder comprising administering a composition comprising a therapeutic agent of embodiments herein, and a pharmaceutically acceptable excipient. In some embodiments, the steatosis-associated disorder may be GSD I, NAFLD, NASH, or a combination thereof. In some embodiments, GSD I may be selected from GSD Ia, GSD Ib, or GSD Ic. In some embodiments, GSD I is GSD Ia.

Some embodiments are directed to a method of treating GSD III in an individual in need thereof comprising administering to the individual a composition comprising a β2 agonist and an acid alpha-glucosidase. Some embodiments are directed to a method of treating GSD IV in an individual in need thereof comprising administering to the individual a composition comprising a β2 agonist and an acid alpha-glucosidase.

DESCRIPTION OF THE FIGURES

FIG. 1 illustrates the downregulation of autophagy in the GSD Ia liver.

FIG. 2 illustrates that knockdown of G6Pase in AML12 recapitulates GSDIa.

FIG. 3 illustrates that the loss of G6PC inhibits AMPK and activates mTOR signaling, and restoration of AMPK signaling restores autophagy.

FIG. 4 illustrates lipid accumulation in cells. FIG. 4A illustrates that bodipy staining detected lipids in siG6PC treated cells. FIG. 4B illustrates that electron microscopy detected lipid deposits (LD) in siG6PC treated cells.

FIG. 5 illustrates that mTORC1 inhibition in GSDIa mice induces autophagy and reduces hepatosteatosis and glycogen storage.

FIG. 7 illustrates that rapamycin treatment to induce autophagy reduced liver involvement in canine GSDIa. Dogs (n=4) were treated with AAV-G6Pase. Rapamycin was administered to induce autophagy (1 mg/kg/day for 1 week). FIG. 7A illustrates that LC3-II was reduced in the liver of dogs with GSDIa, in comparison with unaffected carrier dogs. FIG. 7B and FIG. 7C illustrate that liver length (FIG. 7B) and serum GGT (FIG. 7C) were reduced following rapamycin treatment. *=p<0.05.

FIG. 8 illustrates that long acting β-agonist clenbuterol increases autophagosome number in HepG2 cells and in mouse primary hepatocytes. FIG. 8A and FIG. 8B illustrates that clenbuterol increases LC3-II 24 hours after addition in HepG2 cells, at concentrations as low as 300 nM. FIG. 8C illustrates that clenbuterol increases LC3-II 24 hours after ion in mouse primary hepatocytes. Asterisk indicates p<0.05.

FIG. 9 illustrates that ERT depends upon receptor-mediated uptake of recombinant lysosomal enzymes. FIG. 9A illustrates that in lysosomal storage disorders the Cl-MPR is expressed at low levels on the cell membrane, and therefore a drug that increased CI-MPR would enhance biochemical correction from ERT. FIG. 9B illustrates that a selective β-agonist, clenbuterol, increased CI-MPR expression and significantly enhanced biochemical correction in combination with ERT, in comparison with ERT alone, as demonstrated by decreased glycogen storage in mice with a classical lysosomal storage disorder, Pompe disease.

FIG. 10 illustrates loss of G6pc leads to decreased levels of ATG proteins in liver, and decreased levels of autophagosomes in kidney.

FIG. 19 illustrates ultrastructural electron microscope analysis indicates rapamycin-treated GSD Ia mice showed more hepatic autophagic vesicles than untreated mice. Electron microscope images were analyzed for the presence of autophagic vesicles in GSD Ia mouse hepatocytes without or without rapamycin treatment. N=3, and *** indicates p<0.001. Error bars: SEM.

FIG. 20 illustrates rapamycin reduced hepatic triglyceride content in GSD Ia mice. Rapamycin reduced hepatic triglycerides by 50% in GSD Ia mouse livers, which began at 7-fold the levels of wildtype livers. N=4, * indicates p<0.05, and ** indicates p<0.01. Error bars: SEM.

FIG. 24 illustrates treatment of GSD Ia canines with rapamycin reduces hepatic size, and lowers circulating hepatic enzymes.

FIG. 29 illustrates treatment of G6Pc−/− mice with bezafibrate increases autophagosome number in the liver. Bezafibrate was administered by intraperitoneal injection to groups of 5 day old mice, and livers were collected 3 days later. Groups: bezafibrate, n=5; vehicle, n=3. (FIG. 29A) Western blots for LC3-II and β-actin. (FIG. 29B) Quantification of LC3-II (LC3-II/β-actin). Mean +/−SD shown. * indicates p<0.05.

FIG. 30 illustrates treatment of G6Pc−/− mice with bezafibrate reduces plasma triglycerides. Bezafibrate was administered by intraperitoneal injection to groups of 5 day old mice, and triglycerides were quantified 3 days later. (FIG. 30A) plasma, and (FIG. 30B) liver. Groups: bezafibrate, n=5; vehicle, n=3. Mean +/−SD shown. * indicates p<0.05.

FIG. 31 illustrates the generation of heterozygous Agl$^{+/−}$ mice by one-step cross-breeding Agl$^{Tm1a}$ mice (FIG. 31A) with CMV-Cre mice to convert the mutant allele into an Agl-KO allele by deleting the Agl gene Exons 6-10 and the neo expression cassette (FIG. 31B).

FIG. 32 illustrates an analysis of the skeletal muscle biopsies from two GSD IIIa patients, a 45 year old male (Pt. 1) and a 35 year old female (Pt. 2).

FIG. 33 illustrates the (FIG. 33A) GAA activity and (FIG. 33B) glycogen content in primary GSD IV mouse muscle cells with (rhGAA) or without (untreated, UT) rhGAA treatment. rhGAA treatment significantly (p<0.01) reduced glycogen content in these cells. Data were average of two independent experiments ±SD.

FIG. 34 illustrates that rhGAA treatment reduced glycogen deposition in GSD IV mouse myoblasts. Glycogen was stained with an α-glycogen monoclonal antibody (ESG1A9mAb).

FIG. 38 illustrates glycogen content in skeletal muscles from wild-type (Wt) and GSD animals. FIG. 38A illustrates representative PAS staining of muscle (gastrocnemius) sections form Wt mice, GSD II mice, GSD IIIa dogs, and GSD IV mice (magnification 400×). FIG. 38B illustrates comparison of the STD-prep and the Boil-prep methods for quantitation of glycogen in muscles from animals in FIG. 38A. n=5 for mice, n=4 for dogs.

FIG. 39 illustrates measurement of glycogen content in other tissues from the GSD IV mice. FIG. 39A is a PAS staining which shows glycogen deposits of various degrees in liver, diaphragm, heart and brain (cerebrum) of the GSD IV mice (magnification 400×). FIG. 39B is a comparison of the STD-prep and the Boil-prep methods for quantitation of glycogen in these tissues. n=5 mice.

FIG. 41 illustrates (FIG. 41A) rhGAA uptake by tissues of GSD IV mice upon administration of 20 mg/kg, 40 mg/kg, or 100 mg/kg rhGAA; (FIG. 41B) clearance of glycogen accumulation in various tissues upon administration of 20 mg/kg, 40 mg/kg, or 100 mg/kg rhGAA; (FIG. 41C) measure of hepatomegaly (liver/body weight ratio) in GSD IV mice upon administration of 20 mg/kg or 40 mg/kg rhGAA; (FIG. 41D) levels of liver enzyme alanine transaminase (ALT) in GSD IV mice upon administration of 20 mg/kg or 40 mg/kg rhGAA; and (FIG. 41E) levels of liver enzyme aspartate transaminase (AST) in GSD IV mice upon administration of 20 mg/kg or 40 mg/kg rhGAA. rhGAA at indicated doses was intravenously injected into GSD IV mice once per weeks for 4 weeks.

FIG. 42 illustrates (FIG. 42A) enzyme uptake; and (FIG. 42B) clearance of glycogen in tissues of GSD III mice upon weekly intravenous administration of 20 mg/kg, 40 mg/kg, or 100 mg/kg rhGAA for 4 weeks.

DETAILED DESCRIPTION

Figure 1A:
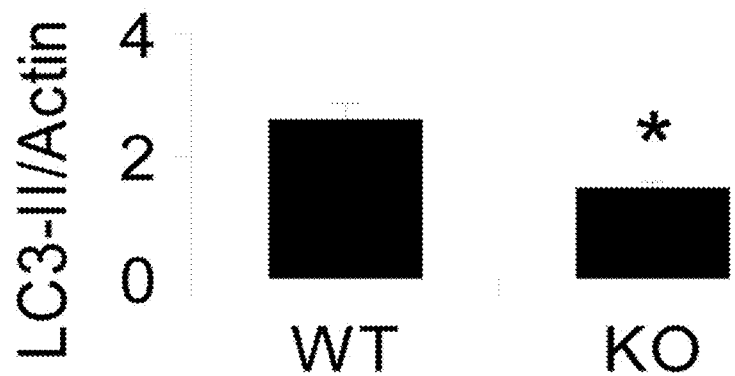
FIG. 1A illustrates decreased LC3-II/Actin ratio, which indicates downregulation of autophagy.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

The present disclosure is directed to inducing autophagy in a subject having a steatosis-associated disorder, such as GSD I, NASH, or NAFLD, and reversing glycogen storage and steatosis in the subject. In some embodiments, GSD I may be selected from GSD Ia, GSD Ib, or GSD Ic. In some embodiments, the GSD I is GSD Ia. Accordingly, embodiments of the present disclosure are directed to methods of treating a steatosis-associated disorder comprising administering a therapeutic agent to a subject in need thereof. In some embodiments, the therapeutic agent is an autophagy-inducing agent.

It must also be noted that as used herein and in the appended claims, the singular forms "a", "an", and "the" include plural reference unless the context clearly dictates otherwise. Thus, for example, reference to a "02 agonist" is a reference to one or more β2 agonists and equivalents thereof known to those skilled in the art, and so forth.

As used herein, the term "about" means plus or minus 5% of the numerical value of the number with which it is being used. Therefore, about 50% means in the range of 45%-55%.

"Adjuvant" or "adjunctive" therapy, as used herein, refers to therapy that is given in addition to the primary, main, or initial therapy to maximize its effectiveness. For example, in some embodiments, herein a therapeutic agent, such as a β2 agonist, may be administered as an adjunctive therapy to a lysosomal enzyme, such as GAA, in order to increase uptake of the lysosomal enzyme. In some embodiments, the adjunctive therapy may be co-administered or sequentially administered.

"Administering", when used in conjunction with a therapeutic, means to administer a therapeutic directly into or onto a target tissue or to administer a therapeutic to a subject, whereby the therapeutic positively impacts the tissue to which it is targeted. Thus, as used herein, the term "administering", when used in conjunction with a therapeutic, can include, but is not limited to, providing a therapeutic to a subject systemically by, for example, intravenous injection, whereby the therapeutic reaches the target tissue. Administering a composition or therapeutic may be accomplished by, for example, injection, oral administration, topical administration, or by these methods in combination with other known techniques. Such combination techniques may include heating, radiation, ultrasound and the use of delivery agents. Preferably, administering is a self-administration, wherein the therapeutic or composition is administered by the subject themselves. Alternatively, administering may be administration to the subject by a health care provider.

The terms, "treat" and "treatment," as used herein, refer to amelioration of one or more symptoms associated with the disease, prevention or delay of the onset of one or more symptoms of the disease, and/or lessening of the severity or frequency of one or more symptoms of the disease. For example, treatment can refer to of the individual affected by the disease, or any combination of these effects. For example, treatment can refer to improvement of hypoglycemia, growth retardation, hepatomegaly, and hepatic function (e.g., reduction of SGOT, SGPT); cardiac status (e.g., reduction, amelioration or prevention of the progressive cardiomyopathy, arrhythmia and other cardiac manifestations that can be found, for example, in GSD-III), myopathy (e.g., exercise tolerance), reduction of glycogen levels in tissue (e.g., liver and muscle) of the individual affected by the disease, or any combination of these effects. Further, the treatment may prevent long term complications such as chronic liver disease, metabolic syndrome, cirrhosis, and fibrosis as well as hepatocellular carcinoma due to clearance of glycogen with an abnormal structure, atherosclerosis secondary to hyperlipidemia, ventricular hypertrophy, and reduced bone mineral density. In some embodiments, treatment includes improvement of liver symptoms, particularly, in reduction or prevention of GSD (e.g., GSD-Ia)-associated hepatosteatosis, abdominal discomfort, elevated liver enzyme levels, fatigue, malaise, hepatomegaly, hyperlipidemia, hypoglycemia, hypertension, iron-resistant anemia, kidney stones, growth delay, lactic academia, nephropathy, hepatic/renal glycogenosis, pancreatitis, hepatic adenomata, hepatocellular carcinoma, osteopenia/osteoporosis, platelet dysfunction, spider angiomata, ascites, splenomegaly, hard liver border, palmar erythema, or asterixis. In some embodiments, treatment includes improvement in liver enzyme levels, improvement in glycogen levels, improvement of liver symptoms, particularly, in reduction or prevention of GSD (e.g., GSD-III)-associated hypoglycemia, hepatomegaly, abnormal liver function, liver inflammation, and cirrhosis.

The terms, "improve," "prevent" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of the disease (e.g., GSD-Ia, GSD-III) as the individual being treated, who is about the same age as the individual being treated (to ensure that the stages of the disease in the treated individual and the control individual(s) are comparable).

As used herein, the term "therapeutic agent" means an agent utilized to treat, combat, ameliorate, prevent or improve an unwanted condition or disease of a subject. In part, embodiments described herein may be directed to the treatment of various steatosis-associated disorders, including, but not limited to GSD I, NAFLD, NASH, or a combination thereof. In part, embodiments described herein may be directed to the treatment of various cytoplasmic glycogen storage disorders, including, but not limited to glycogen storage disease type I (GSD I), glycogen storage disease III (GSD III), glycogen storage disease IV (GSD IV), glycogen storage disease V (GSD V), glycogen storage disease VI (GSD VI), glycogen storage disease VII (GSD VII), glycogen storage disease IX (GSD IX), glycogen storage disease XI (GSD XI), glycogen storage disease XII (GSD XII), glycogen storage disease XIII (GSD XIII), glycogen storage disease XIV (GSD XIV) (phosphoglucomutase deficiency), Danon disease (GSD 2B, LAMP-2 deficiency), Lafora disease, glycogenosis due to AMP-activated protein kinase gamma subunit 2-deficiency (PRKAG2), or cardiac glycogenosis due to AMP-activated protein kinase gamma subunit 2 deficiency. In some embodiments, GSD I may be selected from GSD Ia, GSD Ib, or GSD Ic. In some embodiments, GSD I is GSD Ia. In some embodiments, GSD-III may be selected from GSD-type IIIa, type IIIb, type IIIc, or type IIId.

The terms "therapeutically effective" or "effective", as used herein, may be used interchangeably and refer to an amount of a therapeutic composition of embodiments described herein. For example, a therapeutically effective amount of a composition is an amount of the composition, and particularly the active ingredient, such as GAA, that generally achieves the desired effect. For example, the desired effect can be an improvement, prevention, or reduction of a particular disease state.

A "therapeutically effective amount" or "effective amount" of a composition is an amount necessary or sufficient to achieve the desired result or clinical outcome. For example, the desired result or clinical outcome can be an improvement, prevention, or reduction of a particular disease state. The therapeutic effect contemplated by the embodiments herein includes medically therapeutic, cosmetically therapeutic and/or prophylactic treatment, as appropriate. The specific dose of a compound administered according to embodiments of the present invention to obtain therapeutic effects will, of course, be determined by the particular circumstances surrounding the case, including, for example, the compound administered, the route of administration, and the condition being treated. However, the effective amount administered can be determined by the practitioner or manufacturer or patient in light of the relevant circumstances including the condition to be treated, the choice of compound to be administered, and the chosen route of administration, and therefore, the above dosage ranges are not intended to limit the scope of the invention in any way. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

As used herein, the term "consists of" or "consisting of" means that the composition or method includes only the elements, steps, or ingredients specifically recited in the particular claimed embodiment or claim.

As used herein, the term "consisting essentially of" or "consists essentially of" means that the composition or method includes only the specified materials or steps and those that do not materially affect the basic and novel characteristics of the claimed invention.

Generally speaking, the term "tissue" refers to any aggregation of similarly specialized cells which are united in the performance of a particular function.

The term "animal" as used herein includes, but is not limited to, humans and non-human vertebrates such as wild, domestic and farm animals.

The term "patient" or "subject" as used herein is an animal, particularly a human, suffering from an unwanted disease or condition that may be treated by the therapeutic and/or compositions described herein. The individual, patient, or subject being treated may be a human (infant, child, adolescent, or adult human) having the disease to be treated, e.g. GSD IV. The individual may have residual enzyme (e.g. GBE) activity, or no measurable activity. In some embodiments, the individual may be an individual who has been recently diagnosed with the disease. Early treatment (treatment commencing as soon as possible after diagnosis) may be important to minimize the effects of the disease and to maximize the benefits of treatment.

The term "inhibiting" generally refers to prevention of the onset of the symptoms, alleviating the symptoms, or eliminating the disease, condition or disorder.

"Optional" or "optionally" means that the subsequently described event or circumstance may or may not occur, and that the description includes instances where the event occurs and instances where it does not.

As used herein, "room temperature" means an indoor temperature of from about 20° C. to about 25° C. (68 to 77° F.).

Throughout the specification of the application, various terms are used such as "primary," "secondary," "first," "second," and the like. These terms are words of convenience in order to distinguish between different elements, and such terms are not intended to be limiting as to how the different elements may be utilized.

By "pharmaceutically acceptable," "physiologically tolerable," and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

While the present disclosure is described in detail with reference to GSD Ia, the methods described herein may also be used to treat individuals suffering from other conditions related to steatosis, including, but not limited to, GSD Ib, GSD Ic, NAFLD, NASH, or combinations thereof.

Patients with Glycogen Storage Disease type I (GSD I) may present in the neonatal period with hypoglycemia and lactic acidosis; however, they more commonly present at 3-4 months of age with hepatomegaly and/or hypoglycemic seizures. These children often have doll-like faces with excess adipose tissue in cheeks, relatively thin extremities, short stature, and a protuberant abdomen that is due to massive hepatomegaly. The hallmarks of the disease are hypoglycemia, lactic acidosis, neutropenia, hyperuricemia, and hyperlipidemia. Hypoglycemia and lactic acidemia can occur after a short fast. The histology of the liver is characterized by a universal distension of hepatocytes by glycogen and fat. The lipid vacuoles are particularly large and prominent. There is little associated fibrosis. Hepatic adenomas are known to develop in most patients with type I glycogen storage disease by the time they reach their second or third decade of life. Severe renal injury with proteinuria, hypertension, and decreased creatinine clearance due to focal segmental glomerulosclerosis and interstitial fibrosis, ultimately leading to endstage renal disease, may also be seen in young adults. GSD I has three clinical subtypes (GSD Ia, GSD Ib, and GSD Ic).

Accordingly, some embodiments in the present disclosure are directed to treating a steatosis-associated disorder, the method comprising administering to a subject in need thereof a therapeutic agent. In some embodiments, the therapeutic agent may be an autophagy-inducing agent of embodiments herein, a lysosomal enzyme of embodiments herein, or a combination thereof. Some embodiments herein are directed to a method of treating GSD I, the method comprising administering to a subject in need thereof a therapeutic agent of embodiments herein. Some embodiments herein are directed to a method of treating GSD Ia, the method comprising administering to a subject in need thereof a therapeutic agent of embodiments herein. Some embodiments herein are directed to a method of treating GSD Ib, the method comprising administering to a subject in need thereof a therapeutic agent of embodiments herein. Some embodiments herein are directed to a method of treating GSD Ic, the method comprising administering to a subject in need thereof a therapeutic agent of embodiments herein. Some embodiments herein are directed to a method of treating NAFLD, the method comprising administering to a subject in need thereof a therapeutic agent of embodiments herein. Some embodiments herein are directed to a method of treating NASH, the method comprising administering to a subject in need thereof a therapeutic agent of embodiments herein.

Some embodiments herein are directed to a method of treating GSD I, the method comprising administering to a subject in need thereof a lysosomal enzyme and an autophagy inducing agent of embodiments herein. Some embodiments herein are directed to a method of treating GSD Ia, the method comprising administering to a subject in need thereof a lysosomal enzyme and an autophagy inducing agent of embodiments herein. Some embodiments herein are directed to a method of treating GSD Ib, the method comprising administering to a subject in need thereof a lysosomal enzyme and an autophagy inducing agent of embodiments herein. Some embodiments herein are directed to a method of treating GSD Ic, the method comprising administering to a subject in need thereof a lysosomal enzyme and an autophagy inducing agent of embodiments herein. Some embodiments herein are directed to a method of treating GSD I, the method comprising administering to a subject in need thereof a lysosomal enzyme and an autophagy inducing agent of embodiments herein, wherein the autophagy inducing agent is not a $\beta 2$ agonist. Some embodiments herein are directed to a method of treating GSD Ia, the method comprising administering to a subject in need thereof a lysosomal enzyme and an autophagy inducing agent of embodiments herein, wherein the autophagy inducing agent is not a $\beta 2$ agonist. Some embodiments herein are directed to a method of treating GSD Ib, the method comprising administering to a subject in need thereof a lysosomal enzyme and an autophagy inducing agent of embodiments herein, wherein the autophagy inducing agent is not a $\beta 2$ agonist. Some embodiments herein are directed to a method of treating GSD Ic, the method comprising administering to a subject in need thereof a lysosomal enzyme and an autophagy inducing agent of embodiments herein, wherein the autophagy inducing agent is not a $\beta 2$ agonist. Some embodiments herein are directed to a method of treating NAFLD, the method comprising administering to a subject in need thereof a lysosomal enzyme and an autophagy inducing agent of embodiments herein. Some embodiments herein are directed to a method of treating NASH, the method comprising administering to a subject in need thereof a lysosomal enzyme and an autophagy inducing agent of embodiments herein. In some embodiments, the autophagy inducing agent induces autophagy.

GSD Ia is a devastating disease that currently has few treatment options. Although much research has been performed to understand its pathophysiology, no study has been performed linking it to the key cellular process of autophagy. This link not only opens new insights into the pathogenesis and treatment of GSD Ia, but also leads to new potential therapies for a much more common disorder, NAFLD. The development of small molecule therapy for steatosis could provide new agents for NAFLD, which affects >20% of the population in developed countries and >40% of the US adult population.

The therapeutic agents of embodiments herein are believed to manipulate autophagy in GSD I and NAFLD to reverse steatosis in GSD I, NASH, and NAFLD. Autophagy is down-regulated in these disorders, and it is believed that stimulating autophagy reverses steatosis. The steatosis of GSD I closely resembles NAFLD, a major unmet health need estimated to affect nearly 40% in the population of the United States. If successful in GSD I, it is believed that modulating autophagy may be effective at reversing steatosis in other conditions such as NAFLD and NASH.

Some embodiments herein are directed to a method of reversing steatosis in a subject in need thereof, the method comprising administering to the subject a therapeutic agent of embodiments herein. Some embodiments herein are directed to a method of reversing glycogen storage in a subject in need thereof, the method comprising administering to the subject a therapeutic agent of embodiments herein. Some embodiments herein are directed to a method of modulating autophagy in a subject in need thereof, the method comprising administering to the subject a therapeutic agent of embodiments herein. Some embodiments herein are directed to a method of inducing autophagy in a subject in need thereof, the method comprising administering to the subject a therapeutic agent of embodiments herein. Some embodiments herein are directed to a method of reducing hepatosteatosis in a subject in need thereof, the method comprising administering to the subject a therapeutic agent of embodiments herein. Some embodiments are directed to treating hepatosteatosis in a subject in need thereof, the method comprising administering to the subject a therapeutic agent of embodiments herein.

In mammalian cells there are two spatially distinct pools of glycogen: cytoplasmic and lysosomal. Glycogenolysis is the major pathway of glycogen degradation which requires two enzymes, glycogen phosphorylase and glycogen debranching enzyme, for complete degradation of cytoplasmic glycogen. A minor pathway of glycogen degradation in the lysosomes by the enzyme acid alpha-glucosidase (GAA) also plays an important role in cellular glycogen metabolism.

Glycogen storage disease type III (GSD III) is caused by mutations in the glycogen debranching enzyme (GDE) gene, resulting in accumulation of glycogen with short outer chains in the cytoplasm of liver and muscle cells. GSD IV, another cytoplasmic GSD caused by deficiency of glycogen branching enzyme (GBE), is characterized by the deposits of less-branched amylopectin-like polysaccharide in muscle, liver, and the central nervous system (CNS). Although both diseases have cytoplasmic glycogen accumulation, GSD III glycogen has short outer chains and is soluble, while GSD IV glycogen is less-branched. Currently there is no treatment for these diseases.

GSD III has several subtypes. Most patients have disease involving both liver and muscle (type IIIa), some (~15% of all those with GSD-III) have only liver involvement (type IIIb), and in rare cases, there is a selective loss of only one of the two GDE activities: glucosidase (type IIIc) or transferase (type IIId). GSD IIIc affects only the muscle, and GSD IIId affects the muscle and the liver. During infancy and childhood, the dominant features are hepatomegaly, hypoglycemia, hyperlipidemia, and growth retardation. In individuals with muscle involvement (GSD IIIa), there is variable myopathy and cardiomyopathy.

GSD III patients have normal GAA activity in muscle, but excessive amounts of glycogen was found not only in the cytoplasm but also in the lysosomes. Similarly, both non-membrane-bound (cytoplasmic) glycogen and membrane-bound (lysosomal-like) glycogen were found in patients with GSD IV. These observations suggest an enhanced lysosomal glycogen trafficking in GSD III/GSD IV, and the endogenous GAA activity may not be sufficient to deplete the glycogen load in the lysosomes. Administration of rhGAA may enhance glycogen clearance in lysosomes and alter the glycogen flux in the cell, thereby reducing cytoplasmic glycogen levels in GSD III/GSD IV patients.

GSD IV patients usually present with hepatosplenomegaly and failure to thrive in the first 18 months of life. They develop liver cirrhosis that progresses to cause portal hypertension, ascites, esophageal varices, and liver failure that leads to death by age 5 years. Some patients can develop hepatic adenomas and hepatocellular carcinoma. Carbohydrate tolerance tests and blood glucose response to glucagon or epinephrine are normal in most patients, but fasting hypoglycemia, typically present in type I and type III disease (and in some cases of type VI and type IX disease) has been observed only occasionally in this disease when liver cirrhosis progresses and few hepatocytes are available for glucose mobilization. In addition to the hepatic presentation, there is a neuromuscular presentation of type IV disease that is heterogeneous. In the childhood form, patients present predominantly with a myopathy or cardiomyopathy. The adult form can present as an isolated myopathy or as a multisystem disorder with central and peripheral nervous system dysfunction accompanied by accumulation of polyglucosan material in the nervous system (so-called adult polyglucosan body disease).

In addition to GSD III and GSD IV, there are no effective treatments for other cytoplasmic GSDs, including GSD I (von Gierke's disease, glucose-6-phosphatase deficiency, Ib translocase deficiency), GSD V (McArdle's disease, a deficiency in muscle phosphorylase), GSD VI (Her's disease, a deficiency in liver phosphorylase), GSD VII (a deficiency in muscle phosphofructokinase; Tarui's disease), GSD IX (phosphorylase kinase deficiency), GSD XI (Franconi-Bickel syndrome; a deficiency in glucose transporter GLUT2), GSD XII (red cell aldolase deficiency; a deficiency in Aldolase A), GSD Xiii (a deficiency in b-enolase); GSD 0 (A deficiency in glycogen synthase), Lafora disease (laforin/malin deficiency), cardiac/muscle glycogenosis due to AMP-activated protein kinase gamma subunit 2-deficiency (PRKAG2 cardiac syndrome), GSD XIV due to phosphoglucomutase deficiency; and Danon disease (GSD 2B) due to LAMP-2 deficiency.

In some embodiments, the subject to be treated has a primarily hepatic form of the cytoplasmic glycogen storage disease to be treated. In some embodiments, the subject primarily has mainly hepatic and/or cardiac involvement of the cytoplasmic glycogen storage disease to be treated. In some embodiments, the cytoplasmic glycogen storage disease is in its early stages. In some embodiments, the subject does not have a significant amount of fibrosis.

All phosphorylase kinase deficiencies are referred to as type IX glycogen storage disease. GSD IX has six subtypes and primarily involves the liver and/or muscle as shown in Table 1.

TABLE 1

Various GSD IX SubTypes

| Subtype | Species | Affected Tissues | Inheritance | Mutant Gene/Subunit |
|---|---|---|---|---|
| IXa-1 | Human | Liver, blood cells | X chromosomal | PHKA2/$\alpha_L$ |
| IXa-2 | Human | Liver (in blood cells, normal, or high) | X chromosomal | PHKA2/$\alpha_L$ |
| IXb | Human | Liver, blood cells, muscle | autosomal | PHKB/$\beta$ |
| IXc | Human | Liver, blood cells | autosomal | PHKG2/$\gamma_{TL}$ |
| IXd | Human | Muscle | X chromosomal | PHKA1/$\alpha_M$ |
| IXe | Human | Muscle | autosomal | ? |
| IXf | Human | Heart | autosomal | ? |
| | I-Mouse* | Muscle | X chromosomal | PHKA1/$\alpha_M$ |
| | gsd-Rat† | Liver | autosomal | PHKG2/$\gamma_{TL}$ |

GSD XI may involve the liver and/or kidney. PRKAG2 deficiency primarily manifests in the heart and skeletal muscles. Some embodiments are directed to a method of treating a condition associated with PRKAG2 deficiency in an individual in need thereof comprises administering to the individual a therapeutically effective amount of an acid alpha-glucosidase. In some embodiments, the condition associated with PRKAG2 deficiency is selected from hypotonia, cardiac hypertrophy, cardiomyopathy, myopathy, cytoplasmic glycogen accumulation, ventricular hypertrophy, severe infantile hypertrophic cardiomyopathy, heart rhythm disturbances, increased left ventricular wall thickness, ventricular preexcitation, any other condition seen in patient having PRKAG2 deficiency, including glycogenosis or cardiac glycogenosis due to AMP-activated PRKAG2 deficiency, or a combination thereof. In some embodiments, the PRKAG2 deficiency is due to a mutation selected from PRKAG2 Het R531Qh mutation, PRKAG2 R302G mutation, PRKAG2 T400N mutation, PRKAG2 N488I missense mutation, PRKAG2 R531G missense mutation, PRKAG2 G100S missense mutation, or a combination thereof.

Some embodiments are directed to a method of improving motor skills in an individual with a PRKAG2 gene mutation comprising administering to the individual a therapeutically effective amount of acid alpha-glucosidase. Some embodiments are directed to a method of improving muscle strength and function in an individual with a PRKAG2 gene mutation comprising administering to the individual a therapeutically effective amount of acid alpha-glucosidase. Some embodiments are directed to a method of decreasing seizures in an individual with a PRKAG2 gene mutation comprising administering to the individual a therapeutically effective amount of acid alpha-glucosidase.

Some embodiments are directed to a composition comprising a therapeutic agent of embodiments herein and a lysosomal enzyme of embodiments herein. Some embodiments are directed to a composition comprising a β2 agonist and an acid alpha-glucosidase.

Some embodiments herein are directed to the use of a lysosomal enzyme for the treatment of conditions associated with PRKAG2 deficiency. In some embodiments, a method of treating a condition associated with PRKAG2 deficiency in an individual comprises administering to the individual a therapeutically effective amount of a lysosomal enzyme. In some embodiments, the condition is selected from hypotonia, cardiomyopathy, myopathy, cytoplasmic glycogen accumulation, ventricular hypertrophy, severe infantile hypertrophic cardiomyopathy, heart rhythm disturbances, increased left ventricular wall thickness, ventricular preexcitation, or a combination thereof.

Some embodiments are directed to a method of improving motor skills in an individual with a PRKAG2 gene mutation comprising administering to the individual a therapeutically effective amount of acid alpha-glucosidase. Some embodiments are directed to a method of improving muscle strength and function in an individual with a PRKAG2 gene mutation comprising administering to the individual a therapeutically effective amount of acid alpha-glucosidase. Some embodiments are directed to a method of decreasing seizures in an individual with a PRKAG2 gene mutation comprising administering to the individual a therapeutically effective amount of acid alpha-glucosidase.

Some embodiments are directed to a method of treating cardiac hypertrophy in an individual with a PRKAG2 gene mutation comprising administering to the individual a therapeutically effective amount of acid alpha-glucosidase. Some embodiments are directed to a method of treating cardiomyopathy in an individual with a PRKAG2 gene mutation comprising administering to the individual a therapeutically effective amount of acid alpha-glucosidase. Some embodiments are directed to a method of treating myopathy in an individual with a PRKAG2 gene mutation comprising administering to the individual a therapeutically effective amount of acid alpha-glucosidase.

In some embodiments, a therapeutic agent may be administered in combination with (e.g. prior to, after, and/or concurrently with) the lysosomal enzyme. In some embodiments, the therapeutic agent may be selected from a growth hormone, an autocrine glycoprotein, a β2 agonist, an agent to treat or prevent hypoglycemia (e.g. cornstarch), an agent to treat or prevent neutropenia, an agent to suppress glycogen synthase (e.g. RNAi; 20(S)-protopanaxadiol), an agent to prevent or reverse glycogen synthesis, an agent to treat or prevent fibrosis, an agent to improve mitochondrial function, an agent to treat any other symptom of the cytoplasmic storage disorders of embodiments herein, or a combination thereof.

In some embodiments, the autophagy-inducing agent may be selected from a thyroid hormone, a mTOR inhibitor, caffeine (trimethylxanthine), a steroid hormone, a PPAR-α agonist, an AMPK activator, a β2 agonist, a calcium channel blocker, a chemical chaperone, an intracellular inositol reducer, a Sirtuin-1 activator, a samesoid X receptor suppressor, or a combination thereof. In some embodiments, the steroid hormone may be dehydroepiandrosterone (DHEA). In some embodiments, the mTOR inhibitor may be selected from rapamycin, Torin1, temsirolimus (CCI-779), everolimus (RAD001), and ridaforolimus (AP-23573), Deforolimus (AP23573, MK-8669), mTORC1/mTORC2 dual inhibitor (e.g. PP242 WYE354), mTOR/P13K dual inhibitor (e.g. PI103 NVP-BEZ235), an analog thereof, or a combination thereof. In some embodiments, the AMPK activator may be selected from 5-Aminoimidazole-4-carboxamide ribonucleotide (AICAR), quercetin, α-lipoic acid, R-lipoic acid, metformin, resveratrol, guanidine, biguanidine, galegine, ginsenoside, curcumin, berberine, epigallocatechin gallate, theaflavin, hispidulin, a salicylate, a prodrug thereof, or a combination thereof. In some embodiments, the PPAR-α agonist may be selected from bezafibrate, genofibrate, ciprofibrate, gemfibrozil, clofibrate, an analog thereof, or a combination thereof. In some embodiments, the thyroid hormone may be selected from thyroxine (T4), triiodothyronine (T3), an analog thereof, or a combination thereof. In some embodiments, the calcium channel blocker may be verapamil. In some embodiments, the chemical chaperone may be trehalose. In some embodiments, the intracellular inositol reducer may be carbamazepine, lithium chloride, or a combination thereof. In some embodiments, the Sirtuin-1 activator may be methylene blue, resveratrol, or a combination thereof. In some embodiments, sarnesoid X receptor suppressor may be mifepristone. In some embodiments, the autophagy-inducing agent induces autophagy. In some embodiments, the autophagy-inducing agent is not a β2 agonist. In some embodiments, the autophagy-inducing agent is a β2 agonist.

β2 agonists are molecules that stimulate the β2-adrenergic receptor. Numerous β2 agonists are known in the art and may be used in the therapeutic methods of the invention. In some embodiments, the β2 agonist used in embodiments herein may be selected from albuterol, arbutamine, bambuterol, befunolol, bitolterol, bromoacetylalprenololmenthane, broxaterol, carbuterol, cimaterol, cirazoline, clenbuterol, clorprenaline, denopamine, dioxethedrine, dopexamine, ephedrine, epinephrine, etafedrine, ethylnorepinephrine, etilefrine, fenoterol, formoterol, hexoprenaline, higenamine, ibopamine, isoetharine, isoproterenol, isoxsuprine, mabuterol, metaproterenol, methoxyphenamine, norepinephrine, nylidrin, oxyfedrine, pirbuterol, prenalterol, procaterol, propranolol, protokylol, quinterenol, ractopamine, reproterol, rimiterol, ritodrine, salmefamol, soterenol, salmeterol, terbutaline, tretoquinol, tulobuterol, xamoterol, zilpaterol, zinterol, or a combination thereof. In some embodiments, β2 agonists used in the disclosed methods do not interact, or show substantially reduced interaction, with β1-adrenergic receptors. In some embodiments, the β2 agonist is a selective β2 agonist. In embodiments, the β2 agonist is clenbuterol, albuterol, fenoterol, formoterol, salmeterol, or a combination thereof. In embodiments, the β2 agonist is clenbuterol. In embodiments, the β2 agonist is albuterol. In some embodiments, the β2 agonist induces or promotes autophagy in the subject. The β2 agonist may be administered bimonthly, monthly, biweekly, weekly, twice weekly, daily, twice a day, three times a day, or more often a day. In some embodiments, the β2 agonist is administered in an amount of about 20 μg per day to about 2100 μg per day.

In the embodiments described herein, a therapeutically effective amount of clenbuterol may be administered. In some embodiments, the therapeutically effective amount of clenbuterol is about 80 μg/day to about 160 μg/day. In some embodiments, the therapeutically effective amount of clenbuterol is about 20 μg/day to about 2100 μg/day, about 20 μg/day to about 720 μg/day, about 20 μg/day to about 500 μg/day, about 20 μg/day to about 300 μg/day, about 20

µg/day to about 200 µg/day, about 40 µg/day to about 2100 µg/day, about 40 µg/day to about 720 µg/day, about 40 µg/day to about 500 µg/day, about 40 µg/day to about 300 µg/day, about 40 µg/day to about 200 µg/day, about 80 µg/day to about 2100 µg/day, about 80 µg/day to about 720 µg/day, about 80 µg/day to about 500 µg/day, about 80 µg/day to about 300 µg/day, about 80 µg/day to about 200 µg/day, or a range between any two of these values. In embodiments, the effective amount for a particular individual may be varied (e.g., increased or decreased) over time, depending on the needs of the individual.

In some embodiments, the therapeutic agent may be a lysosomal enzyme. In some embodiments, the lysosomal enzyme may be selected from glucocerebrosidase, acid alpha-glucosidase (acid alpha-glucosidase or GAA), alpha-galactosidase, alpha-n-acetylgalactosaminidase, acid sphingomyelinase, alpha-iduronidase, or a combination thereof. In some embodiments, the lysosomal enzyme may be acid α-glucosidase. In some embodiments, the acid alpha-glucosidase may be selected from a GAA, recombinant human acid alpha-glucosidase (rhGAA), alglucosidase alfa, neo-rhGAA, reveglucosidase alpha, an rhGAA administered with a chaperone (e.g. 1-deoxynojirimycin (DNJ), α-homonojirimycin, or castanospermine), or a combination thereof. In some embodiments, the steatosis-associated disorder may be selected from GSD I, NAFLD, NASH or a combination thereof. In some embodiments, GSD I may be selected from GSD Ia, GSD Ib, or GSD Ic. In some embodiments, the GSD I is GSD Ia.

A therapeutic agent, which is capable of enhancing expression of receptors for a lysosomal enzyme, may be administered to the patient as a pharmaceutical composition comprising the therapeutic agent and a pharmaceutically acceptable carrier or excipient. The preparation of a pharmacological composition that contains active ingredients dissolved or dispersed therein is well understood in the art. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. In addition, solid forms suitable for solution, or suspensions, in liquid prior to use can also be prepared. Formulation also varies according to the route of administration selected (e.g., solution, emulsion, capsule).

Some embodiments are directed to a composition comprising a therapeutic agent of embodiments herein, and pharmaceutically acceptable excipient. In some embodiments, the therapeutic agent may be an autophagy-inducing agent, a lysosomal enzyme, or a combination thereof. Some embodiments are directed to a composition comprising a β2 agonist and an acid alpha-glucosidase. Some embodiments are directed to an adeno-associated virus ("AAV") vector encoding a lysosomal enzyme, such as acid alpha-glucosidase.

According to some embodiments, a method of treating a steatosis-associated disorder comprises administering a therapeutically effective amount of an autophagy-inducing agent. The autophagy-inducing agent may be administered at a dosage of, for example, 0.1 to 100 mg/kg, such as 0.5, 1.0, 1.1, 1.6, 2, 8, 9, 10, 11, 15, 16, 17, 18, 19, 20, 21, 22, 27, 28, 29, 30, 40, 45, 50, 60, 70, 80, 90 or 100 mg/kg per day, or a range between any two of these values. Dosage forms suitable for internal administration may contain from about 0.1-500 milligrams of active ingredient per unit. In these pharmaceutical compositions, the active ingredient may be ordinarily be present in an amount of about 0.5-95% by weight based on the total weight of the composition.

In some embodiments, the autophagy-inducing agent will be administered in a dose of about 80 µg/day to about 160 µg/day. In some embodiments, the autophagy-inducing will be administered in a dose of about 20 µg/day to about 2100 µg/day, about 20 µg/day to about 720 µg/day, about 20 µg/day to about 500 µg/day, about 20 µg/day to about 300 µg/day, about 20 µg/day to about 200 µg/day, about 40 µg/day to about 2100 µg/day, about 40 µg/day to about 720 µg/day, about 40 µg/day to about 500 µg/day, about 40 µg/day to about 300 µg/day, about 40 µg/day to about 200 µg/day, about 80 µg/day to about 2100 µg/day, about 80 µg/day to about 720 µg/day, about 80 µg/day to about 500 µg/day, about 80 µg/day to about 300 µg/day, about 80 µg/day to about 200 µg/day, or a range between any two of these values. In embodiments, the effective amount for a particular individual may be varied (e.g., increased or decreased) over time, depending on the needs of the individual. In some embodiments, the effective amount of clenbuterol is about 80 to 160 µg/day (or 40 to 80 micrograms by mouth twice daily).

In some embodiments, the effective amount of other drugs that enhance autophagy are provided in Table 2.

TABLE 2

Effective Amount of Various Autophagy Enhancing Drugs

| Drug | Source | Dose and method of administration |
|---|---|---|
| α-lipoic acid (AMPK, activator) | 100 mg capsules (OTC dietary supplement) | 20 mg/kg PO daily (adult dose 300 mg BID) |
| Metformin (AMPK activator) | 500 mg Glucophage oral tablets, Bristol Meyers Squibb | 10 mg/kg PO BID (adult dose 500 mg BID) |
| Verapamil | 40 mg oral tablets (generic) | 2 mg/kg PO TID (adult dose 80 mg TID) |
| Trehalose | 100% Pure Trehalose, Swanson Ultra (OTC dietary supplement) | 2-10 g PO daily |
| Carbamezipine | 100 mg tablets Tegretol or oral suspension | 10 mg/kg PO daily (adult dose 200 mg BID) |
| Lithium chloride | lithium citrate 300 mg/5 ml syrup | 10 mg/kg BID PO (adult dose 900 mg BID ) |
| Bezafibrate | Powder from Sigma | 3.3 mg/kg daily (adult dose 200 mg daily) |
| Methylene blue | U.S.P. powder available from chemical supply houses or 65 mg tablets | 0.4-1 mg/kg TID (adult dose 50 mg TID) |
| Resveratrol | Resvantage Canine, Advantage Biosciences 5 mg tablet | 1 mg/kg PO daily (adult dose 20-500 mg daily |
| Mifepristone | 200 mg Mifeprex tablet (Danco laboratories) | 3 mg/kg daily PO (adult dose 100 to 300 mg daily) |

In some embodiments, the autophagy-inducing agent may be administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or a range between any two of these values. In some embodiments, the autophagy-inducing agent may be administered at least once every 1, 2, 3, 4, 5, 6, 7, 8, 9, 10, 11, 12, 13, 14, 15, 16, 17, 18, 19, 20 weeks, or a range between any two of these values. In some embodiments, the autophagy-inducing agent may be administered using single or divided doses of every 60, 48, 36, 24, 12, 8, 6, 4, or 2 hours, or a range between any two of these values, or a combination thereof.

For example, in some embodiments, an autophagy-inducing agent may be administered as a single dose at a single time point, or administered to the patient over the span a several hours (e.g., once every hour, once every two hours, once every three hours, etc.) or over the span of several days (e.g., once a day, once every two days, once every three days, etc.).

As known by those of skill in the art, the optimal dosage of autophagy-inducing agents useful in the present disclosure depend on the age, weight, general health, gender, and severity of the steatosis-associated disorder of the individual being treated or severity of the cytoplasmic glycogen storage disorder of the individual being treated, as well as route of administration and formulation. A skilled practitioner is able to determine the optimal dose for a particular individual. Additionally, in vitro or in vivo assays may be employed to help to identify optimal dosage ranges, for example, by extrapolation from dose-response curves derived from in vitro or animal model test systems.

In some embodiments, the therapeutic agent (e.g. β2 agonist) may be administered at a dosage of, for example, 0.1 to 100 mg/kg, such as 0.5, 1.0, 1.1, 1.6, 2, 4, 8, 9, 10, 11, 15, 16, 17, 18, 19, 20, 21, 22, 27, 28, 29, 30, 40, 45, 50, 60, 70, 80, 90 or 100 mg/kg per day, or a range between any two of these values. Dosage forms suitable for internal administration may contain from about 0.1-500 milligrams of active ingredient per unit. In these pharmaceutical compositions, in some embodiments, the active ingredient may be present in an amount of about 0.5-95% by weight based on the total weight of the composition.

Administering of a therapeutic agent useful in the disclosed methods may be performed by any suitable route, including administration by inhalation or insufflation (either through the mouth or the nose) or oral, sublingual, buccal, parenteral, topical, subcutaneous, intraperitoneal, intravenous, intrapleural, intraoccular, intraarterial, rectal administration, or within/on implants, e.g., matrices such as collagen fibers or protein polymers, via cell bombardment, in osmotic pumps, grafts comprising appropriately transformed cells, etc. In particular, the disclosed therapeutic methods and agents are useful for treating steatosis-associated disorders characterized by severe brain involvement without the need for invasive administration techniques directly to brain (e.g., intrathecal administration).

A therapeutic agent may be administered to the patient as a pharmaceutical composition comprising the therapeutic agent and a pharmaceutically acceptable carrier or excipient. The preparation of a pharmacological composition that contains active ingredients dissolved or dispersed therein is well understood in the art. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. In addition, solid forms suitable for solution, or suspensions, in liquid prior to use can also be prepared. Formulation also varies according to the route of administration selected (e.g., solution, emulsion, capsule).

Pharmaceutically acceptable carriers can include inert ingredients which do not interact with the autophagy-inducing agent, the β2 agonist, lysosomal enzyme and/or other additional therapeutic agents. These carriers include sterile water, salt solutions (e.g., NaCl), physiological saline, bacteriostatic saline (saline containing about 0.9% benzyl alcohol), phosphate-buffered saline, Hank's solution, Ringer's-lactate saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, dextrose, lactose, trehalose, maltose or galactose, magnesium stearate, talc, silicic acid, viscous paraffin, perfume oil, fatty acid esters, hydroxymethylcellulose and polyvinyl pyrolidone, as well as combinations thereof. The compositions may be mixed with auxiliary agents, e.g., lubricants, preservatives, stabilizers, wetting agents, emulsifiers, salts for influencing osmotic pressure, pH buffers, coloring, flavoring and/or aromatic substances and the like which do not deleteriously react with the active compounds. In addition, the compositions of embodiments herein may be lyophilized (and then rehydrated) in the presence of such excipients prior to use.

Standard pharmaceutical formulation techniques as known in the art can be employed, such as those described in Remington's Pharmaceutical Sciences, Mack Publishing Company, Easton, Pa. Methods for encapsulating compositions. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose or magnesium carbonate. For example, a composition for intravenous administration typically is a solution in a water-soluble carrier, e.g., sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is administered by injection, an ampule of sterile water for injection or saline can be provided so that the ingredients may be mixed prior to administration.

The therapeutic agent of embodiments herein may be administered as a neutral compound or as a salt or ester. Pharmaceutically acceptable salts include those formed with free amino groups such as those derived from hydrochloric, phosphoric, acetic, oxalic or tartaric acids, and those formed with free carboxyl groups such as those derived from sodium, potassium, ammonium, calcium, ferric hydroxides, isopropylamine, triethylamine, 2-ethylamino ethanol, histidine, and procaine. For instance, salts of compounds containing an amine or other basic group can be obtained by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base such as a hydroxide base. Salts of acidic functional groups contain a countercation such as sodium or potassium.

Table 3 shows exemplary therapeutic agents, dosage, route of administration and frequency.

This table is exemplary, and is not meant to be limiting.

TABLE 3

Exemplary Therapeutic Agents

| Name | Dose | Route | Frequency |
|---|---|---|---|
| Bambuterol | Adult: 10 mg, increased to 20 mg after 1-2 wk. Child (6-12 yr.): 5 mg, may be increased after 1-2 wk. (>10 not recom. in oriental children) Child (2-5 yr.): 5 mg | Oral solution | daily for children and adults |
| Bitolterol (Adult and Child the same) | Intermittent Nebulization: 0.5-1.5 mg, severe patients (2 mg-8 mg). Continuous Nebulization: 2.5 mg w/max. of 14 mg | Inhalation | 2 inhalations every 8 hr. Do not exceed 3 inhalations every 6 hr. or 2 inhalations every 4 hr. |
| Ephedrine (Adults only) | Oral/Subcutaneous: (Initial Dose) 25-50 mg IV: 5-25 mg (over 15 min.) | Oral, Subcutaneous, IV | As needed; 150 mg/day (max dose) |
| Ephedrine (Child only >2 yr.) | 2-3 mg/kg | Oral, Subcutaneous | daily, divided up into 4-6 doses |
| Epinephrine (Adult only) | 0.3 mg 0.5 mL or one vial (nebulizer) (0.1 mg/mL, solution) 0.1 to 1 mg | IV, Inhalation, Intaspinal | As needed |
| Epinephrine (Child only) | 0.15 mg (1.0 mg/mL) 0.01 mg/kg (0.1 mg/mL) 0.005-0.01 mg/kg | IV, Inhalation | As needed, 0.5 mg/dose (max dose) |
| Ethylnorepinephrine | 0.5-1 mL | Injection | As recommended |
| Etilefrine (Adult only) | Injection: 10 mg IV: 0.2-0.6 mg/min. | Injection, IV | Injection: every 1-3 hr., if necessary |
| Etilefrine (Child only) | <2 yr. -Injection: 2-4 mg IV: 0.05-0.2 mg/min. 2-6 yr. -Injection: 4-7 mg IV: 0.1-0.4 mg/min. >6 yr. -Injection: 7-10mg IV: 0.2-0.5 mg/min. | Injection, IV | Injection: every 1-3 hr., if necessary |
| Fenoterol (Adult only) | Inhalation-0.007-0.035 mg/kg Oral-100-200 mcg | Inhalation, Oral | Inhalation-every 6 hr, Oral-every 8 hr. |
| Fenoterol (Child only) | Inhalation-8 µg/kg | Inhalation | every 8 hr. |
| Formoterol (Adult only) | 12 mcg of powder 12 mcg inhalation capsule or 20 mcg/2 mL inhalation solution | Inhalation | 15 min. before exercise, every 12 hr.; 24 mcg (max dose) every 12 hrs. for inhalation capsule (24 mcg max dose) and every 12 hrs. for inhalation solution |
| Formoterol (Child only) | 12 mcg of powder | Inhalation | every 12 hr., 24 mcg (max dose) |
| Isoetharine (Adult only) | 0.005-0.09 mg/kg | Inhalation | Every 4 hrs. |
| Isoproterenol (Adult only) | 1:200 solution: 5-15 deep inhalations. 1:100 solution: 3-7 deep inhalations Dilute 1 mL to 10 mL W/NaCl Dilute 5 mL to 500 mL in 5% dextrose injection | Inhalation, IV | If relief is not observed, repeat dosing. Repeat up to 5x/day. Initial dose may be repeated when necessary administer at 5 mcg/min. 0.5-5. mcg/min. |
| Isoproterenol (Child only) | 1:200 solution: 5-15 deep inhalations. Do not use more than 0.25 mL of 1:200 solution during one treatment. | Inhalation | Asthma (Acute)-If relief is not observed, repeat dosing. Repeat up to 5x/day. |
| Metaproterenol (Adult only) | Oral: 20 mg Inhalation aerosol: 2-3 inhalations Inhalation solution: 10-15 mcg | Oral, Inhalation | Oral: 3-4x/day Inhalation aerosol: every 3-4 hrs. up to 12 inhalations/day Inhalation solution: every 3-6 hr. |
| Metaproterenol (Child only) | Infant and children (Inhalation)(<12 yr.): 0.5-1 mg/kg; min. dose: 5 mg; max. dose: 15 mg Infant and children (Oral) (<2 yr).: 0.4 mg/kg/dose Children (Oral) (2-6 yr.): 1.3-2.6 mg/kg/day Children (Oral)(6-9 yr.): 10 mg Children (oral)(>9 yr.): 20 mg | Oral, Inhalation | Infant and children (Inhalation) (< 12 yr.): every 4-6 hr. Infant and children (Oral) (<2 yr).: dose divided into 3-4x/day (Children); divided into 8-12x/day (Infants) Children (Oral) (2-6yr.): divided every 6-8hr. Children (Oral)(6-9 yr.): 3-4x/day Children (oral)(>9 yr.): 3-4x/day |
| Norepinephrine (Adult only) | Initial dose: 2-4 mcg/min Maintenance dose: avg. 1-12 mcg/min. (based on rate for low normal blood pressure) | IV | Initial dose: daily Maintenance dose: daily |
| Nylidrin (Adult only) | 3-12 mg | Oral | 3-4x/day |
| Pirbuterol (Adult and child) | 0.4 mg | Inhalation | repeated every 4-6 hr. |
| Propranolol | Intial Dose: 40 mg (Immed. Release); 80 mg (Sustained Release) Maintenance Dose: 120-240 mg (Immed. Release); 120-160 mg (Sustained Release) Immed. Release: 80-320 mg (total dose) Sustained Release: (avg. optimal dose) 160 mg 10-30 mg (oral); 1-3 mg (IV) Initial dose: 40 mg | Oral, IV | Intial dose: 2x/day (Immed. Release); 1x/day (Sustained Release) Maintenance dose: 1x/day (Immed. And Sustained Release) Immed. Release: Doses divided into 2-4x/day Sustained Release: daily 3-4x/day (oral); rate not exceeding |

TABLE 3-continued

Exemplary Therapeutic Agents

| Name | Dose | Route | Frequency |
|---|---|---|---|
| | Maintenance: 180-240 mg<br>Intial Dose: 80 mg (Immed Release); 80 mg (Sustained Release)<br>Maintenance Dose: 160-240 mg (immed. and Sustained Release) | | 1 mg/min (IV)<br>Intial Dose: 3x/day for 1 month<br>Maintenance: 2-4x/day in divided doses<br>Intial Dose: per day in divided doses (for immed. and sustained release)<br>Maintenance: daily |
| Ritodrine (Adults only) | Capsules: 40 mg<br>Tablets: 10-20 mg<br>Injection: 50-350 mcg/min | Oral,<br>Injection | Capsules: every 8-12 hrs.<br>Tablets: every 4-6 hrs. |
| Salmeterol (Adults and Child) | 50 mcg | Inhalation | every 12 hr. |
| Terbutaline | IV: 0.08-6 mcg/kg/min<br>Subcutaneous Inj.: 0.25 mg<br>Inhalation: 2 inhalations<br>Oral: 2.5-7.5 mg | Oral, IV,<br>Injection | Inhalation: 60 sec. apart, every 2-6 hr.<br>Sub. Inj.: As needed every 15-30 min., do not exceed 0.4 mg in 4 hr., or every 6 hr.<br>Oral: 3x/day at 6 hr. Intervals, do not exceed 15 mg in 24 hr.<br>IV: max dose 80 mcg/min. |
| Clenbuterol | 40 μg/day up to 160 μg/day; 40 μg once daily; 40 μg BID; 80 μg in the morning, 40 μg in the evening; 80 μg BID | oral, tablet and syrup | daily or twice daily |
| Albuterol | 4 mg/day up to 16 mg/day oral; 4 mg once daily, 4 mg twice daily, 4 mg in the morning and 8 mg in the evening, 8 mg twice daily. | oral, tablet and syrup | daily or twice daily |

The methods of the present disclosure contemplate single as well as multiple administrations, given either simultaneously or over an extended period of time. In embodiments, the therapeutic agent may be administered at regular intervals (i.e., periodically) and on an ongoing basis, depending on the nature and extent of effects of the steatosis-associated disorder or depending on the nature and extent of effects of the cytoplasmic glycogen storage disorder, and also depending on the outcomes of the treatment. In some embodiments, the therapeutic agent's periodic administrations may be bimonthly, monthly, biweekly, weekly, twice weekly, daily, twice a day, three times a day, or more often a day. Administrative intervals may also be varied, depending on the needs of the patient. Therapeutic regimens may also take into account half-life of the administered therapeutic agents of embodiments herein. For example, in some embodiments, in times of physical illness or stress, if anti-lysosomal enzyme antibodies become present or increase, or if disease symptoms worsen, the interval between doses may be decreased. Therapeutic regimens may also take into account half-life of the administered therapeutic agents of embodiments herein.

Some embodiments are directed to a method of treating a steatosis-associated disorder comprising administering a composition comprising a therapeutic agent of embodiments herein, and a pharmaceutically acceptable excipient. In some embodiments, the steatosis-associated disorder may be GSD Ia, GSD Ib, GSD Ic, NAFLD, NASH, or a combination thereof. In some embodiments, the therapeutic agent may include a lysosomal enzyme, an autophagy-inducing agent, or a combination thereof. In some embodiments, the autophagy-inducing agent may be administered in combination with (e.g. prior to, after, and/or concurrently with) a lysosomal enzyme. Some embodiments provide for a method of treating a steatosis-associated disorder, the method comprising administering an adjuvant therapy comprising an autophagy-inducing agent of embodiments herein to enhance efficacy of an enzyme replacement therapy. In some embodiments, the enzyme replacement therapy may be administration of a lysosomal enzyme.

In some embodiments, for the treatment of cytoplasmic glycogen storage disorders, a therapeutic agent of embodiments described herein may be administered to a patient in combination with a lysosomal enzyme. In some embodiments, a therapeutic agent and lysosomal enzyme may be components of a single pharmaceutical composition. In some embodiments, a therapeutic agent and lysosomal enzyme may be components of separate pharmaceutical compositions that are mixed together before administration. In some embodiments, the therapeutic agent and lysosomal enzyme may be components of separate pharmaceutical compositions that are administered separately. In some embodiments, the therapeutic agent and the lysosomal enzyme may be administered simultaneously, without mixing (e.g., by delivery of the β2 agonist on an intravenous line by which the lysosomal enzyme is also administered). In some embodiments, the therapeutic agent may be administered separately (e.g., not admixed), but within a short time frame (e.g., within 24 hours) prior to or subsequent to administration of the lysosomal enzyme. A synergistic effect may support reduced dosing of ERT when used with the therapeutic agent and a reduced dosing of the therapeutic agent.

In some embodiments, the lysosomal enzyme (such as GAA) may be administered to the individual in a form that, when administered, targets tissues such as the tissues affected by the disease (e.g., liver, brain, heart, or muscle). In some embodiments, the lysosomal enzyme is administered in its precursor form. In some embodiments, a mature form of the lysosomal enzyme (e.g. GAA) that has been modified to contain motifs to allow efficient uptake of the lysosomal enzyme may be administered. In embodiments, the lysosomal enzyme may be selected from glucocerebrosidase, alpha-glucosidase (e.g., acid alpha-glucosidase), alpha-galactosidase (e.g., alpha-gal, alpha-galactosidase or alpha-gal), alpha-n-acetylgalactosaminidase, acid sphingomyelinase, and alpha-iduronidase.

In some embodiments, a method of treating a steatosis-associated disorder of embodiments herein comprises administering a lysosomal enzyme. In some embodiments, a method of treating a steatosis-associated disorder of embodiments herein comprises administering a lysosomal enzyme and an autophagy-inducing agent. In some embodiments, a method of treating a steatosis-associated disorder of embodiments herein comprises administering an autophagy-inducing agent as an adjunctive therapy to lysosomal enzyme replacement therapy.

In some embodiments, the lysosomal enzyme is acid alpha-glucosidase (GAA). In some embodiments, the GAA may be human. In some embodiments, the GAA is recombinant GAA. In some embodiments, the GAA is a precursor form of recombinant human GAA (rhGAA). In some embodiments, the human GAA is administered in its precursor form, as the precursor contains motifs which allow efficient receptor-mediated uptake of GAA. Alternatively, a mature form of human GAA that has been modified to contain motifs to allow efficient uptake of GAA, can be administered. In some embodiments, the GAA is either GAA, rhGAA, alglucosidase alfa, neo-rhGAA (modified recombinant human GAA with synthetic oligosaccharide ligands which is sold by Genzyme Corp.), reveglucosidase alpha (a fusion of IGF-2 and GAA sold by Biomarin Pharmaceuticals, Inc.), ATB200 (an rhGAA with a higher bis-M6P content) that is administered in combination with AT221 (an oral chaperone molecule—e.g. 1-deoxynojirimycin (DNJ), α-homonojirimycin, or castanospermine)) (sold by Amicus Therapeutics, Inc.), a portion thereof, or a combination thereof. The rhGAA may be alglucosidase alfa (sold by Genzyme Corp. under the tradename Myozyme®) (for infantile onset Pompe disease) and Lumizyme*).

GAA may be obtainable from a variety of sources. In some embodiments, a recombinant human acid α-glucosidase (rhGAA) produced in Chinese hamster ovary (CHO) cell cultures is used (see, e.g., Fuller, M. et al., Eur. J. Biochem., 234:903 909 (1995); Van Hove, J. L. K. et al., Proc. Natl. Acad. Sci., USA 93:65 70 (1996) and U.S. Pat. No. 7,056,712). Production of GAA in CHO cells yields a product having glycosylation that allows significant and efficient uptake of GAA in tissues such as heart and muscle. In some embodiments, Myozyme* (alglucosidase alfa from Genzyme Corp.), or other recombinant human GAA, may be used in accordance with the invention.

In embodiments, the GAA may have a specific enzyme activity in the range of about 1.0 to about 8.0 μmol/min/mg protein, about 2.0 to about 8.0 μmol/min/mg protein, about 3.0-8.0 mol/min/mg protein, about 4.0 to about 8.0 μmol/min/mg protein, about 2.0 to about 3.5 mol/min/mg protein, about 1.0 to about 3.5 μmol/min/mg protein, about 1.0 to about 5 mol/min/mg protein, about 2.0 to about 5 μmol/min/mg protein, or a range between any two of these values. In some embodiments, the GAA has a specific enzyme activity of at least about 1.0 mol/min/mg protein, at least about 2.0 μmol/min/mg protein, at least about 2.5 μmol/min/mg protein, at least about 2.75 μmol/min/mg protein, at least about 3.0 μmol/min/mg protein, at least about 3.5 μmol/min/mg protein, at least about 4.0 μmol/min/mg protein, at least about 5.0 mol/min/mg protein, at least about 6.0 μmol/min/mg protein, at least about 7.0 μmol/min/mg protein, at least about 8.0 μmol/min/mg protein, or a range between any two of these values.

For example, in some embodiments, GAA may be administered as a single dose at a single time point, or administered to the patient over the span a several hours (e.g., once every hour, once every two hours, once every three hours, etc.) or over the span of several days (e.g., once a day, once every two days, once every three days, etc.).

Where a combination therapy is used, in some embodiments, administration of a therapeutic agent and the lysosomal enzyme can take place once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or at least once every 1, 2, 3, 4, 5, 6, 7, 8, 9, 10, 11, 12, 13, 14, 15, 16, 17, 18, 19 or 20 weeks, any range of two of these values, or any combination thereof, using single or divided doses of every 60, 48, 36, 24, 12, 8, 6, 4, or 2 hours, or any combination thereof.

In some embodiments, the lysosomal enzyme may be administered alone, or in compositions or medicaments comprising the lysosomal enzyme, as described herein. In some embodiments, for the treatment of steatosis-associated disorders, an autophagy-inducing agent of embodiments described herein may be administered to a patient in combination with a lysosomal enzyme. In some embodiments, an autophagy-inducing agent and lysosomal enzyme may be components of a single pharmaceutical composition. In some embodiments, an autophagy-inducing agent and lysosomal enzyme may be components of separate pharmaceutical compositions that are mixed together before administration. In some embodiments, the autophagy-inducing agent and lysosomal enzyme may be components of separate pharmaceutical compositions that are administered separately. In some embodiments, the autophagy-inducing agent and the lysosomal enzyme may be administered simultaneously, without mixing (e.g., by delivery of the autophagy-inducing agent on an intravenous line by which the lysosomal enzyme is also administered). In some embodiments, the autophagy-inducing agent may be administered separately (e.g., not admixed), but within a short time frame (e.g., within 24 hours) prior to or subsequent to administration of the lysosomal enzyme. A synergistic effect may support reduced dosing of ERT when used with the autophagy-inducing agent and a reduced dosing of the autophagy-inducing agent.

In some embodiments, the acid alpha-glucosidase and the β2 agonist are components of separate pharmaceutical compositions that are administered separately. In some embodiments, the β2 agonist and the acid alpha-glucosidase are components of separate pharmaceutical compositions that are mixed together before administration. In some embodiments, the 32 agonist is administered separately prior to, concurrently with, or subsequent to administration of the acid alpha-glucosidase. In some embodiments, the β2 agonist and the acid alpha-glucosidase are in a single pharmaceutical composition.

In embodiments, the lysosomal enzyme may be optionally administered in conjunction with other agents, such as antihistamines or immunosuppressants or other immunotherapeutic agents, such as methotrexate, that counteract anti-lysosomal enzyme antibodies. In embodiments, the lysosomal enzymes may include a human enzyme, recombinant enzyme, wild-type enzyme, synthetic enzyme, or a combination thereof.

In some embodiments, gene therapy may be used. For example, genes encoding the aforesaid lysosomal enzymes, such as acid alpha-glucosidase, may be used. For gene therapy, genes encoding the aforesaid lysosomal enzymes may be used. In some embodiments, pro-autophagy genes may be used in gene therapy, for example, genes encoding Adenosine-monophosphate-activated protein kinase ("AMPK") and/or transcription factor EB ("TFEB").

In some embodiments, administration of a lysosomal enzyme may also encompass administration of a functional equivalent of a lysosomal enzyme. A functional equivalent may include a compound different from the lysosomal enzyme that, when administered to the patient, replaces the function of the lysosomal enzyme to treat the lysosomal storage disorder. Such functional equivalents may include mutants, analogs, and derivatives of lysosomal enzymes.

Some embodiments are directed to a method of treating glycogen storage disorder I (GSD I) in an individual in need thereof comprises administering to the individual a therapeutically effective amount of an acid alpha-glucosidase. In some embodiments, the GSD I is selected from GSD Ia, GSD Ib, GSD Ic, or a combination thereof. In some embodiments, the individual has steatosis. In some embodiments, the method further includes administration of an additional therapeutic agent. In some embodiments, the method further includes administration of an additional therapeutic agent that increases uptake of the acid alpha-glucosidase. In some embodiments, the additional therapeutic agent is a β2 agonist.

According to some embodiments, a method of treating a cytoplasmic glycogen storage disorder may include increasing expression of receptors for the lysosomal enzyme, or otherwise increasing cell surface density of such receptors, in an individual in need thereof. Accordingly, in some embodiments, a method of treating a cytoplasmic glycogen storage disorder of embodiments herein comprises administering an adjunctive therapy comprising a therapeutic agent to enhance the efficacy of a lysosomal enzyme. In some embodiments, a method of treating a cytoplasmic glycogen storage disorder of embodiments herein comprises administering a lysosomal enzyme and another therapeutic agent. In some embodiments, a method of treating a cytoplasmic glycogen storage disorder of embodiments herein comprises administering a therapeutic agent as an adjunctive therapy to lysosomal enzyme replacement therapy. In some embodiments, the therapeutic agent may be selected from a growth hormone, an autocrine glycoprotein, a β2 agonist, an agent to treat or prevent hypoglycemia (e.g. cornstarch), an agent to treat or prevent neutropenia, an agent to suppress glycogen synthase (e.g. RNAi; 20(S)-protopanaxadiol), an agent to prevent or reverse glycogen synthesis, an agent to treat or prevent fibrosis (e.g. PDE4 inhibitors), an agent to improve mitochondrial function, an agent to treat any other symptom of the cytoplasmic storage disorders of embodiments herein, or a combination thereof. Therapeutic agents of embodiments herein may selectively modulate expression of receptors for particular lysosomal enzymes. Expression of receptors for a lysosomal enzyme may also be increased by behaviors, such as exercise. In some embodiments, a β2 agonist may be administered to an individual suffering from adult-onset or late-onset glycogen storage disease II, or a patient who presents with only partial enzyme deficiency, wherein administering the 32 agonist results in biochemical correction of the enzyme deficiency in target tissues and improved motor function.

In some embodiments, the cytoplasmic glycogen storage disorder may be selected from glycogen storage disease type I (GSD I), glycogen storage disease III (GSD III), glycogen storage disease IV (GSD IV), glycogen storage disease V (GSD V), glycogen storage disease VI (GSD VI), glycogen storage disease VII (GSD VII), glycogen storage disease IX (GSD IX), glycogen storage disease XI (GSD XI), glycogen storage disease XII (GSD XII), glycogen storage disease XIII (GSD XIII), glycogen storage disease XIV (GSD XIV) (phosphoglucomutase deficiency), Danon disease (GSD 2B, LAMP-2 deficiency), Lafora disease, a condition associated with protein kinase gamma subunit 2-deficiency (PRKAG2) deficiency, any other condition where there is cytoplasmic accumulation of glycogen, or a combination thereof. In some embodiments, the cytoplasmic glycogen storage disorder may be GSD III, GSD IV or a condition associated with protein kinase gamma subunit 2-deficiency (PRKAG2) deficiency.

According to some embodiments, a method of treating a glycogen storage disease of embodiments herein may include increasing expression of receptors for acid alpha-glucosidase, or otherwise increasing cell surface density of such receptors, in an individual in need thereof using a therapeutic agent. Representative therapeutic agents capable of inducing such increased expression include growth hormones (e.g., human growth hormone), autocrine glycoproteins (e.g., Follistatin), and β2 agonists. Such therapeutic agents may selectively modulate expression of receptors for the lysosomal enzymes of embodiments herein, (e.g acid alpha-glucosidase). Expression of receptors for acid alpha-glucosidase may also be increased by behaviors, such as exercise. In some embodiments, a β2 agonist is administered to a patient suffering from glycogen storage disease of embodiments herein, wherein administering the β2 agonist results in biochemical correction of the enzyme deficiency in target tissues (e.g. liver) and improved motor function.

Also encompassed by the instant disclosure are methods of increasing efficacy of a glycogen storage disease therapy, e.g., substrate deprivations and small molecule therapies, GAA replacement therapy, including gene therapy (e.g., transfection of cells in a patient with a vector encoding a deficient lysosomal enzyme), or any other form of therapy where the levels of the deficient lysosomal enzyme in a patient are supplemented. For example, these therapies may comprise increasing expression of receptors for a lysosomal enzyme, for example, by administering an effective amount of β2 agonist.

In some aspects, a therapeutic agent capable of increasing expression of receptors for a lysosomal enzyme is administered in combination with a second therapeutic agent or treatment, and in such cases, the therapeutic agents or treatments may be administered concurrently or consecutively in either order. For concurrent administration, the therapeutic agents may be formulated as a single composition or as separate compositions. The optimal method and order of administration of the therapeutic agents capable of increasing expression of a receptor for a lysosomal enzyme and a second therapeutic agent or treatment can be ascertained by those skilled in the art using conventional techniques and in view of the information set out herein.

The disclosed combination therapies may elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

In some embodiments, for the treatment of a cytoplasmic glycogen storage disorder, a therapeutic agent of embodiments herein may be administered to a patient in combination with a lysosomal enzyme. In some embodiments, a therapeutic agent and lysosomal enzyme may be components of separate pharmaceutical compositions that are mixed together before administration, or that are administered separately. In some embodiments, a therapeutic agent can also be administered simultaneously, without mixing (e.g., by delivery of the β2 agonist on an intravenous line by which the lysosomal enzyme is also administered). In some embodiments, a therapeutic agent may be administered separately (e.g., not admixed), but within a short time frame (e.g., within 24 hours) prior to or subsequent to administration of a lysosomal enzyme. In some embodiments, a therapeutic agent can be administered separately (e.g., not admixed), and without any prior, concurrent, or subsequent administration of a lysosomal enzyme. A synergistic effect may support reduced dosing of ERT when used with a therapeutic agent and a reduced dosing of the therapeutic agent.

Some embodiments are directed to a method of treating cytoplasmic glycogen storage disorder in an individual in need thereof comprising administering to the individual a therapeutically effective amount of a lysosomal enzyme, wherein the lysosomal enzyme is administered at a first higher therapeutically effective dose weekly until a desired response is reached and then the lysosomal enzyme is administered at a second lower therapeutically effective dose at a regular interval. In some embodiments, the first higher therapeutically effective dose is about 40 mg/kg to about 100 mg/kg. In some embodiments, the second lower therapeutically effective dose is about 20 mg/kg to about 80 mg/kg. In some embodiments, the regular interval is selected from bimonthly, monthly, biweekly, weekly, twice weekly, daily, twice a day, three times a day, or more often a day.

In some embodiments, the method further comprises pretreating the individual with an immune modulator prior to administration of the lysosomal enzyme. In some embodiments, the individual being treated does not have a significant amount of fibrosis. In some embodiments, the individual being treated does not have a significant amount of fibrosis in the liver. In some embodiments, the individual being treated does not have a significant amount of fibrosis in the liver, skeletal muscle, heart, brain, or a combination thereof.

In some embodiments, the compositions may be formulated with a physiologically acceptable carrier or excipient to prepare a pharmaceutical composition. Suitable pharmaceutically acceptable carriers may include, but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations may, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In some embodiments, a water-soluble carrier suitable for intravenous administration may be used.

The composition or medicament, if desired, may also contain minor amounts of wetting or emulsifying agents, or pH buffering agents. In some embodiments, the composition may be a liquid solution, suspension, emulsion, tablet, pill, capsule, sustained release formulation, or powder. In some embodiments, the composition may also be formulated as a suppository, with traditional binders and carriers such as triglycerides. Oral formulation may include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration may be a solution in sterile isotonic aqueous buffer. In some embodiments, the composition can also include a solubilizing agent and a local anesthetic to ease pain at the site of the injection. In some embodiments, the ingredients may be supplied either separately or mixed together in unit dosage form, for example, as a dry lyophilized powder or water free concentrate in a hermetically sealed container, such as an ampule or sachette indicating the quantity of active agent. In some embodiments, where the composition is to be administered by infusion, it may be dispensed with an infusion bottle containing sterile pharmaceutical grade water, saline or dextrose/water. In some embodiments, where the composition is administered by injection, an ampule of sterile water for injection or saline can be provided so that the ingredients may be mixed prior to administration.

According to some embodiments, a method of treating a steatosis-associated disorder comprises administering a therapeutically effective amount of a lysosomal enzyme. Some embodiments provide for a method of treating a cytoplasmic glycogen storage disorder comprising administering an adjunctive therapy comprising a therapeutic agent of embodiments herein to enhance efficacy of a lysosomal enzyme. In some embodiments, the lysosomal enzyme is administered as part of a lysosomal enzyme replacement therapy. In some embodiments, the therapeutically effective amount of the lysosomal enzyme (e.g. GAA) is about 1 mg/kg to about 100 mg/kg, about 1 mg/kg to about 75 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 5 mg/kg to about 100 mg/kg, about 5 mg/kg to about 75 mg/kg, about 5 mg/kg to about 60 mg/kg, about 5 mg/kg to about 50 mg/kg, about 5 mg/kg to about 40 mg/kg, about 5 mg/kg to about 30 mg/kg, about 5 mg/kg to about 20 mg/kg, about 10 mg/kg to about 100 mg/kg, about 10 mg/kg to about 75 mg/kg, about 10 mg/kg to about 60 mg/kg, about 10 mg/kg to about 50 mg/kg, about 10 mg/kg to about 40 mg/kg, about 10 mg/kg to about 30 mg/kg, about 10 mg/kg to about 20 mg/kg, less than about 100 mg/kg, less than about 75 mg/kg, less than about 60 mg/kg, less than about 50 mg/kg, less than about 40 mg/kg, less than about 30 mg/kg, less than about 25 mg/kg, less than about 20 mg/kg, less than about 15 mg/kg, less than about 10 mg/kg, less than about 5 mg/kg, or a range between any two of these values. In some embodiments, the effective dosage may be about 20 mg/kg, about 25 mg/kg, about 30 mg/kg, about 40 mg/kg, about 45 mg/kg, about 50 mg/kg, about 60 mg/kg, about 70 mg/kg, about 80 mg/kg, about 90 mg/kg, about 100 mg/kg, or a range between any two of these values. In some embodiments, the effective dose for a particular individual may be varied (e.g., increased or decreased) over time, depending on the needs of the individual. For example, in times of physical illness or stress, or if anti-enzyme antibodies become present or increase, or if disease symptoms worsen, the amount may be increased. As another example, an increased effective dose may be administered (perhaps weekly) initially to clear the glycogen load before administering a reduced effective dosage. In some embodiments, the type of lysosomal enzyme delivered may be varied over time, depending on the needs of the individual. For example, initially, a more potent form of GAA may be administered (e.g. neo-GAA or reveglucosidase) followed by administration of a less potent but perhaps more cost-effective GAA type (e.g. rhGAA).

In embodiments, a therapeutically effective amount of the lysosomal enzyme (or composition or medicament containing the lysosomal enzyme) may be administered at regular intervals, depending on the nature and extent of the disease's effects, and on an ongoing basis. Administration at a "regular interval," as used herein, indicates that a therapeutically effective amount is administered periodically (as distinguished from a one-time dose). The interval can be determined by standard clinical techniques. In some embodiments, the lysosomal enzyme's periodic administrations may be bimonthly, monthly, biweekly, weekly, twice weekly, daily, twice a day, three times a day, or more often a day. The administration interval for a single individual need not be a fixed interval, but can be varied over time, depending on the needs of the individual. For example, in times of physical illness or stress, if anti-enzyme antibodies become present or increase, or if disease symptoms worsen, the interval between doses may be decreased. In some embodiments, a therapeutically effective amount of the lysosomal enzyme at an amount of about 40 mg/kg body weight may be administered weekly. In some embodiments, a therapeutically effective amount of the lysosomal enzyme at an amount of about 20 mg/kg body weight may be administered twice weekly. In some embodiments, a therapeutically effective amount of the lysosomal enzyme at an amount of about 45 mg/kg body weight may be administered weekly. In some embodiments, a therapeutically effective amount of the lysosomal enzyme at an amount of about 22.5 mg/kg body weight may be administered twice weekly. In some embodiments, a therapeutically effective amount of the lysosomal enzyme at an amount of about 10 mg/kg body weight may be administered weekly. In some embodiments, a therapeutically effective amount of the lysosomal enzyme at an amount of about 5 mg/kg body weight may administered twice weekly.

In some embodiments, a lysosomal enzyme may be administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or a range between any two of these values. In some embodiments, a lysosomal enzyme may be administered at least once every 1, 2, 3, 4, 5, 6, 7, 8, 9, 10, 11, 12, 13, 14, 15, 16, 17, 18, 19, 20 weeks, or a range between any two of these values. In some embodiments, a lysosomal enzyme may be administered using single or divided doses of every 60, 48, 36, 24, 12, 8, 6, 4, or 2 hours, or a range between any two of these values, or a combination thereof. For example, in some embodiments, a lysosomal enzyme, functional equivalent thereof, or gene may be administered once every about one to about two, about two to about three, about three to about four, or about four to about five weeks.

In some embodiments, the acid alpha-glucosidase is administered bimonthly, monthly, biweekly, weekly, twice weekly, daily, twice a day, three times a day, or more often a day. In some embodiments, the acid alpha-glucosidase is administered in a therapeutically effective amount. In some embodiments, the therapeutically effective amount is about 1 mg/kg to about 50 mg per kg bodyweight of the individual. In some embodiments, the lysosomal enzyme may be administered in a higher dose initially to clear the glycogen load before administering the lysosomal enzyme.

In some embodiments, a therapeutic agent may be periodically administered. In some embodiments, periodic administration of the therapeutic agent may be bimonthly, monthly, biweekly, weekly, twice weekly, daily, twice a day, three times a day, or more often a day. In some embodiments, the therapeutic agent may be administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or a range between any two of these values. In some embodiments, the therapeutic agent may be administered at least once every 1, 2, 3, 4, 5, 6, 7, 8, 9, 10, 11, 12, 13, 14, 15, 16, 17, 18, 19, 20 weeks, or a range between any two of these values. In some embodiments, the therapeutic agent may be administered using single or divided doses of every 60, 48, 36, 24, 12, 8, 6, 4, or 2 hours, or a range between any two of these values, or a combination thereof. For example, in some embodiments, the therapeutic agent may be administered once every about one to about two, about two to about three, about three to about four, or about four to about five weeks.

In some embodiments, an autophagy-inducing agent may be administered prior to, or concurrently with, or shortly thereafter, the lysosomal enzyme, functional equivalent thereof or gene encoding such enzyme. In some embodiments, the autophagy-inducing agent may be administered sufficiently prior to administration of the lysosomal enzyme so as to permit modulation (e.g., up-regulation) of the target cell surface receptors to occur, for example, at least about two to about three days, about three to about four days, or about four to about five days before the lysosomal enzyme is administered. For example, in some embodiments, the autophagy-inducing agent may be administered to a patient about 0.25, 0.5, 1, 2, 3, 4, 5, 6, 7, 8, 9, 10, 11 or 12 hours, or 1, 2, 3, 4, 5, 6, 7, 8 days, prior to administration of a lysosomal enzyme or a functional equivalent thereof.

In some embodiments, a lysosomal enzyme may be formulated as neutral or salt forms. Pharmaceutically acceptable salts may include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In some embodiments, a therapeutic agent (or composition or medicament containing the therapeutic agent) is administered by an appropriate route. The therapeutic agent of embodiments herein may be administered by any suitable route, including administration by inhalation or insufflation (either through the mouth or the nose) or oral, sublingual, buccal, parenteral, topical, subcutaneous, intraperitoneal, intravenous, intrapleural, intraoccular, intraarterial, rectal administration, or within/on implants, e.g., matrices such as collagen fibers or protein polymers, via cell bombardment, in osmotic pumps, grafts comprising appropriately transformed cells, etc. In one embodiment, the therapeutic agent may be administered intravenously. In other embodiments, the therapeutic agent may be administered by direct administration to a target tissue, such as heart or muscle (e.g., intramuscular). In yet another embodiment, the therapeutic agent is administered orally. More than one route can be used concurrently, if desired.

In some embodiments, the lysosomal enzyme (or composition or medicament containing the lysosomal enzyme) is administered by an appropriate route. The therapeutic agents of embodiments herein may be administered by any suitable route, including administration by inhalation or insufflation (either through the mouth or the nose) or oral, sublingual, buccal, parenteral, topical, subcutaneous, intraperitoneal, intravenous, intrapleural, intraoccular, intraarterial, rectal administration, or within/on implants, e.g., matrices such as collagen fibers or protein polymers, via cell bombardment, in osmotic pumps, grafts comprising appropriately transformed cells, etc. In one embodiment, the lysosomal enzyme may be administered intravenously. In other embodiments, the lysosomal enzyme may be administered by direct administration to a target tissue, such as heart or muscle (e.g., intramuscular). In yet another embodiment, the lysosomal enzyme is administered orally. More than one route can be used concurrently, if desired.

In some aspects of the invention, a therapeutic agent is administered in combination with a second therapeutic agent or treatment, and in such cases, the therapeutic agents or treatments may be administered concurrently or consecutively in either order. For concurrent administration, the therapeutic agents may be formulated as a single composition or as separate compositions. The optimal method and order of administration of the therapeutic agents and a second therapeutic agent or treatment can be ascertained by those skilled in the art using conventional techniques and in view of the information set out herein.

The disclosed combination therapies may elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of the therapeutic agents when they are used in combination.

Where a combination therapy is used, in some embodiments, administration of the autophagy-inducing agent and the lysosomal enzyme can take place once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or at least once every 1, 2, 3, 4, 5, 6, 7, 8, 9, 10, 11, 12, 13, 14, 15, 16, 17, 18, 19 or 20 weeks, any range of two of these values, or any combination thereof, using single or divided doses of every 60, 48, 36, 24, 12, 8, 6, 4, or 2 hours, or any combination thereof.

In some embodiments, the autophagy-inducing agent (e.g. $\beta 2$ agonist) is administered prior to, or concurrently with, or shortly thereafter, the lysosomal enzyme, functional equivalent thereof or gene encoding such enzyme. In some embodiments, the autophagy-inducing agent may be administered sufficiently prior to administration of the lysosomal enzyme so as to permit modulation (e.g., up-regulation) of the target cell surface receptors to occur, for example, at least two-three, three-four or four-five days before the lysosomal enzyme is administered. For example, in some embodiments, the autophagy-inducing agent may be administered to a patient about 0.25, 0.5, 1, 2, 3, 4, 5, 6, 7, 8, 9, 10, 11 or 12 hours, or 1, 2, 3, 4, 5, 6, 7, 8 days, prior to administration of the lysosomal enzyme, recombinant version thereof, or a functional equivalent thereof.

In some embodiments, the lysosomal enzyme and the autophagy-inducing agent of embodiments herein may be formulated into a composition or medicament for treating the steatosis-associated disorders of embodiments herein. In some embodiments, the lysosomal enzyme and a therapeutic agent of embodiments herein may be formulated into a composition or medicament for treating the cytoplasmic glycogen storage diseases of embodiments herein. Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In some embodiments, a water-soluble carrier suitable for intravenous administration is used.

In some embodiments, a therapeutic agent may be administered prior to, or concurrently with, or shortly thereafter, the lysosomal enzyme, functional equivalent thereof or gene encoding such enzyme. In some embodiments, a therapeutic agent may be administered sufficiently prior to administration of the lysosomal enzyme so as to permit modulation (e.g., up-regulation) of the target cell surface receptors to occur, for example, at least about two to about three days, about three to about four days, or about four to about five days before the lysosomal enzyme is administered. For example, in some embodiments, a therapeutic agent may be administered to a patient about 0.25, 0.5, 1, 2, 3, 4, 5, 6, 7, 8, 9, 10, 11 or 12 hours, or 1, 2, 3, 4, 5, 6, 7, 8 days, prior to administration of acid alpha-glucosidase enzyme, modified acid alpha-glucosidase or a functional equivalent thereof.

In some embodiments, a therapeutic agent (e.g. $\beta 2$ agonist) is administered prior to, or concurrently with, or shortly thereafter, the lysosomal enzyme, functional equivalent thereof or gene encoding such enzyme. In some embodiments, the therapeutic agent capable of increasing expression of a receptor for a lysosomal enzyme may be administered sufficiently prior to administration of the lysosomal enzyme so as to permit modulation (e.g., up-regulation) of the target cell surface receptors to occur, for example, at least two-three, three-four or four-five days before the lysosomal enzyme is administered. For example, in some embodiments, the $\beta 2$ agonist may be administered to a patient about 0.25, 0.5, 1, 2, 3, 4, 5, 6, 7, 8, 9, 10, 11 or 12 hours, or 1, 2, 3, 4, 5, 6, 7, 8 days, prior to administration of GAA, modified acid alpha-glucosidase or a functional equivalent thereof.

In some embodiments, the composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

In some embodiments, the composition or medicament may be formulated in accordance with the routine procedures as a pharmaceutical composition adapted for administration to human beings. For example, in some embodiments, a composition for intravenous administration typically is a solution in sterile isotonic aqueous buffer. In some embodiments, the composition may also include a solubilizing agent and a local anesthetic to ease pain at the site of the injection. In some embodiments, the ingredients are supplied either separately or mixed together in unit dosage form, for example, as a dry lyophilized powder or water free concentrate in a hermetically sealed container such as an ampule or sachette indicating the quantity of active agent. In some embodiments, where the composition is to be administered by infusion, the composition can be dispensed with an infusion bottle containing sterile pharmaceutical grade water, saline or dextrose/water. In some embodiments, where the composition is administered by injection, an ampule of sterile water for injection or saline can be provided so that the ingredients may be mixed prior to administration.

The present disclosure is directed to the administration of a lysosomal enzyme, such as GAA to reduce lysosomal glycogen in patients having a cytoplasmic glycogen storage disease, and ultimately also reduce cytoplasmic glycogen. Some of the administered GAA may go directly into the cytosol and reduce glycogen. Moreover, the development of high sustained antibody titers to rhGAA in most patients with Pompe disease has negatively impacted the therapeutic outcome including decreased efficacy and life threatening allergic responses. Such an outcome is unlikely to happen to the patients with GSD III and GSD IV because these patients express normal levels of GAA. Accordingly, the present disclosure is directed to method of treating cytoplasmic glycogen storage diseases comprising administering a lysosomal enzyme, a functional equivalent thereof, or gene therapy therewith. In some embodiments, the lysosomal enzyme may be administered in conjunction with another therapeutic or an agent that increases the efficacy or delivery of the lysosomal enzyme. In some embodiments, the lysosomal enzyme may be administered with a β2 agonist. In some embodiments, the lysosomal enzyme may be administered with an immune modulator. In some embodiments, the lysosomal enzyme may be administered with an agent to prevent hypoglycemia (e.g. cornstarch).

There are a number of enzymes involved in the synthesis and breakdown of glycogen within the body. Deficiency or dysfunction of one of these enzymes results in a group of diseases called glycogen storage diseases (GSDs), in which the clinical hallmark is excessive glycogen accumulation in various tissues. One such GSD is PRKAG2 cardiomyopathy, which is caused by mutations in the PRKAG2 gene that encodes the γ2 subunit of AMP-activated protein kinase (AMPK). AMPK is a crucial cellular energy sensor that regulates a number of vital cellular metabolic cascades and lipid/glucose metabolic pathways.

PRKAG2 cardiomyopathy is an autosomal dominant disorder with a wide spectrum of disease. The syndrome is characterized by severe infantile hypertrophic cardiomyopathy and heart rhythm disturbances at one end to cases with later presentation (age range 8 to 42 years of age) and cardiac manifestations such as increased left ventricular wall thickness and ventricular preexcitation. Other features of the disease include glycogen accumulation in skeletal muscle and the clinical spectrum of muscle involvement is being better understood with time. The underlying mechanism of excess glycogen accumulation in PRKAG2 cardiomyopathy is illustrated in FIG. 45.

Figure 45:
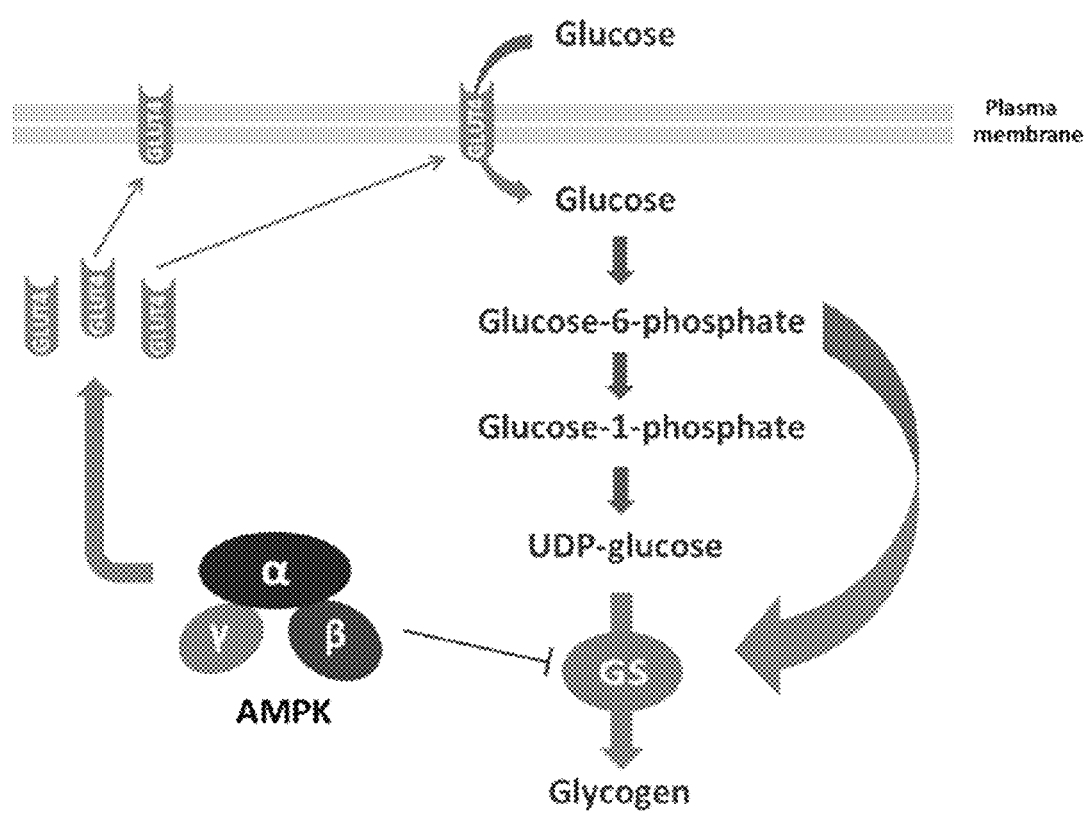
FIG. 45 illustrates the schematic mechanism of AMPK-mediated increase in cardiac and skeletal muscle glycogen accumulation in PRKAG2 deficiency. Mutations in the PRKAG2 gene, which encodes the regulatory γ2 subunit, cause chronic activation of AMPK. Elevated AMPK activity promotes glucose transporter 4 (GLUT4) shuttling to the plasma membrane and increases glucose uptake and intracellular glucose 6-phosphate (G6P) concentration. This leads to an allosteric activation of glycogen synthase (GS), which overrides the inhibitory effect of AMPK on GS, resulting in a net increase in GS activity and excess glycogen storage in muscle cells.

As shown in FIG. 45, mutations in the PRKAG2 gene, which encodes the regulatory γ2 subunit, cause chronic activation of AMPK. Elevated AMPK activity promotes glucose transporter 4 (GLUT4) shuttling to the plasma membrane and thus induces glucose uptake and increases intracellular glucose 6-phosphate (G6P) concentration. This leads to an allosteric activation of glycogen synthase (GS), which overrides the inhibitory effect of AMPK on GS, resulting in a net increase in GS activity and excess cytoplasmic glycogen storage in cardiac muscle cells.

The clinical features of PRKAG2 cardiomyopathy closely resemble the cardiac manifestations of Pompe Disease (GSD Type II). Pompe disease is an autosomal recessive metabolic disorder that is characterized by the glycogen accumulation in lysosomes of cardiac, skeletal, and smooth muscles due to the deficiency of the lysosomal enzyme acid alpha-glucosidase (GAA). With the phenotypic similarity of PRKAG2 cardiomyopathy to Pompe disease, there is the potential for a misdiagnosis for either of these disorders, especially the infantile form of Pompe disease. Due to similar symptomatic phenotypes, rare PRKAG2 cases can be misdiagnosed with infantile Pompe disease. PRKAG2 should be considered in the differential diagnosis of cases with cardiomyopathy.

In the past, the diagnosis of Pompe disease was confirmed using GAA enzyme measurements in cultured fibroblasts or muscle cells. Enzyme measurement using acarbose, an inhibitor of alpha-glucosidase, can greatly improve the sensitivity and specificity of Pompe disease diagnosis in blood and has now been adapted in many labs as a rapid way to diagnose Pompe disease. However, without the addition of acarbose, there may be false positive results and thus, it needs to be done in labs with experience and expertise. It is believed that the diagnostic measures should be broadened to include additional tests outside of enzyme testing in dried blood spots (DBS), such as gene sequencing and measurement of GAA activity in other tissues such as skin and muscle prior to initiation of ERT.

While the present disclosure is described in detail with reference to GSD-III or GSD-IV, the methods described herein may also be used to treat individuals suffering from other GSDs, including, but not limited to glycogen storage disease type I (e.g. GSD I), glycogen storage disease III (GSD III), glycogen storage disease IV (GSD IV), glycogen storage disease V (GSD V), glycogen storage disease VI (GSD VI), glycogen storage disease VII (GSD VII), glycogen storage disease IX (GSD IX), glycogen storage disease XI (GSD XI), glycogen storage disease XII (GSD XII), glycogen storage disease XIII (GSD XIII), glycogen storage disease XIV (GSD XIV) (phosphoglucomutase deficiency), Danon disease (GSD 2B, LAMP-2 deficiency), Lafora disease, or conditions associated with protein kinase gamma subunit 2 (PRKAG2)-deficiency. In some embodiments, GSD III may be selected from GSD type IIIa, type IIIb, type IIIc, or type IIId.

While embodiments set forth herein are described in terms of "comprising", all of the foregoing embodiments also include compositions and methods that consist of only the ingredients or steps recited or consist essentially of the ingredients and steps recited, and optionally additional ingredients or steps that do not materially affect the basic and novel properties of the composition or method.

This disclosure and embodiments illustrating the method and materials used may be further understood by reference to the following non-limiting examples.

Example 1

In Vitro Testing of Compounds

The role of autophagy in GSD Ia has been carried out in G6pase-deficient mice. A Western blot analysis for the autophagy marker protein LC3 was performed to ascertain the status of autophagy in G6pase-deficient mice. This analysis took advantage of the fact that Cytosolic LC3 (LC3-I) is lipidated and inserted into the autophagosomal membrane, forming LC3-II when autophagosomes are formed. Thus, the ratio of LC3-II to actin or other housekeeping genes can be used as a marker of autophagy. A decrease in hepatic LC3-II protein was observed in G6Pase-deficient mice (FIG. 1A), indicating that loss of G6Pase leads to a down-regulation of autophagy.

Figure 1B:
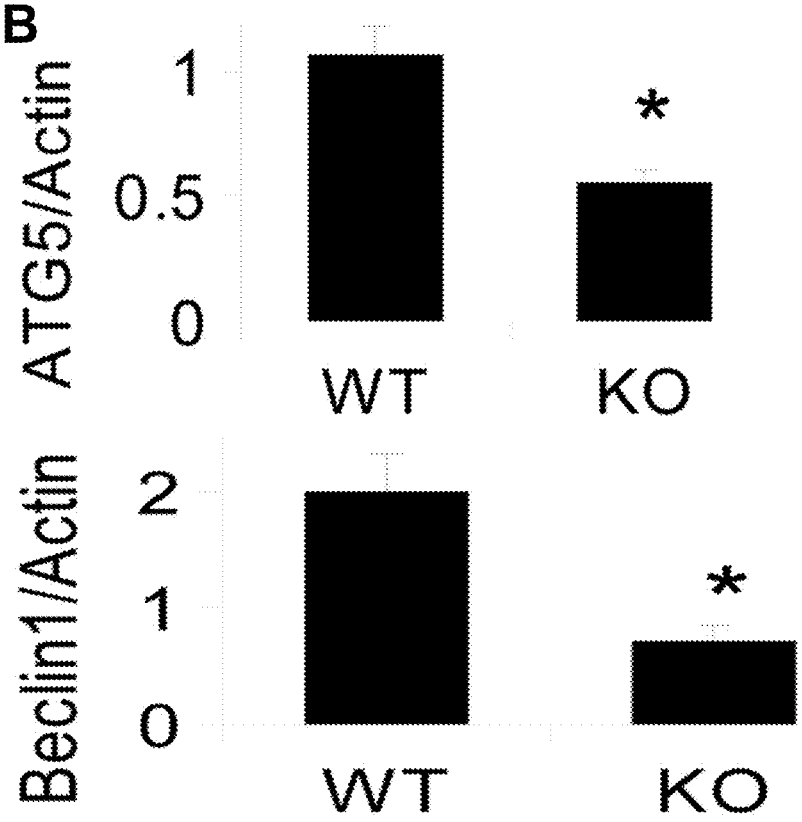
FIG. 1B illustrates that key autophagy related proteins, ATG5 and Beclin-1, are downregulated in G6Pase (−/−) mice (n=3 per group). Mean +/− SEM. Asterisk represents $p<0.05$.

Chronic stimulation also may lead regulation of autophagy at the transcriptional level. Accordingly, the levels of key ATG proteins were ascertained. Beclin-1 is a key member of the Class III PI3K complex, which is necessary for initiating autophagy. It was found that there is less Beclin-1 present in the livers of mice deficient in G6Pase (FIG. 1B). ATG5, which plays a key role in the elongation of autophagosomal membranes, is also decreased in these mice (FIG. 1B). Similar data for ATG5 and Beclin mRNA were observed (data not shown). Thus, besides a decrease in hepatic autophagy in G6pase (−/−) mice, the levels of autophagy proteins were also decreased, suggesting that long-term downregulation of autophagy in GSD Ia may occur via transcriptional mechanisms.

Figure 2A:
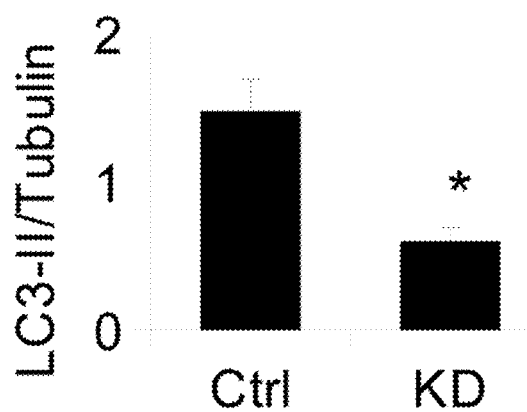
FIG. 2A illustrates LC3-II levels 96 hours after knockdown.
Figure 2B:
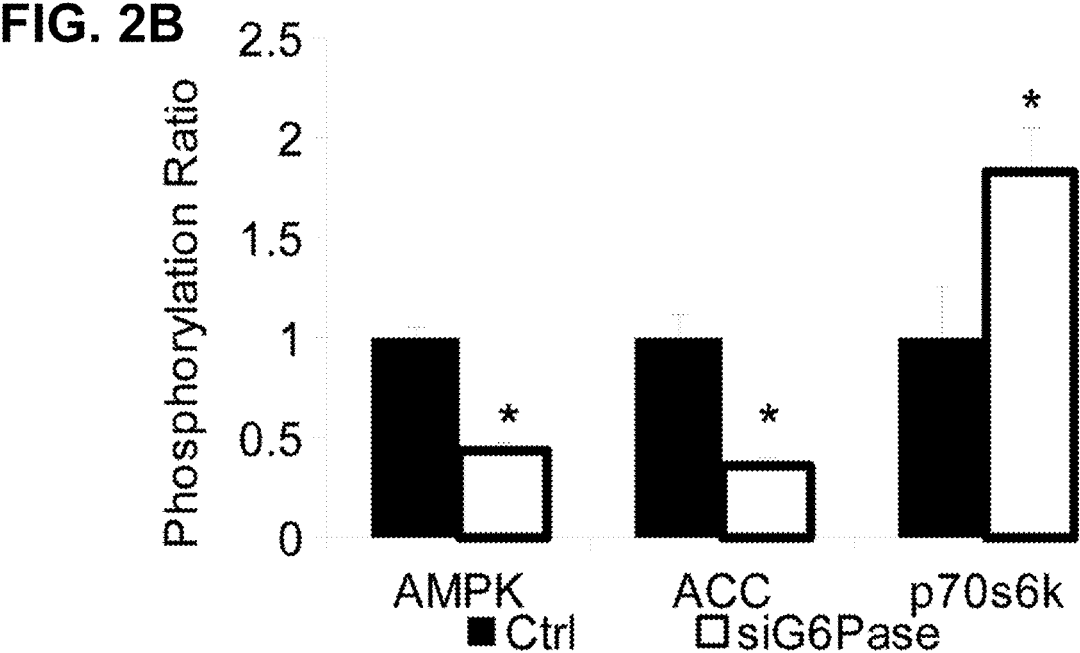
FIG. 2B illustrates changes in mTOR and AMPK pathways at this timepoint (n=3, asterisk represents $p<0.05$).
Figure 3A:
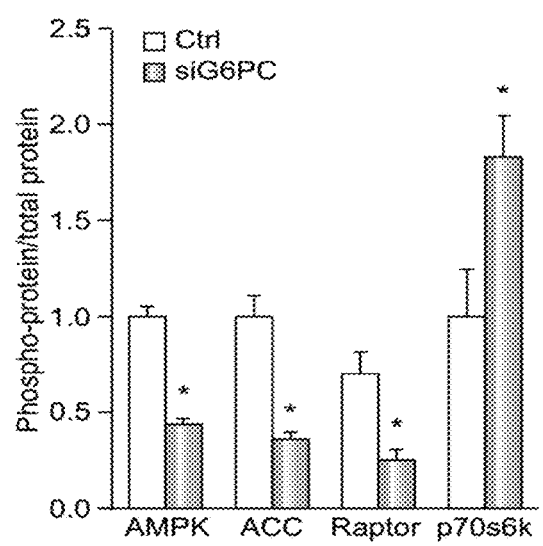
FIGS. 3A and 3B illustrate that the upstream pro-autophagic AMPK signaling pathway is downregulated (pAMPK, pRaptor and pACC levels), and the anti-autophagic mTOR pathway (p-p70s6k levels) is upregulated in AML-12 cells treated with siG6PC (FIG. 3A) and G6Pase-KO mice (FIG. 3B).
Figure 3B:
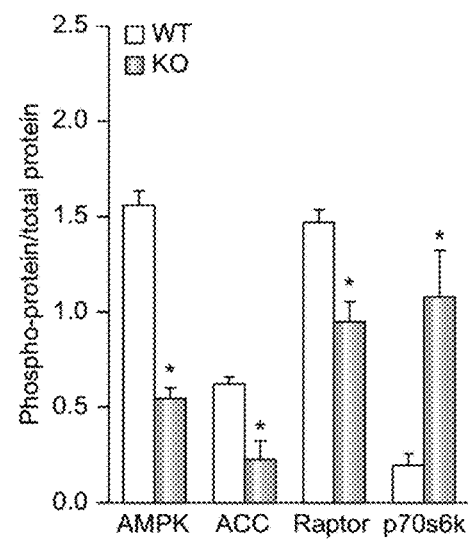
Figure 3C:
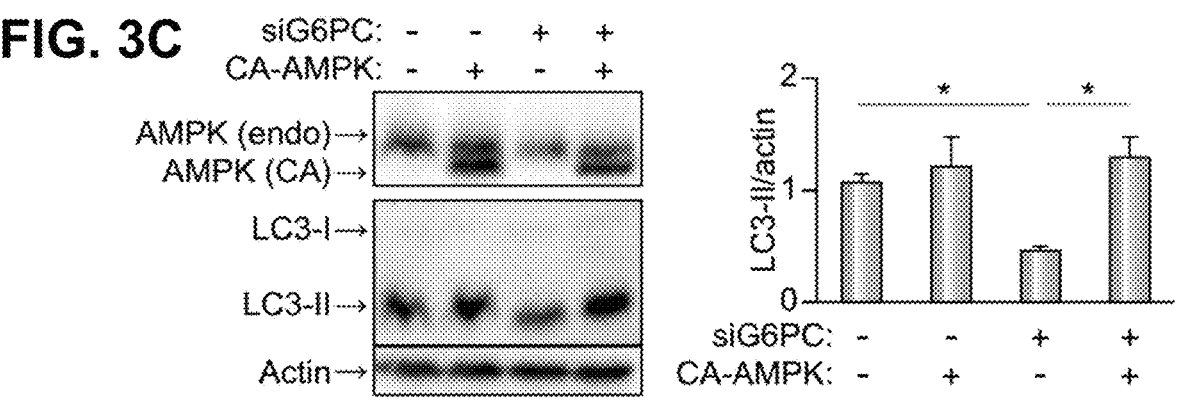
FIG. 3C illustrates that overexpression of constitutively active AMPK (CA-AMPK) in G6PC KD cells restores LC3-II levels. For all experiments shown n=3, *=$p<0.05$ between control and KD or KO groups, error bars represent SEM.
Figures 5A, 5B, 5C, 5D, 5E:
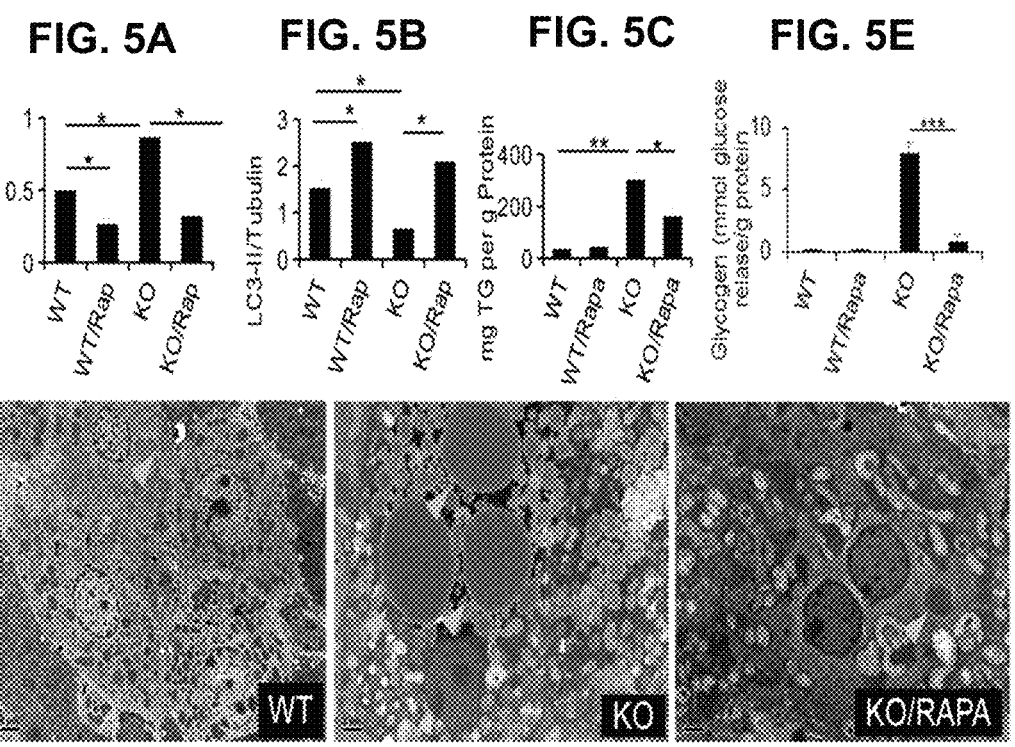
FIG. 5A illustrates p70s6k phosphorylation.
FIG. 5B illustrates LC3-II protein levels.
FIG. 5C illustrates hepatic TG levels.
FIG. 5D illustrates representative hepatic electron micrographs at 3000×. Green arrowhead represents lipid droplets.
FIG. 5E illustrates glycogen content. For all parts: n=4 or 5 mice per group, asterisk represents p<0.05, two asterisks represent p<0.01.
Figure 6:
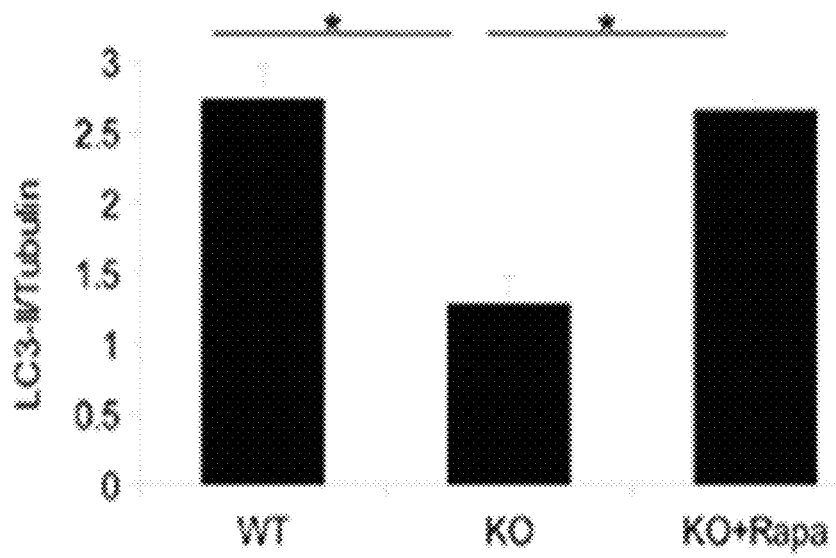
FIG. 6 illustrates the induction of autophagy in kidneys of G6Pase-KO mice. Treatment of G6Pase-KO mice for 1 week with rapamycin increased autophagosome content in the kidney. *=p<0.05.

This data regarding G6Pase deficiency were validated in cell culture studies. ANIL-12 murine hepatic cells were transfected with siRNA against G6Pase (siG6Pase) for 96 hours to knockdown ("KD") G6Pase, and lipid accumulation and autophagy were assayed. At this time point, LC3-II levels were decreased (FIG. 2A). The MTOR and AMPK pathways were investigated to determine which upstream pathways were potentially responsible for the autophagy deficit. Loss of G6Pase led to a decrease in active (phosphorylated) AMPK, as well as a decrease in phosphorylated ACC, its downstream target. Furthermore, an increase in phosphorylated p70s6k, a marker for mTORC1 activity was also noted (FIG. 2B and FIG. 3A). Both of these changes in cellular signaling are believed to play a role in reducing autophagy. G6Pase-KO mouse livers also showed a decrease in AMPK and an increase in mTOR pathway activities (FIG. 3B), suggesting that both pathways may contribute to suppression of autophagy in GSDIa. Furthermore, restoration of AMPK signaling by overexpression of a previously described constitutively active AMPK construct led to restoration of autophagy in G6PC KD cells (FIG. 3C). In addition, imaging studies revealed lipid accumulations in siG6Pase-treated AML-12 cells both by fluorescence (FIG. 4A) and by electron microscopy (FIG. 4B), similar to lipid accumulations present in G6Pase-KO mouse liver (FIG. 5). These results indicate that KD of G6Pase in AML12 cells with siG6Pase can re-capitulate the abnormalities of GSD Ia in an in vitro system Candidate drugs for restoring autophagy in the GSD Ia liver were evaluated. Rapamycin is known to both have potent effects on activating autophagy as an mTORC1 inhibitor, and to regulate lipid metabolism due to its effect upon mTORC1. GSD Ia mice were treated with rapamycin daily for 7 days prior to evaluating effects upon autophagy and lipid accumulation in the liver. This Rapamycin treatment decreased phosphorylation of the mTOR substrate p70s6k, a result consistent with inhibition of mTORC1 (FIG. 5A). Furthermore, LC3-II was increased (FIG. 5B), which is consistent with activation of autophagy, and an equivalent effect was observed in the kidneys of G6Pase-KO mice (FIG. 6). In addition, rapamycin reduced triglycerides in the GSD I liver, suggesting that activation of autophagy could be beneficial in the fatty liver (FIGS. 5C-5D). Importantly, rapamycin reduced glycogen content in the GSDIa liver almost as low as that observed in wildtype mouse liver (FIG. 5E).

The effect of rapamycin was further evaluated in dogs with GSDIa that were treated with AAV-G6Pase to promote survival and prevent hypoglycaemia. Dogs with GSDIa had significantly reduced autophagy in the liver, in comparison with unaffected carrier dogs (FIG. 7A). Dogs had residual hepatomegaly despite treatment with AAV-G6Pase, which was significantly reduced (FIG. 7B) following 1 week of daily oral rapamycin administration (1 mg/kg/day). Serum GGT was significantly decreased (FIG. 7C) following rapamycin, indicating reduced hepatocellular damage from GSDIa. These data supported a beneficial effect from stimulating autophagy in the large animal model for GSDIa.

To determine the mechanisms for abnormal autophagy, the cell signaling cascades in the livers of mice lacking functional G6Pase will be studied. The mTORC1 and AMPK pathways will be studied because these pathways are critical for the initiation of autophagy through regulation of phosphorylation of ULK1 protein, a key component of the early autophagasome. It will also be determined how these pathways have been dysregulated in GSD Ia. The effects on the downstream metabolites will also be examined by utilizing the Metabolomics Core Facility at Duke-NUS. The ER stress/UPR pathway, and the function of transcription factors known to induce autophagy, such as the FoxO family, will be investigated. Finally, the abnormalities detected in GSD Ia mouse livers will be evaluated in canine and human GSD Ia livers available under IACUC and IRB approved protocols at Duke University.

In vitro modeling of G6Pase deficiency: To further study the role of autophagy in the pathogenesis of GSD Ia, experiments in cell culture of hepatic cell lines (e.g., AML12) will be performed using both pharmacological and genetic approaches. Experiments using siRNA to knock down (KD) G6Pase in a cell culture model for GSD Ia have begun. Treating hepatic cells with the G6PT inhibitor S4048 may be a better acute model because G6Pase protein is long-lived, leading rapidly to the accumulation of G6P and onset of GSD Ia-like effects in cultured cells. It is possible to probe the acute effects on lipid/glycogen accumulation, autophagy, and upstream signaling pathways over longer periods of time in cell culture. G6Pase will be permanently knocked down in AML-12 cells, which are immortalized mouse hepatocytes that maintain much of the normal hepatic metabolic phenotype, to further examine the chronic effects of the loss of G6Pase on autophagy signaling. This work will allow the understanding how G6P accumulation leads to the derangements in cell signaling and autophagy, and will provide mechanistic insight into potential therapeutic targets. Furthermore, a comparison between the findings in cell culture and in vivo will enable the determination whether the effects of G6Pase knockdown are cell-autonomous, and can be modified by circulating factors or drugs.

TABLE 4

Treating G6pase (−/−) Mice with Drugs that Enhance Autophagy

| Drug (class) | Effect |
|---|---|
| Bezafibrate (PPAR-α agonists) | Reduced steatosis, increased FAO |
| Caffeine | Increased autophagy, reduced steatosis |
| β2-agonists (clenbuterol) | Increased autophagy in liver (not shown) |
| Rapamycin (mTOR inhibitors) | Increased autophagy in GSDIa liver |
| Thyroid hormone | Increased autophagy, reduced steatosis |
| A-lipoic acid (AMPK activator) | Activated autophagy, reduced intercellular |
| Metformin (AMPK activator) | Activated autophagy, activated AMPK in vitro |
| Verapamil (Calcium channel | Induced autophagy, reduced cytosolic calcium |
| Trehalose (chemical | Stimulated autophagy |
| Carbamazepine (Intracellular inositol reduction) | Activated autophagy, reduced hepatosteatosis |
| Lithium Chloride (Intracellular inositol reduction) | Activated autophagy, reduced apoptosis and steatosis |
| Methylene blue (Sirtuin-1 activator) | Activated autophagy, inhibited hepatosteatosis |
| Resveratrol (Sirtuin-1 activator) | Enhanced FAO, reduced |
| Mifepristone sarnesoid X receptor suppressor) | Activated autophagy, inhibited FXR |

Manipulation of autophagy to investigate efficacy in vitro: Preliminary data has suggested that autophagy is deficient in GSD Ia. Also, findings have suggested that increasing hepatic autophagy may decrease hepatosteatosis and glycogen accumulation. Therefore, autophagy will be artificially induced to determine its therapeutic benefit in GSD Ia. Using the cell culture model generated above, compounds known to induce autophagy in human hepatic cells will be tested. Compounds such as mTOR inhibitors rapamycin, Torin1, and the AMPK activator AICAR, known to have potent effects on autophagy, will be investigated.

It will be examined whether β-oxidation of fatty acids can be increased with inhibition of pmTOR, or with activation of either pAMPK or PPAR-α using appropriate drugs (Table 4). One such drug is bezafibrate (200 µM), a pan-peroxisome proliferator that increased autophagosomes in cultured rat hepatocytes. Fatty acid β-oxidation (FAO) was increased by bezafibrate (400 µM) as indicated by increased carnitine palmitoyl transferase (CPT) activity in cultured cells, and reversed the effects of NAFLD in mice. The FAO/oxidative phosphorylation by metabolomic analysis of acylcarnitines in cell and liver extracts and Seahorse studies of oxygen consumption in vitro will be followed. These studies will enable the identification and understanding of the abilities of known autophagy inducers to improve the metabolic disorder in GSD Ia.

It is believed that G6Pase KD cells will demonstrate the abnormalities of autophagy observed in the G6pase (−/−) mouse liver, namely decreased LC3-II, Atg 5, and Beclin 1. Additionally, it is believed that accumulation of triglycerides will occur following G6Pase in vitro.

Example 2

In Vivo Testing of Compounds in Gsd Ia Mice

Clenbuterol was shown to induce autophagy in a murine model for hepatosteatosis (FIG. 5). Increasing concentrations of clenbuterol were capable of activating autophagy as indicated by observing increased LC3-II relative to action (FIGS. 5A-5B), and similarly increased LC3-II was observed in primary hepatocytes (FIG. 5C). Thus, clenbuterol, a long-acting β-agonist with proven safety for long-term treatment of mice, represents a leading candidate among drugs to be considered for the manipulation of autophagy in GSD Ia (Table 2).

The promising autophagy-inducing compounds of Example 1 will be tested in G6Pase (−/−) GSD Ia-model mice to determine their effects on the metabolic derangements of this disease. The mice also will be treated with the autophagy-inducing compound from 5 to 12 days of age. The fasting serum glucose, hepatic lipid and glycogen content, cell signaling pathways, metabolites, as well as hepatic autophagy will be examined. If a compound successfully ameliorates the abnormalities of GSD Ia, the fasting serum glucose should be increased in the treated animals, and the hepatic lipid and glycogen content should be reduced from their abnormally high levels. Thereafter, a successful compound will be evaluated in the high fat diet fed mouse model to evaluate its effects on diet-induced hepatosteatosis in wild-type mice.

Metabolomics provide noninvasive monitoring of therapeutic effects in GSD Ia: Blood and urine sampling will demonstrate the correction of biochemical abnormalities of GSD Ia by metabolomics. At 2, 6, and 12 months of age, mice will be fasted for 8 hours prior to collection of blood for monitoring glucose, which will demonstrate prevention of hypoglycaemia if gluconeogenesis has been increased by small molecule treatment. Metabolomics consisting of plasma acylcarnitines, amino acids, triglycerides, and lactate will be analyzed on fasting samples. GSD-Ia patients have elevated plasma lactate and urinary methylglutaconate, both of which can reflect mitochondrial dysfunction. Urine organic acids will be analyzed for lactate, methylglutaconate, and 3-hydroxybutyric acid by gas chromatography-mass spectrometry as described to detect changes in ketogenesis related to treatment. This panel of testing has revealed unique biomarkers among patients with diabetes, endorsing the selection of these tests for other carbohydrate disorders such as GSD Ia. Metabolomic monitoring will be critical to developing biomarkers to serve as surrogate markers for efficacy in an eventual clinical trial in GSD Ia.

Metabolomic analysis of hepatic extracts will be performed. Acylcarnitine and amino acid profiling will detect any changes related to increased lipolysis and fatty acid beta-oxidation following stimulation of autophagy in mice with hepatosteatosis.

Expected Outcomes: It is believed that elevations of markers for ER stress that are present in the G6pase (−/−) mouse liver will be elevated in G6Pase KD cells. Abnormalities detected in the murine GSD Ia liver should be present in canine and human GSD Ia liver samples, confirming the relevance of these abnormalities to GSD Ia in higher mammals. Effective small molecule therapies will reduce liver triglycerides through increasing autophagy, and the reversal of hepatosteatosis will improve the biochemical abnormalities of GSD Ia.

Metabolomics of blood and urine will reveal the correction of biochemical abnormalities, including hypoglycaemia, lactic acidemia and lactic aciduria, elevated urine ketones, and other biomarkers to be determined. Metabolomics of hepatic extracts will reveal increased long-chain acylcarnitines and decreased amino acids, as demonstrated following stimulation of lipolysis in mice with hepatosteatosis. The small molecule drug will activate autophagy and further normalize the metabolic derangements (particularly lipid) of GSD Ia through metabolomics detection and analyses.

Efficacious compounds will be evaluated in a murine model for NAFLD.

Example 3

Therapeutic Potential of Novel Candidate Drug Therapies in Conjunction with ERT to Correct GAA Deficiency in Mice with Pompe Disease In GAA-KO mice, ERT failed to correct glycogen storage in the skeletal muscle as evidenced by high residual levels of glycogen following standard of care ERT. The ability to directly study novel therapies in engineered human muscle will be of great future utility to Pompe disease research community. Initially, the in vitro human muscle model needs to be correlated with the validated GAA-KO mouse model.

Preliminary Results: Effective dosages for ERT in Pompe disease are up to 100-fold greater than those in other lysosomal disorders. This high-dose requirement has been attributed to the low abundance of cation-independent mannose-6-phosphate receptor (CI-MPR) in skeletal muscle (FIG. 9A). The impact of CI-MPR-mediated uptake of recombinant human (rh) acid-α-glucosidase (GAA) upon ERT has been evaluated in GAA knockout (KO) mice with Pompe disease. Clenbuterol, a selective β2 agonist, was revealed to enhance CI-MPR expression and increase efficacy from ERT, thereby demonstrating a key role of CI-MPR with regard to replacement therapy in Pompe disease. The clearance of stored glycogen was increased by β2-agonist treatment during ERT, as demonstrated by lower glycogen content in skeletal muscle following the addition of clenbuterol (FIG. 9B) or albuterol treatment. The skeletal muscles comprised primarily of type II myofibers responded more efficaciously to ERT when clenbuterol or albuterol therapy was added, including the tibialis anterior muscle. Type II muscles are resistant to ERT in association with low CI-MPR expression.

The availability of ERT has prolonged the survival of patients, which has increased the understanding of pathology and extent of disease in infantile Pompe disease. Even in patients with a good response to ERT, residual motor weakness (neck flexor weakness, dorsiflexor weakness, mypathic facies, ptosis and strabismus) has been observed. Autopsy of infantile patients has revealed glycogen accumulation in Purkinje cells of the cerebellum, neurons of the cerebral cortex, motor neurons of the spinal cord and in vascular smooth muscle cells of the CNS vasculature, all of which may contribute to the neurological deficits observed in these patients despite compliance with ERT. Correction of neuromuscular involvement and brain pathology has not been possible in Pompe disease, despite adherence to standard-of-care ERT. Our proof-of-concept data demonstrated that adjunctive β-agonist treatment with ERT reversed neuromuscular involvement in GAA-KO mice. The proposed clinical trial of clenbuterol with ERT will reveal how effectively β-agonist therapy increases CI-MPR expression and increases receptor-mediated uptake of rhGAA in Pompe disease.

β-agonist therapy should enhance the response to ERT in Pompe disease and other lysosomal storage disorders. Furthermore, increasing CI-MPR expression should reduce the dosage requirements for ERT or a future gene therapy. Adjunctive therapy with a β2 agonist, such as albuterol, has been shown to improve the 6 minute walk test performance in patients with late-onset Pompe disease. Overall, the availability of treatments that can prove efficacy of ERT for Pompe disease and other lysosomal storage disorders will improve efficacy and reduce the costs of therapies for these diseases.

Protocol: Recombinant human GAA (rhGAA) used in clinical practice will be obtained from Genzyme. Based on our preliminary studies in mice, the impact of adjunctive small molecule therapy upon ERT will be evaluated. Initial doses to be administered are shown in Table 4.

Evaluating the efficacy of alternative small molecule therapy and ERT in GAA-KO mice ERT is enhanced by the addition of a β2 agonist, clenbuterol, which was demonstrated to induce muscle hypertrophy and to increase the expression of CI-MPR in muscle and to increase the efficacy of ERT. Four other drugs will be administered to groups of GAA-KO mice at the dose anticipated to induce muscle hypertrophy (and increase the expression of CI-MPR, analogous to clenbuterol's effects). These drugs will be administered to groups of 3 month-old GAA-KO mice in drinking water (Table 5). In addition to the three alternative β2 agonists, dehydroepiandrosterone will be tested given its effect upon muscle strength and Igf-1 levels that are analogous to clenbuterol's effects. The dose-response for fenoterol and salmeterol has been equivalent to that for clenbuterol in previous rodent studies. Therefore the same dose for the former two drugs that has been established for clenbuterol will be used when administered in drinking water to mice. Groups of drug-treated GAA-KO mice and mock-treated GAA-KO mice will be analyzed as negative controls (n=8 per group).

TABLE 5

Small Molecule Therapies to be Evaluated in Combination with ERT or Gene Therapy

| Drug | Dose to induce muscle hypertrophy in combination with ERT (reference)[1] |
|---|---|
| Clenbuterol | 30 mg/l |
| Fenoterol | 30 mg/l |
| Formoterol | 4 mg/l |
| Salmeterol | 30 mg/l |
| Dehydroepiandrosterone | 250 mg/l |

[A]dministered in drinking water.

Efficacy will be evaluated by administering biweekly ERT (20 mg/kg rhGAA) to groups of 8 GAA-KO (or DKO) mice (4 male and 4 female). Rotarod testing, wirehang testing, ELISA, and urinary biomarker will be evaluated at 0, 4 and 8 weeks. Tissues will be analyzed at 8 weeks to evaluate (1) GAA activity and glycogen content in the heart, skeletal muscle, and brain; (2) glycogen staining for lysosomal accumulations; (3) Western blot detection of CI-MPR in striated muscles, liver, spleen, and brain; and (4) Western blot detection of hGAA in striated muscles, liver, spleen, and brain. The significance of differences between groups will be tested using a two-sided Wilcoxon rank sum test for continuous variables. A p-value <0.05 will be considered to be statistically significant.

Expected Results: The GAA-KO mice are expected to respond to treatment with the drugs listed in Table 5, because CI-MPR will be increased in skeletal muscle. The efficacy of ERT will be enhanced by the addition of the drugs, increasing biochemical correction and muscle function.

Example 4

Clenbuterol in Conjunction with ERT for GSD Ia

The therapeutic potential of clenbuterol in conjunction with ERT to reverse the glycogen storage and steatosis of GSD Ia will be investigated. Preliminary data revealed that ERT with recombinant human GAA reduced the stored glycogen in the liver of animals with GSD III. The potential of treatment with GAA to reverse glycogen storage in the liver and kidneys of mice with GSD Ia will be evaluated. Adjunctive therapy with clenbuterol will also be evaluated for its efficacy with ERT, because it both reduced hepatosteatosis and increased the uptake of rhGAA in preclinical experiments.

Purpose: These experiments will evaluate the feasibility of ERT with rhGAA for GSD Ia, based upon preliminary data that showed ERT could reduce cytoplasmic stores of glycogen.

Preliminary Results: rhGAA (Myozyme*; alglucosidase alfa), an FDA approved therapy for Pompe disease, significantly reduced glycogen levels in primary muscles from patients with GSD IIIa. The similarities between GSD Ia and GSD III with regard to accumulations of cytoplasmic glycogen in liver indicate that ERT with rhGAA could be effective in GSD Ia.

Protocol: This experiment will be performed in one week old G6pase (−/−) mice, administering ERT +/− clenbuterol. The fasting serum glucose, hepatic lipid and glycogen content, cell-signaling pathways, metabolites, as well as hepatic autophagy will be examined. If ERT +/− clenbuterol successfully ameliorates the abnormalities of GSD Ia, the fasting serum glucose will be increased in the treated animals, and the hepatic lipid and glycogen content will be reduced from their abnormally high levels.

Expected Results: Following ERT with rhGAA metabolomics of blood and urine will reveal the correction of biochemical abnormalities, including hypoglycaemia, lactic acidemia and lactic aciduria, elevated urine ketones, and other biomarkers to be determined. ERT is anticipated to lower liver and kidney glycogen content, and that adjunctive clenbuterol will increase this effect. Clenbuterol will have two beneficial effects: 1) increasing the receptor-mediated uptake of rhGAA in liver and kidney by upregulating CI-MPR, and 2) increasing autophagy to reduce hepatosteatosis.

Example 5

Phase 1 Clinical Trial Preparation for Candidate Drugs

A pilot clinical trial will be conducted with an adjunctive small molecule therapy showing the greatest promise in the GSD Ia mouse models. A Phase 1 clinical trial with albuterol in patients with Pompe disease has been conducted. The safety of treatment with new small molecule drugs will be evaluated in adult subjects with GSD Ia and Pompe disease. Subjects will start a low dose of drug, and then will be advanced to a higher dose after the 6 week follow-up visit, and will be monitored for 24 weeks.

Plan clinical translation of a new candidate drug for Pompe disease. A Phase I clinical trial of adjunctive drug therapy for late onset Pompe disease is planned. Candidate drug therapy will be combined with ERT during a year-long pilot study. Subjects will return for safety and efficacy monitoring after 6 and 12 weeks of drug therapy, and 12 weeks thereafter. The majority of patients with late-onset Pompe disease have a limited clinical response to ERT, and therefore ERT can be enhanced by upregulating CI-MPR to increase the receptor-mediated uptake of rhGAA. Therapeutic outcomes will be analyzed by comparing the muscle function, pulmonary function, and biochemical correction of muscle in subjects with late-onset Pompe disease treated with ERT, both prior to and during simultaneous β2 agonist therapy.

A clinical trial of new drug therapy in subjects with GSD Ia will be initiated, assessing appropriate clinical endpoints on a similar schedule to the clinical trials in Pompe disease.

Example 6

Use of Rapamycin to Induce Autophagy

The basis for endeavoring to adapt autophagic drug therapies to GSD Ia came from the symptomatic similarities between NAFLD and GSD Ia. NAFLD is characterized by lipid accumulation and hepatomegaly, and in its more severe forms also comprises fibrosis, cirrhosis, and hepatocellular carcinoma. GSD Ia livers likewise present lipid accumulation, hepatomegaly, fibrosis, and eventual hepatocellular carcinoma. Due to the striking similarities of some of the most common symptoms for both diseases and the chronic outcomes, we investigated whether recent advances in autophagy manipulation for NAFLD could be applied to our GSD Ia experimental models.

Figure 10A:
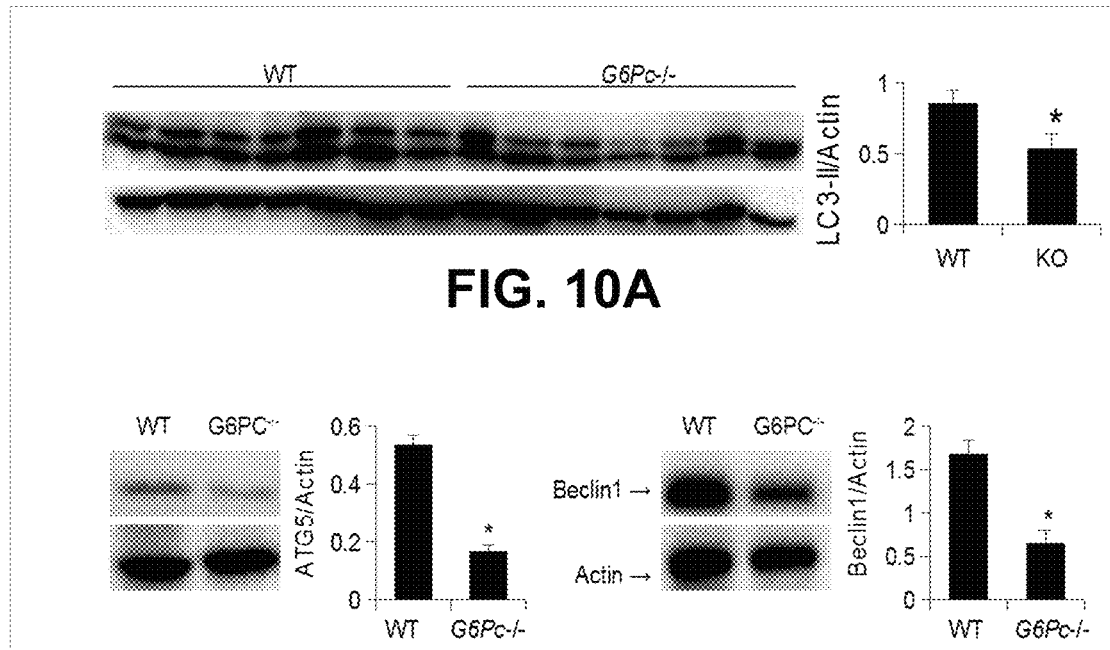
FIG. 10A Western blotting G6pc−/− mouse livers showed decreased LC3-II levels versus WT mice.
Figure 10B:
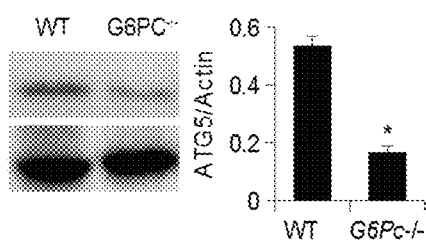
FIG. 10B ATG5 protein level is reduced in the livers G6pc KO mice.
Figure 10C:
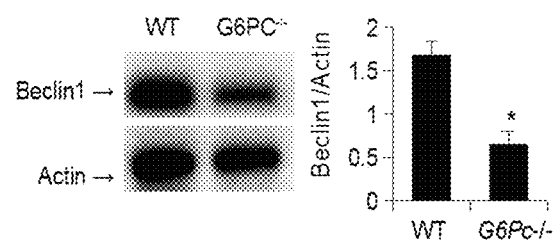
FIG. 10C Beclin 1 protein level is reduced in the livers of the same mice. For all experiments shown, n=3, except (FIG. 10A), where n=7, and * represents p<0.05 between experimental groups being compared. Error bars: SEM.
Figure 11:
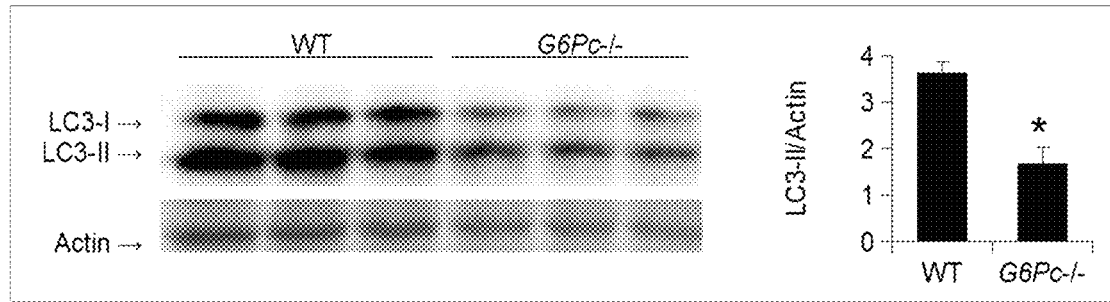
FIG. 11 illustrates LC3-II is reduced in GSD Ia mouse kidneys. Autophagosome number as indicated by LC3-II/actin ratio is decreased in the kidneys of G6pc KO mice. N=3, and * represents p<0.05 between experimental groups. Error bars: SEM.
Figure 12:
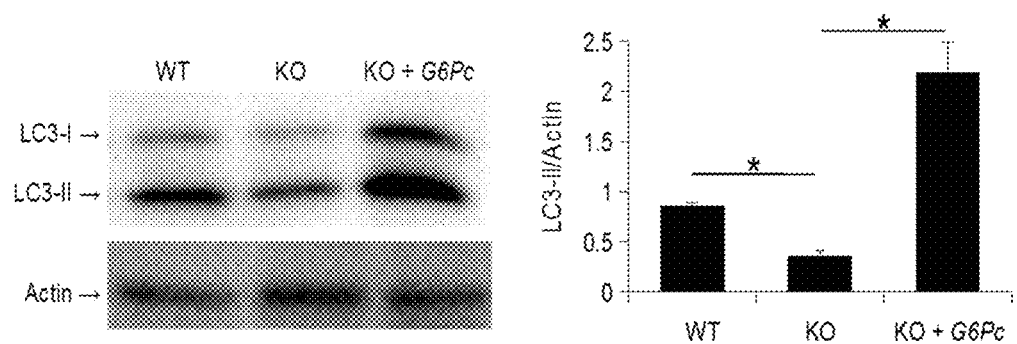
FIG. 12 illustrates AAV-G6Pase treatment prevents reduced autophagy in G6pc−/− mice. Treatment of KO mice with AAV2/9-G6Pase ("+G6Pc") restores autophagy. N=3, and * indicates p<0.05. Error bars: SEM.

First, since LC3-II is known to be diminished in NAFLD, we sought to confirm that it is likewise downregulated in GSD Ia. It was found that GSD Ia mice had reduced levels of LC3-II, a marker of autophagy, as well as reduced levels of the pro-autophagic proteins ATG5 and Beclin 1 (FIG. 10). LC3-II is also reduced in GSD Ia mouse kidneys, the kidney being the secondary organ affected by GSD Ia (FIG. 11). Finally, whether AAV treatment with G6PC transgene-carrying vectors prevents the autophagy deficiency was examined. It was found that providing the therapeutic benefits of a G6PC transgene does indeed reduce development of GSD Ia autophagy-related symptoms from developing (FIG. 12). This demonstrates that autophagy is indeed reduced in GSD Ia mice and is directly caused by G6pc deficiency, showing its relation to NAFLD symptoms and providing more support for our hypothesis that autophagy manipulation, which has benefits in NAFLD models, may provide new treatment routes for GSD Ia models and, eventually, patients.

Figure 13:
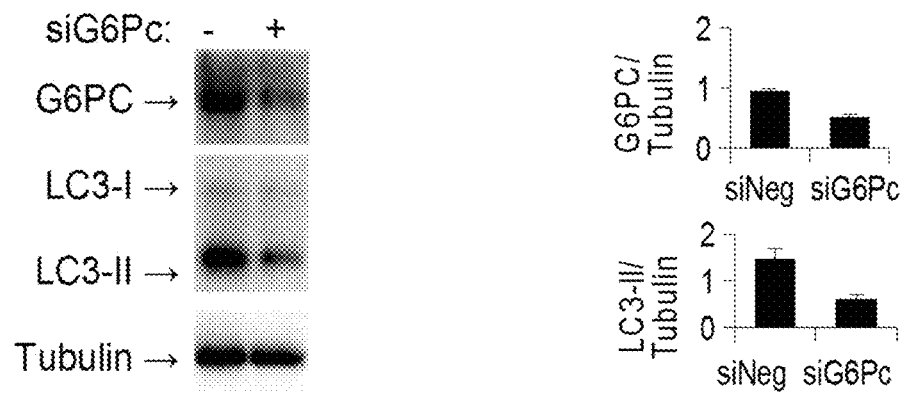
FIG. 13 illustrates LC3-II is reduced in G6pc siRNA-treated AML-12 cells. Treatment of AML-12 mouse hepatocyte cells with siG6pc reduces autophagosome number (LC3-II/tubulin ratio). N=3, and * indicates p<0.05. Error bars: SEM.
Figure 14:
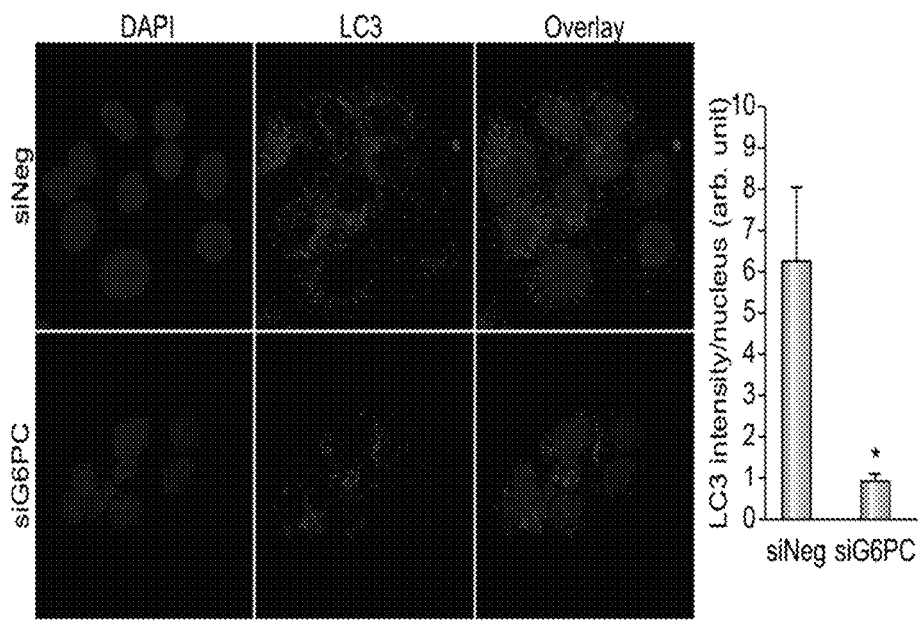
FIG. 14 illustrates G6pc knockdown reduces endogenous LC3 puncta in AML-12 cells stained with α-LC3 antibody. LC3 brightness was quantified and compared to the number of nuclei within the same visual field. N=3 and * indicates p<0.05. Error bars: SEM.
Figure 15:
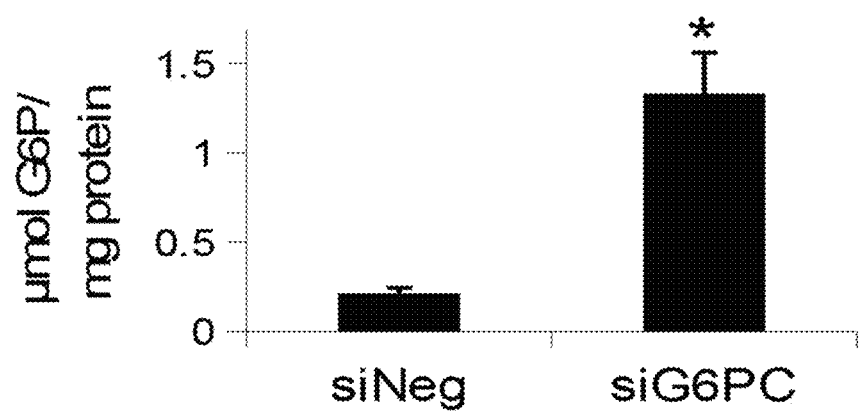
FIG. 15 illustrates glucose-6-phosphate levels are increased in G6pc knockdown AML-12 cells. G6P accumulates in AML-12 cells knocked down for G6pc using siRNA, showing similarity to GSD Ia hepatocytes. N=3, and * represents p<0.05. Error bars: SEM.

Since low-autophagy phenotype of NAFLD occurs in GSD Ia, the potential for autophagy manipulation in GSD Ia was the focus of research. One of these approaches was to recapitulate the GSD Ia phenotype from mouse livers in the AML-12 mouse hepatocyte cell line by knocking down G6pc using siRNA ("siG6P"). The symptoms characteristic of GSD Ia were confirmed in several ways. First, the expected reduction in total LC3-II quantity was confirmed by Western blotting (FIG. 13). To further support this finding, a LC3 puncta staining was performed and the puncta quantified—representing autophagosome formation—per nucleus, and found a corroborative reduction in puncta in knockdown cells (FIG. 14). Since a deficiency in G6PC in humans and animals results in G6P accumulation that feeds into other metabolic pathways and causes disease symptoms, the G6P accumulation in this AML-12 knockdown model was analyzed, and it was found that G6P does in fact accrue when G6pc is knocked down by siRNA in AML-12 cells (FIG. 15).

Figure 16:
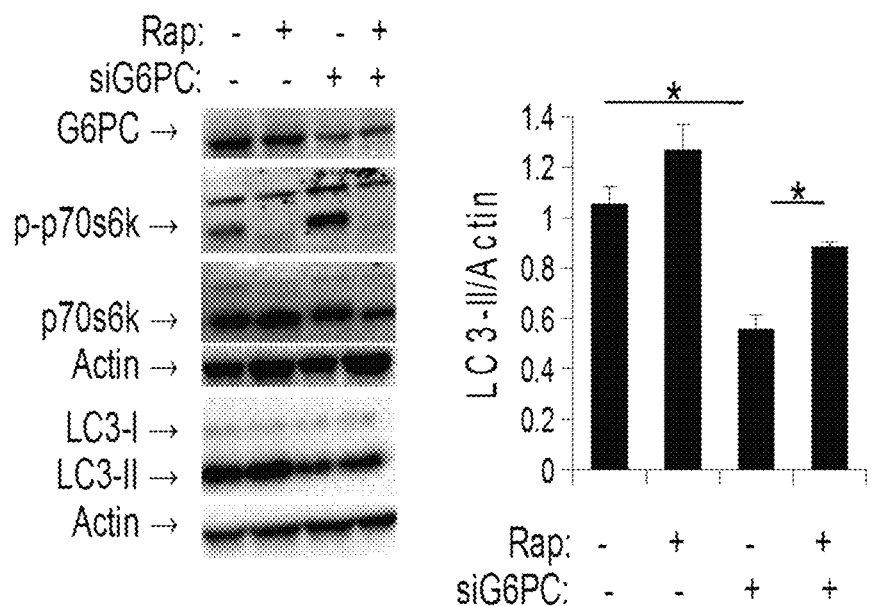
FIG. 16 illustrates rapamycin treatment increases autophagy activity markers in G6pc knockdown AML-12 cells. Western blotting for several autophagy-related proteins indicates that rapamycin (Rap) treatment restores autophagy in G6pc KD AML-12 cells. N=3, * indicates p<0.05 between groups being compared, and ** indicates p<0.01 between groups. Error bars: SEM.
Figure 17:
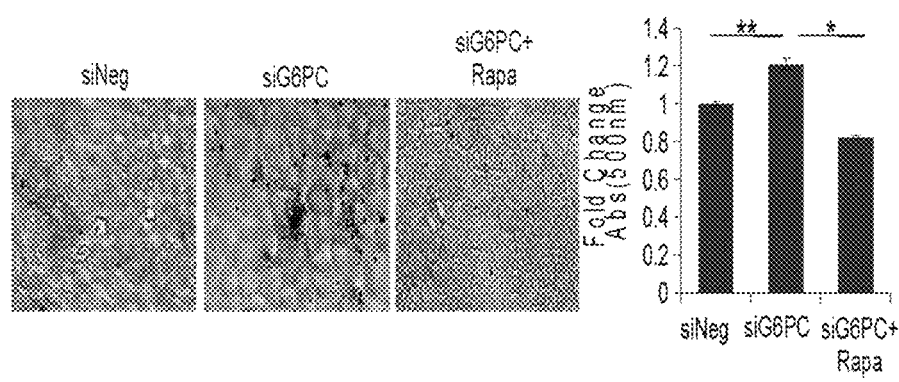
FIG. 17 illustrates rapamycin treatment reduces lipid accumulation in G6pc knockdown AML-12 cells. Oil Red O staining shows that lipid accumulation is restored to low levels by rapamycin application to G6pc knockdown AML-12 cells. N=3, * indicates p<0.05 between groups being compared, and ** indicates p<0.01 between groups. Error bars: SEM.

Having confirmed the autophagy-reduction phenotype in both mice and G6pc siRNA AML-12 cells, the use of rapamycin to induce autophagy in these models was explored. Rapamycin is the prototypical mTOR inhibitor, and since mTOR downregulates autophagy, inhibiting it via rapamycin results in an increase in autophagic activity. This was first tested in the AML-12 model to conserve difficult-to-breed GSD Ia mice. Application of rapamycin to G6pc knockdown AML-12 cells enhanced autophagy and reduced lipid accumulation, as shown in autophagic marker Western blotting and Oil Red O staining (FIGS. 16-17). Phosphorylated p70s6k (p-p70s6k) is indicative of active mTORC, and we observed that rapamycin reduces the amount of p70s6k that is phosphorylated in siG6P-treated AML-12 cells. More importantly, application of rapamycin to knockdown cells results in an increase in LC3-II, which directly indicates an increase in autophagic activity. Similarly, a reduction in lipid accumulation from pro-autophagic rapamycin treatment was expected, and such a lipid reduction, of both visual staining and quantification of Oil Red O adherence intensity was observed.

Figure 18:
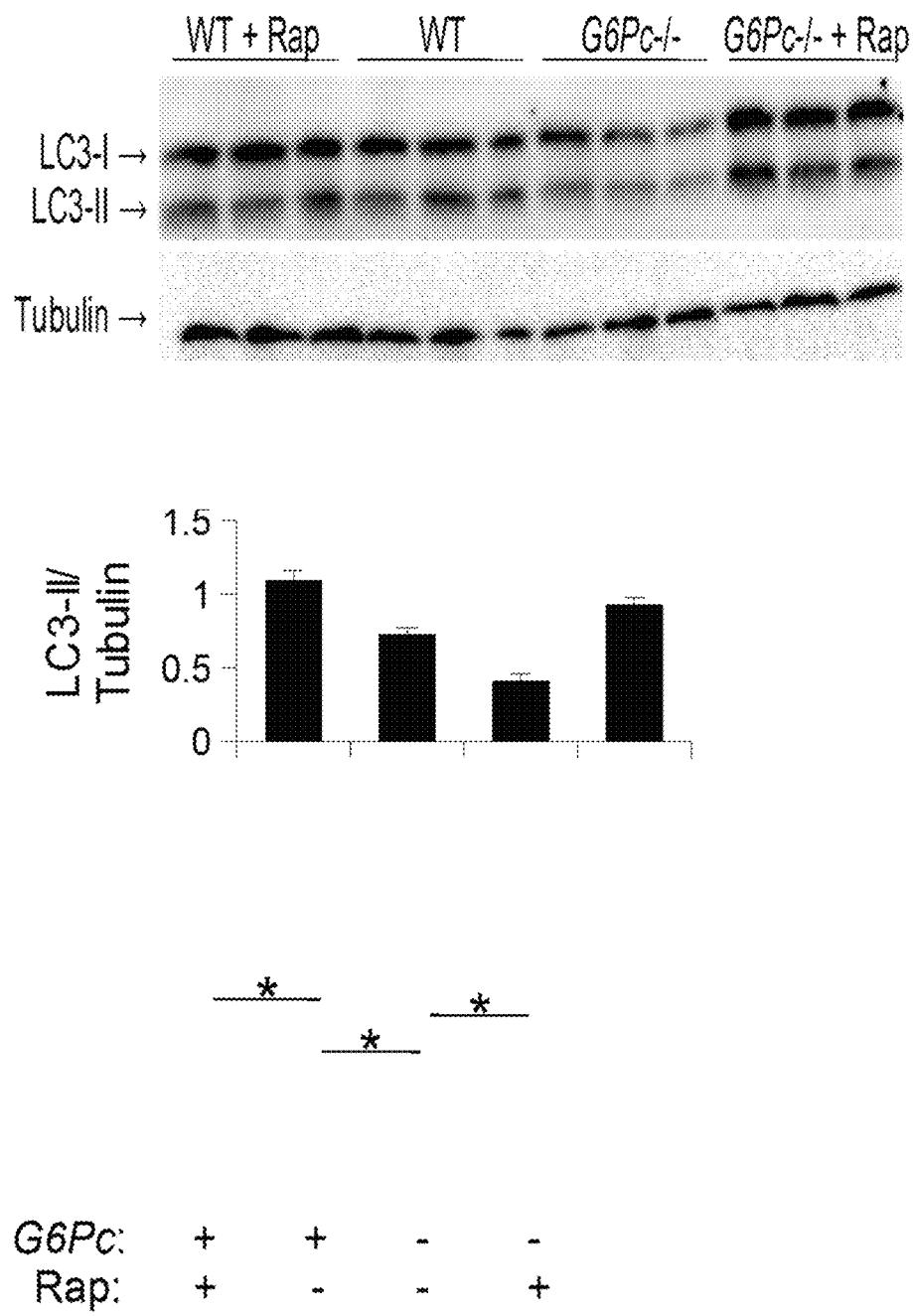
FIG. 18 illustrates Western blotting for LC3-II in mouse livers indicates that treatment of G6pc−/− mice with rapamycin (Rap) increases autophagosome number in the liver (LC3-II/actin). N=3, * indicates p<0.05. Error bars: SEM.

G6pc−/− mice were given intraperitoneal injections of 5 mg/kg rapamycin suspended in 10% DMSO/90% PBS daily for 7 days starting on day 5 of life. We observed an increase in LC3-II in rapamycin-treated mouse livers via Western blotting as predicted (FIG. 18). Electron microscopy was also performed on mouse livers to quantify autophagic vesicles, and mice treated with rapamycin showed an increase in this indication of autophagy (FIG. 19).

Figure 21:
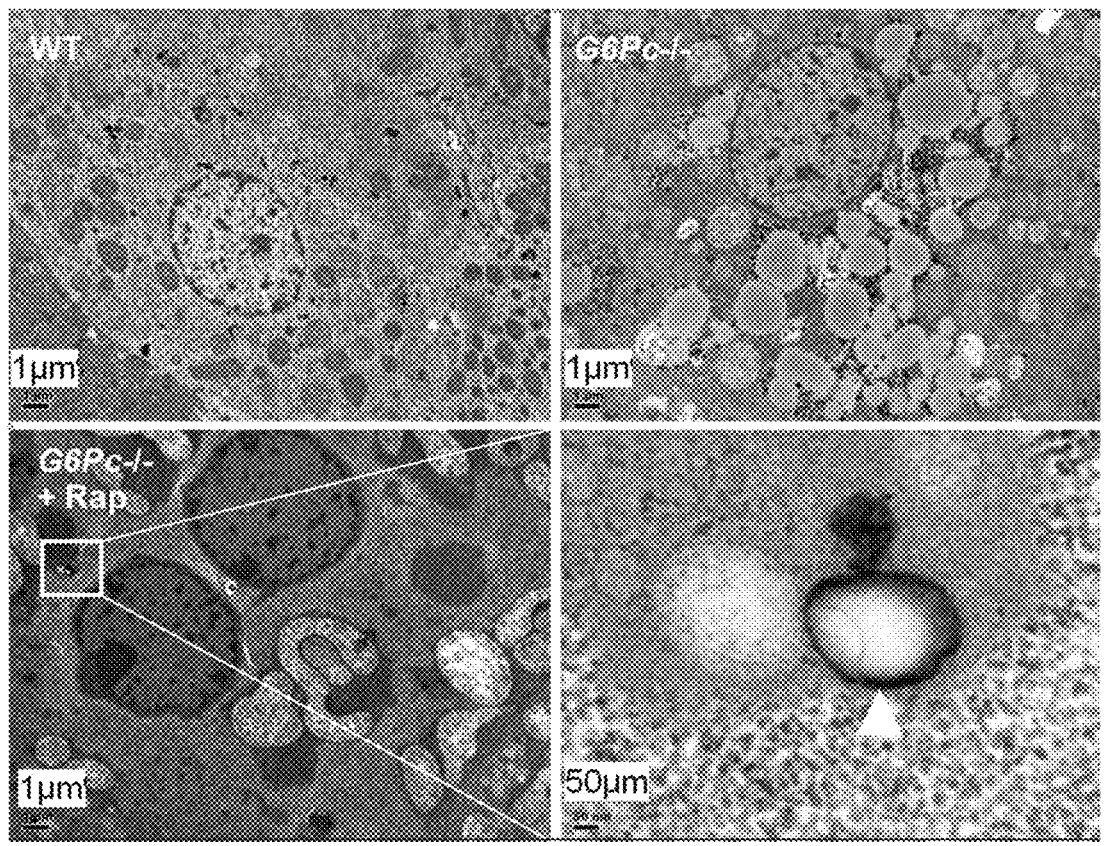
FIG. 21 illustrates lipid vacuoles are diminished in rapamycin-treated GSD Ia mouse livers. Electron microscopy reveals that rapamycin-treated GSD Ia mouse livers have fewer lipid vacuoles in hepatocytes compared with untreated GSD Ia mouse livers.

Liver triglyceride content was quantified in order to determine whether enhancing autophagy reduced lipid accumulation as in AML-12 cells, and we found that liver triglyceride content was indeed reduced by half in G6pc−/− mice following rapamycin administration (FIG. 20). Treatment was sufficient to normalize G6pc−/− mice to the naturally low WT triglyceride levels. That is, the treated group had no significant difference in hepatic triglycerides when compared to vehicle-injected WT mice. Furthermore, electron microscopy revealed a visible reduction in lipid vacuole size and number in GSD Ia mouse livers that received rapamycin (FIG. 21).

Figure 22:
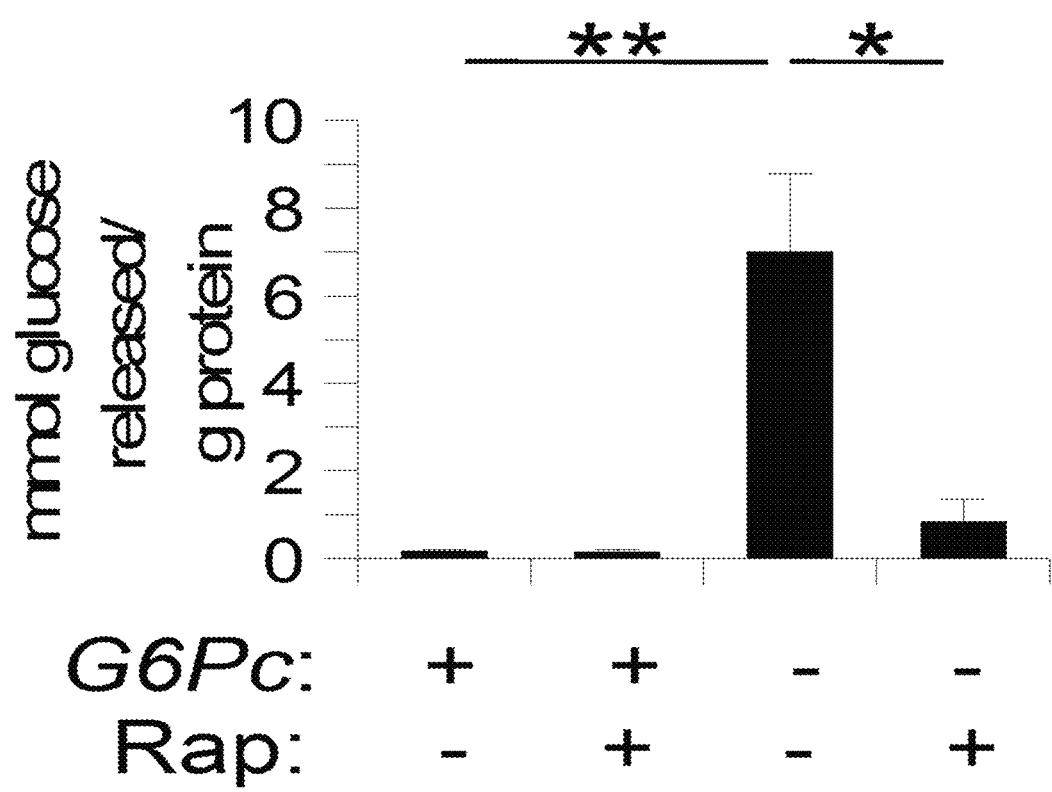
FIG. 22 illustrates liver glycogen accumulation is reduced in GSD Ia mice that receive rapamycin. Glycogen assays revealed a reduction in glycogen (expressed as glucose released during the reaction) in GSD Ia hepatocytes of mice treated with rapamycin compared with those that go untreated. N=5, * indicates p<0.05, and ** indicates p<0.01. Error bars: SEM.
Figure 23:
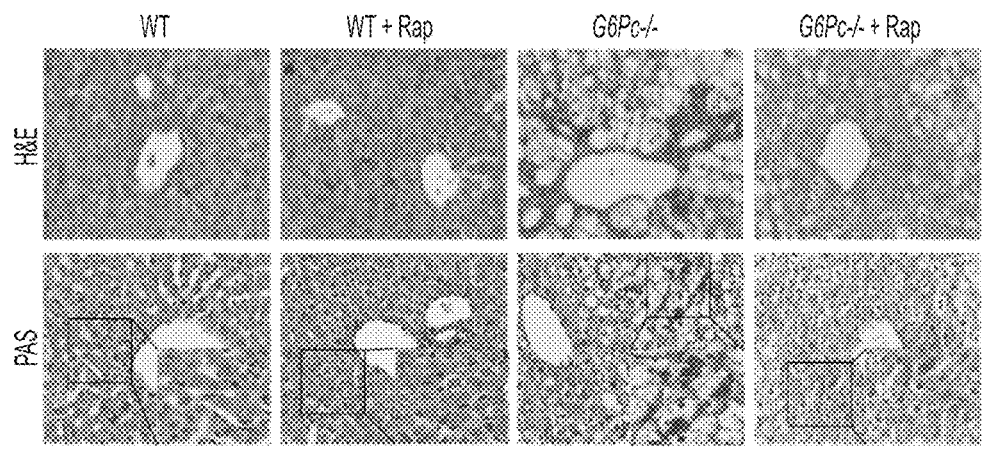
FIG. 23 illustrates histologic analysis (20× magnification) reveals a decrease in lipid and glycogen accumulation in rapamycin-treated mouse livers. Mouse liver sections were stained with H&E and PAS. PAS staining showed reduced hepatic glycogen accumulation in rapamycin-treated mice. H&E stain revealed necrotic cells and lipid vacuoles. In PAS stained samples, insets are digital zoomed 3× further, to 60×.
Figure 24A:
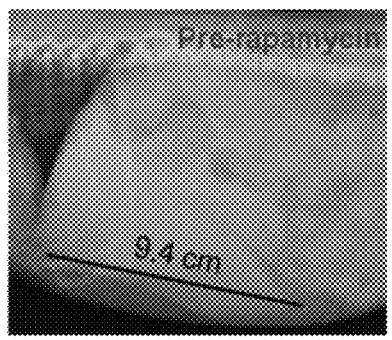
(FIG. 24A) Representative abdominal radiograph of GSD Ia canine after 10 days of rapamycin treatment.
Figure 24A:
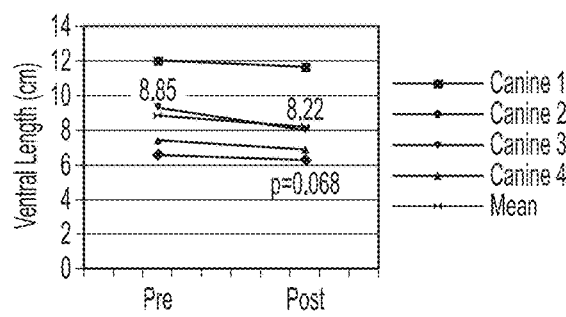
Figure 24B:
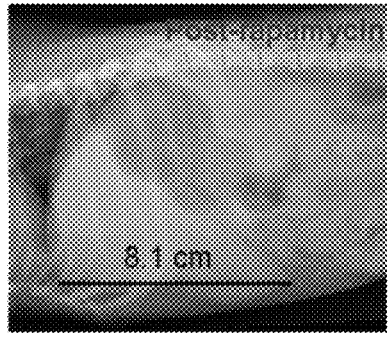
(FIG. 24B) Ventral and dorsal lengths of livers from GSD Ia canines as measured from radiographs pre- and post-rapamycin treatment. N=4, * indicates p<0.05.
Figure 24B:
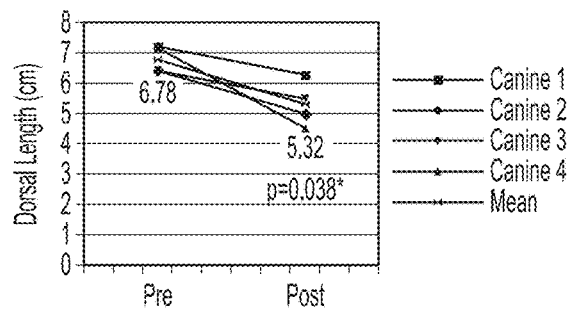

In addition to autophagy and lipids, hepatic glycogen content was also quantified, the elevation of which is characteristic of GSD Ia, and found a substantial reduction for GSD Ia mice that received rapamycin (FIG. 22). Hepatic glycogen content was further analyzed using PAS staining to stain for polysaccharides, including glycogen, in liver sections. It was found that GSD Ia mice undergoing rapamycin treatment had visibly reduced glycogen-laden vacuoles compared with untreated affected mice (FIG. 23). This confirms our hypothesis that manipulating autophagy can reduce glycogen accumulation by breaking it down through alternate routes from the traditional one relying on G6Pase, bypassing the need for G6Pase in GSD Ia hepatocytes.

In addition to the AML-12 and mouse GSD Ia models, we also examined the GSD Ia canine model. The model shows similar symptoms to humans, primarily lethal hypoglycemia, and later in life the canines develop hepatic adenomas and kidney failure like adult human patients. Injections with AAV delivering G6PC to canines are effective for a time, but do not restore 100% of the phenotype. Because treatments are only partially effective, these canines were excellent for examining the efficacy of rapamycin in a large animal model. GSD Ia canines were given 1 mg/kg rapamycin orally daily for 10 days. This was not an endpoint for the canines, so we could not perform the same assays that were done for mice, but we were able to examine liver health using ultrasound to determine the status of the canine's hepatomegaly, and ALT and GGT serum-level assays to determine liver damage. We found that while there was no significant dorsal liver length change, ventral liver length was reduced following rapamycin treatment (FIG. 24). This indicates reduction in hepatomegaly documented prior to drug administration.

Figure 25:
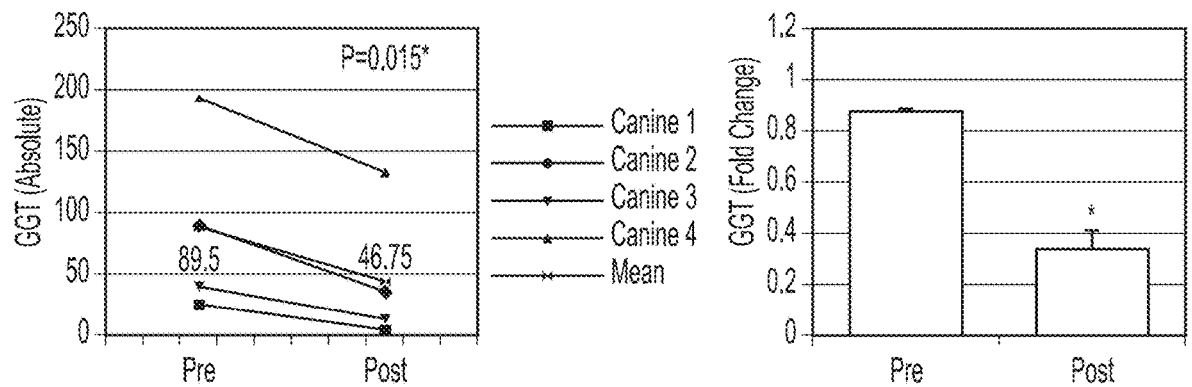
FIG. 25 illustrates GSD Ia canine circulating GGT enzyme levels are reduced following rapamycin treatment. Serum gamma-glutamyl transferase (GGT) levels expressed as absolute and fold-change in the same canines. N=4, and * indicates p<0.05.
Figure 26:
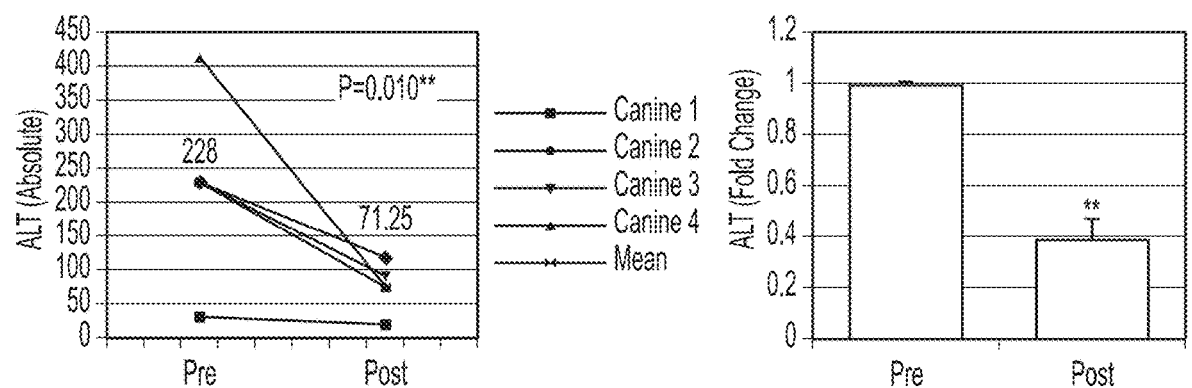
FIG. 26 illustrates GSD Ia canine circulating ALT enzyme levels are reduced following rapamycin treatment. Serum alanine aminotransferase (ALT) levels expressed as absolute and fold-change in the same dogs. N=4, and ** indicates p<0.01. Error bars: SEM.

Likewise, liver health as indicated by serum levels of the liver enzymes GGT and ALT improved with rapamycin administration. GGT levels went down significantly after the 10-day treatment when expressed as either absolute values or fold reduction from the starting point (FIG. 25), and ALT levels went down with significance when expressed as fold reduction from starting values (FIG. 26). These indicate a reduction in liver damage following a 10-day course of oral rapamycin treatment in the canine GSD Ia model.

Example 7

Autophagy-Enhancing Drug Discovery for Gsd Ia

The success of the rapamycin experiments at enhancing autophagy and reducing lipid and glycogen accumulation in cells and mice, and improving liver health in canines showed that autophagy modulation could be a powerful new avenue for GSD Ia therapies. However, rapamycin is a potent, nonspecific mTOR inhibitor, causing it to carry many undesirable side effects. We therefore examined several other drugs for their potential in enhancing autophagy in GSD Ia. A literature review turned up 11 drugs that showed promise in other models where autophagy enhancement ameliorates disease symptoms (Table 6). In brief, a wide array of drugs was selected, including those that modulate autophagy via the inositol-3-phosphate (P3) pathway, those that do so through AMPK modulation to act through mTORC1, and those using yet-undetermined pathways. Analysis of additional literature led to the selection of three concentrations of each compound to be tested in cell culture using the G6pc siRNA knockdown AML-12 mouse hepatocyte cell line model of GSD Ia as an initial screen for the drugs.

TABLE 6

Autophagy-Enhancing Drugs

| Drug | Published Concentration | Low Conc. | Med Conc. | High Conc. |
| --- | --- | --- | --- | --- |
| a-lipoic acid | 25, 50, 100, 200 uM | 50 uM | 100 uM | 250 uM |
| a-tocopherol | 100, 200, 400, 800 uM | 100 uM | 250 uM | 400 uM |
| Bezafibrate | 100 uM | 25 uM | 100 uM | 250 uM |
| Carbamazepine | Cerebrospinal fluid: 0.7-1.5 ug/mL | 1 ug/mL | 5 ug/mL | 10 ug/mL |
| Lithium | 2, 4, 6, 8, 10, 12 mM[141] Serum: 0.8-1.2 mM | 0.5 mM | 1 mM | 2 mM |

TABLE 6-continued

Autophagy-Enhancing Drugs

| Drug | Published Concentration | Low Conc. | Med Conc. | High Conc. |
| --- | --- | --- | --- | --- |
| Metformin | 50 uM, 0.25 mM, 0.5 mM, 2 mM, 2.5 mM | 0.25 mM | 1.5 mM | 2.5 mM |
| Methylene blue | 10, 100, 1000 nM | 10 nM | 100 nM | 1000 nM |
| Mifepristone | 0.1, 1, 10 uM | 0.1 uM | 1 uM | 10 uM |
| Resveratrol | 50, 100 uM | 25 uM | 50 uM | 100 uM |
| Trehalose | 100 mM | 50 mM | 100 mM | 200 mM |
| Verapamil | 70 uM | 50 uM | 100 uM | 250 uM |

Drug concentrations were chosen based on similarity to published concentrations in either cell culture models resulting in target effects or autophagy, or in vivo extracellular fluid concentrations following animal treatments. The latter case is noted with the fluid type. Concentrations used in our in vitro AML-12 cell culture treatments are listed as the low, medium, and high concentrations that were screened.

The first test using AML-12 cells was the Oil Red 0 stain to examine the presence of lipid vacuoles in cells given the treatments. Cell culture wells were each treated with one of the selected doses for each drug and were scored for both reduced lipid accumulation compared with controls, and improved cell survival, since the siRNA knockdown model has high lethality in the AML-12 cells line (Table 7). The screen's results pointed to several drugs as being the best contenders for further research: bezafibrate, carbamazepine, lithium chloride, and mifepristone.

TABLE 7

Lipid Reduction Scoring of Oil Red O-Stained, Drug-Treated, G6pc Knockdown AML42 Cells

| Drug\Dose | Low | Medium | High |
| --- | --- | --- | --- |
| α-Lipoic acid | + | – | 0 |
| α-Tocopherol | 0 (Spotty +) | – (Spotty ++) | – |
| Bezafibrate | – | + | ++ |
| Carbamazepine | +++ | + | 0 |
| Lithium Chloride | +++ | ++ | + |
| Metfonnin | + | +/++ | 0 |
| Methylene Blue | + | – – | – – – |
| Mifepristone | + | + (Spotty ++) | ++ (Great survival) |
| Trehalose | + | – – | – (High death) |
| Verapamil | – | + (But high death) | – – (Very high death) |
| Rapamycin | – – | – – | – – – |
| Resveratrol | + | 0 (Spotty ++) | – – – |
| DMSO | – (Spotty +) | – – | – – |
| Ethanol | – | – | – – |

G6pc siRNA knockdown AML-12 cells were given three different doses of each drug treatment. After 72 hours of growth, the media was changed to ketogenic media and appropriate quantities of each drug were added. This was performed in duplicate. Oil Red 0 staining was then performed and bright field images acquired at 10× magnification.

Drug treatments at three doses each were performed on G6pc siRNA knockdown AML-12 cells. Following oil red 0 staining the whole plates were evaluated visually for reductions in lipid accumulation. Treatments were performed in duplicate. —/0/+/++/+++ indicates the degree of improvement, or lipid reduction, caused by the treatment, with + indicating positive benefits.

Figure 27:
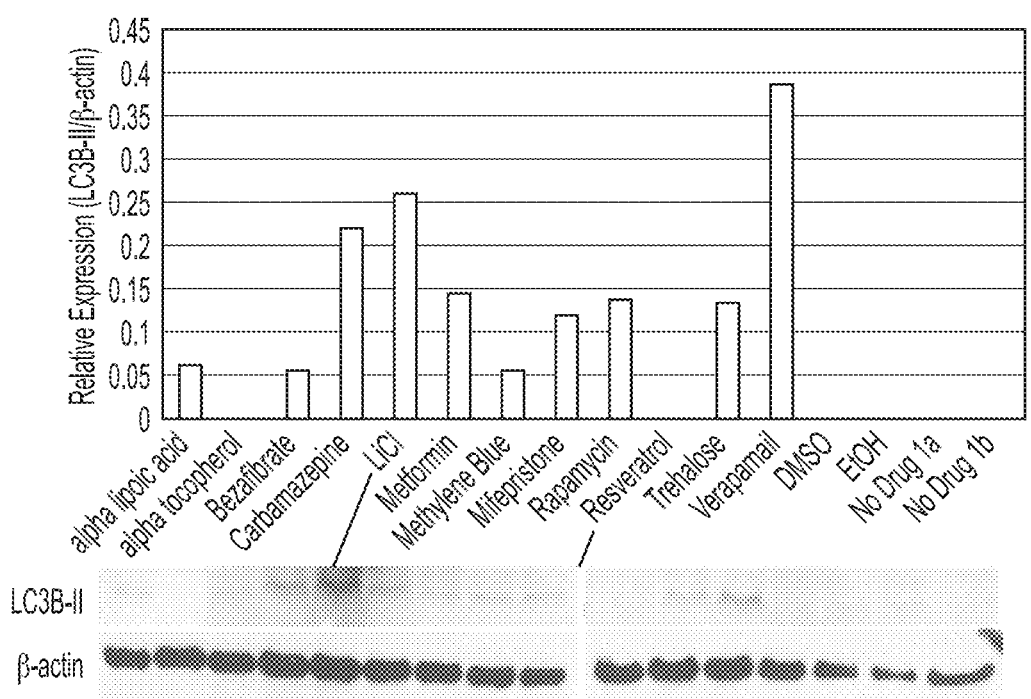
FIG. 27 illustrates LC3 Western blot of drug-treated G6pc knockdown AML-12 cells. Western blotting was performed on AML-12 cells incubated for 24 hours with the described drug conditions. LC3 was quantified and normalized against each condition's β-actin protein quantification.

In addition to Oil Red O staining, cells were analyzed via Western blots for restored LC3 expression for each drug, under the conditions that had optimal effects in the Oil Red O screen (FIG. 27). Since the Western antibody previously used successfully for rapamycin treatment LC3 blots had been discontinued by the manufacturer, we tested two alternative antibodies and chose the one from Cell Signaling Technologies because it gave the strongest signal-to-noise ratio under our experimental conditions. Western blotting confirmed the autophagy-enhancement effects of many drugs that showed lipid reduction through the Oil Red O stain, and in particular it corroborated the results of bezafibrate, carbamazepine, lithium chloride, and mifepristone application by demonstrating the increase in LC3 autophagic marker predicted based on their lipid-reducing effects (FIG. 27).

Western blotting was performed on AML-12 cells incubated for 24 hours with the described drug conditions. LC3 was quantified and normalized against each condition's β-actin protein quantification.

Carbamazepine and lithium have potent psychoactive effects. Lithium compounds were among the first mood-stabilizing drugs used to treat bipolar disorder and schizophrenia circa 1949, and anticonvulsants, particularly carbamazepine, have been combined with lithium in the treatment of bipolar disorder and schizophrenia for over three decades. The fact that lithium is still prescribed as a mood stabilizer in the treatment of bipolar disorder after 75 years stands as a testament to the potency of its psychoactive effects. These beneficial effects for patients suffering from psychiatric illnesses would instead become serious side effects in patients prescribed lithium and/or carbamazepine to ameliorate GSD Ia symptoms, so lithium chloride and carbamazepine have not been pursued in mice as potential GSD Ia treatments at this time.

Mifepristone is used to induce chemical abortions up to day 70 of pregnancy. These on- and off-label purposes could produce significant side-effects in GSD Ia patients using mifepristone to improve their autophagic activity. Furthermore, the side effects of the drug itself as described on the FDA label include nausea, vomiting, and diarrhea, which could make it difficult for patients to intake sufficient calories for combating hypoglycemia, potentially negating the benefits. Therefore, administration of mifepristone was not pursued in GSD Ia mice.

This left bezafibrate as the best candidate to emerge from the screen. Bezafibrate is a PPARα agonist used to lower cholesterol levels and prevent hyperlipidemia to reduce the risk of heart disease. Since hyperlipidemia is a symptom of GSD Ia, this pre-established on-label effect could have benefits in addition to autophagic enhancement in patients. In terms of side effects, bezafibrate does induce loss of appetite and elevation in circulating liver enzymes. While these could complicate therapeutics taking advantage of the medication for GSD Ia, the overall effects on autophagy and hyperlipidemia would likely outweigh the downsides, so we chose bezafibrate to move forward as our best drug candidate in GSD Ia mice.

G6pc−/− knockout mice were administered intraperitoneal injections of bezafibrate 25 mg/kg/day suspended in 10% DMSO/90% PBS IP for 3 days.

Figure 28:
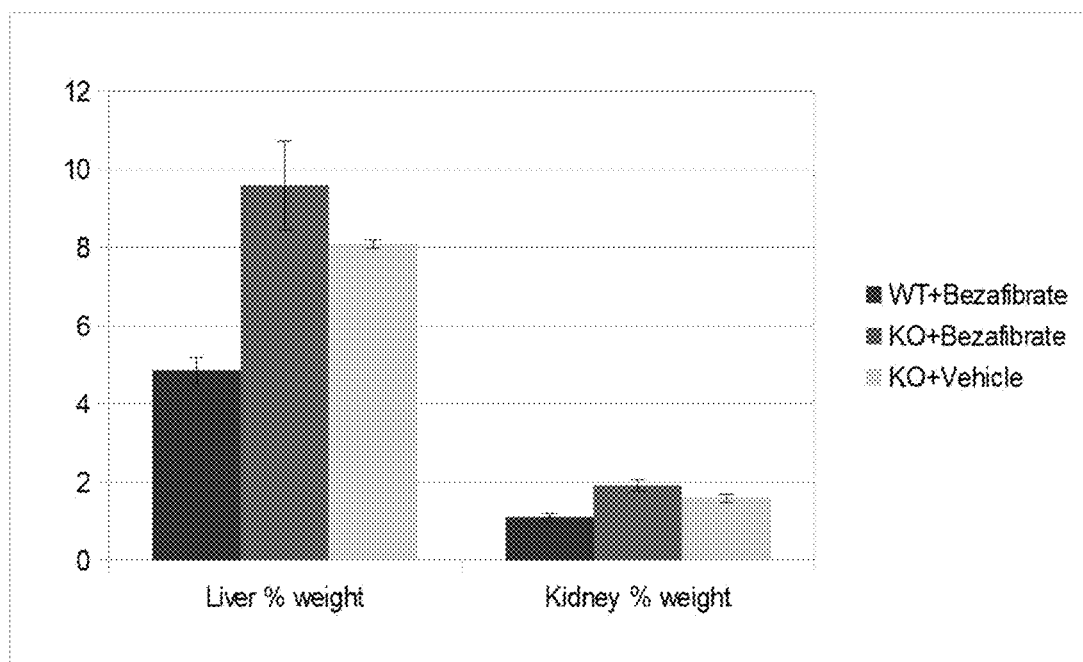
FIG. 28 illustrates bezafibrate-injected GSD Ia mice liver and kidney weights. Livers and kidneys from mice undergoing bezafibrate injections were weighed at the time of collection, weights expressed here as percentage of body weight. * indicates p<0.05. Error bars: mean±SD.
Figure 32A:
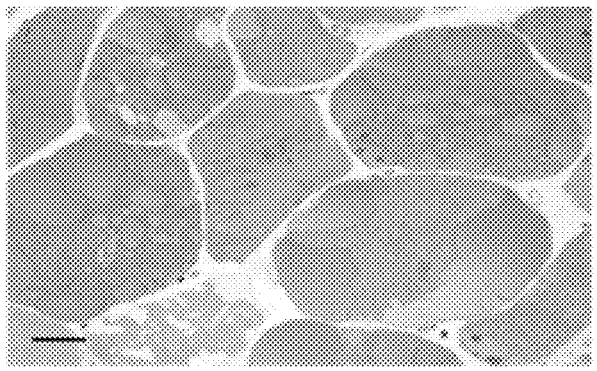
(FIG. 32A) High-resolution light microscopy demonstrates that purple-staining glycogen is present as non-membrane-bounded cytoplasmic lakes within myocytes by Periodic Acid Schiff (PAS) staining (scale bar=20 μm).
Figure 32B:
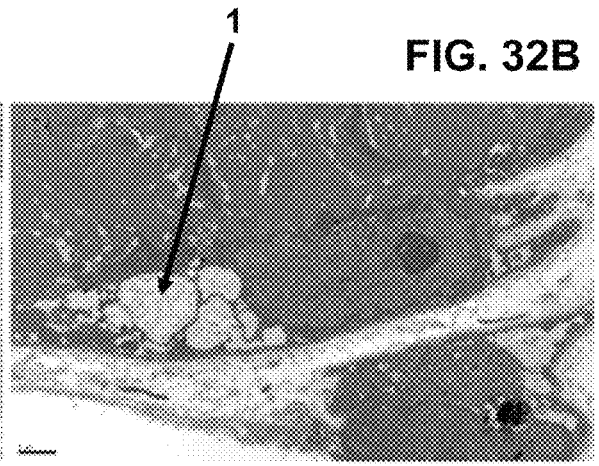
(FIG. 32B) Under EM, occasional lysosomal glycogen 1 (identified at the end of arrow) was also seen in the myocytes (scale bar=1 μm).
Figure 32C:
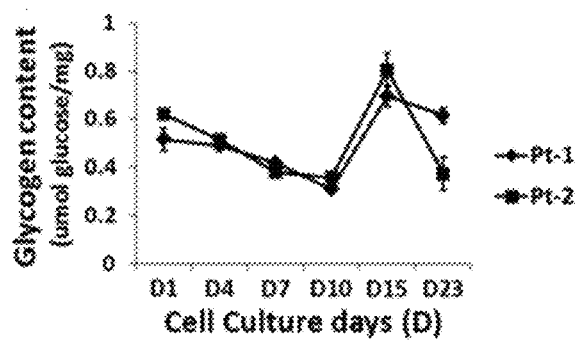
(FIG. 32C) Glycogen accumulation pattern revealed that glycogen content was peaked at Day 15 in cultured patient muscle cells.
Figure 32D:
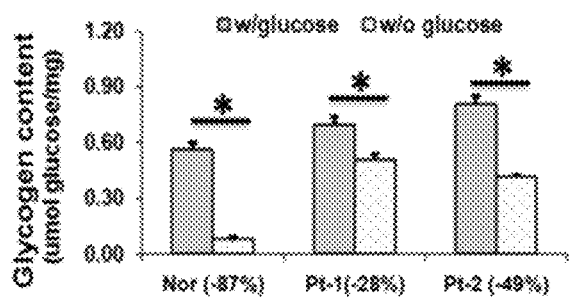
(FIG. 32D) Glucose starvation experiment showed incomplete glycogen utilization in the muscle cells from both GSD IIIa patients compared to a normal control subject (Nor).
Figure 32E:
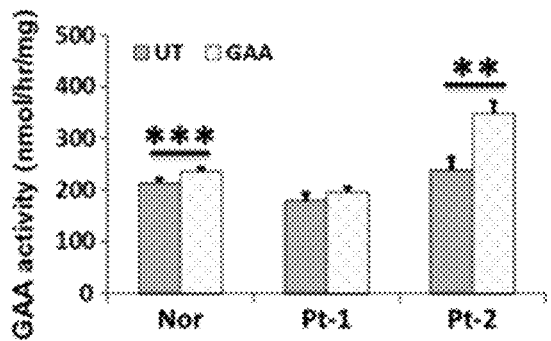
(FIG. 32E) GAA activity in normal and patient cells 48 h after adding recombinant human acid alpha-glucosidase (rhGAA, Myozyme*, alglucosidase alfa) treatment.
Figure 32F:
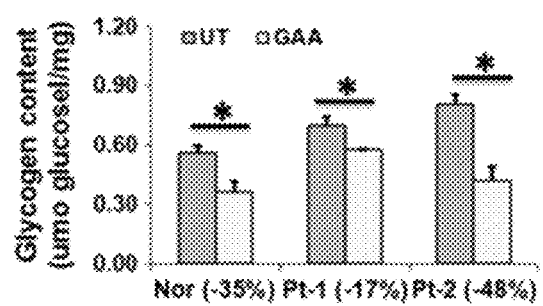
(FIG. 32F) rhGAA significantly reduced glycogen concentration in both normal and patient cells. Mean ±standard deviation is shown in FIG. 32C-FIG. 32F (n=4). The significance of differences between two different groups was assessed using the two-tailed, equal variance student T-test (*P<0.001; P<0.01; *P<0.05).

At the time of tissue collection, blood glucose was analyzed and affected mice were found to have no increase when treated with bezafibrate, their levels consistently below the threshold of detection (<20 mg/dL). However, liver and kidney weights were recorded at the time of sacrifice, and these data revealed a slight difference in kidney size as a percentage of body weight. Bezafibrate caused a very small but quantitatively significant increase in kidney weight expressed as a percentage of total body weight (p<0.046) (FIG. 28). This runs contrary to the expectation that bezafibrate would reduce kidney size in G6pc−/− mice.

Livers and kidneys from mice undergoing bezafibrate injections were weighed at the time of collection, weights expressed here as percentage of body weight. * indicates p<0.05. Error bars: mean±SD.

A single administration of bezafibrate increased LC3-II significantly, in comparison with vehicle-treated mice of the same age (FIG. 29). This result demonstrated increased formation of autophagosomes consistent with the induction of autophagy.

The effects of bezafibrate upon autophagy were further demonstrated by decreased plasma triglycerides (FIG. 30A). Similarly, liver triglycerides were reduced in G6Pc−/− mice following bezafibrate administration (FIG. 30B). However, the effect of a single dose of bezafibrate did not reduce liver glycogen content (not shown). These data suggest that the induction of autophagy with bezafibrate was sufficient to decrease the lipid accumulation associated with GSD Ia, which underlies the reduction of autophagy and increase in apoptosis associated with the liver involvement of GSD Ia, features shared with NAFLD. These data promise that drugs such as bezafibrate will reverse the liver effects of GSD Ia at least in part.

The current approach to GSD Ia therapy focuses on preventing lethal hypoglycemia by providing constant calories throughout the day. This fails to prevent many of the chronic symptoms, including hepatomegaly, hyperlipidemia, and glycogen accumulation. While gene therapy approaches appear very promising for long-term treatments and are likely to be extremely beneficial down the line, gene therapy as a treatment field overall is still immature. It takes many years to develop gene therapeutics, and the manufacturing process is still slow and difficult to scale efficiently. As such, stopgap and combinatorial treatments for GSD Ia will be extremely valuable, in that they can provide benefit to patients living with the disease in a much shorter timeframe than can gene therapies.

Autophagy manipulation has only recently been explored as a therapeutic approach to many diseases in which toxic accumulation of endogenous products causes health problems, including prion diseases, Alzheimer's disease, and NAFLD. The theory behind these treatments is that enhanced autophagy may be able to break down the excess products trapped in cells that causes clinical defects. Since much of GSD Ia's symptom set derives from excess lipids, glycogen, and even amino acids, it stands to reason that autophagy could be useful for treating aspects of GSD Ia to reduce the symptoms and improve the quality of life for patients living with it long term.

In exploring this route, we first found that autophagy is reduced in GSD Ia mice livers and kidneys as well as in the G6pc knockdown AML-12 mouse hepatocyte cell line model (FIGS. 1, 2, and 4). What this meant to us was that increasing autophagy in GSD Ia would not actually mean raising its levels above normal, but rather restoring its levels closer to normal. The distinction means that pro-autophagic treatments are likely to have fewer and less intense side effects in patients, further indicating that this course of treatment investigation is a strong contender for future GSD Ia therapeutics. We believe the autophagic reduction occurs because excess G6P that accumulates as a result of insufficient G6Pase to hydrolyze it signals the cell that the cell is under fed conditions-conditions under which cells try to store excess energy by activating lipogenesis and inhibiting autophagy and fatty acid oxidation. Reversing this state could potentially be done by inhibiting mTORC1 or through other pathways that could out-compete the mTORC1 inhibitory effect.

Using rapamycin, the prototypical mTOR inhibitor to induce autophagy, we confirmed that inhibiting mTORC1 can enhance autophagy in GSD Ia model cells and mice, and that doing so reduces lipid and glycogen accumulation characteristic of GSD Ia (FIGS. 7-14). The effects were further examined in GSD Ia canines by analyzing the reduction in hepatomegaly and liver damage (as indicated by circulating GGT and ALT levels) induced by rapamycin treatment (FIGS. 24-26).

While rapamycin administration showed great effects, its known toxicity, off-target effects, and side effects in humans due to its general inhibition of mTORC1, which controls a wide variety of cellular pathways, makes it a relatively poor option for long-term human treatment. Therefore, we decided the next step was to look for alternative drugs with similar pro-autophagic effects to rapamycin that may produce fewer side effects through long-term administration. We began by using our newly-developed G6pc knockdown AML-12 cell model as a screening system for several drugs with known autophagy-enhancing effects, and analyzed these drugs using Oil Red O staining and LC3 western blots to determine their ability to reduce lipid accumulation in GSD Ia-like cells and confirm their ability to enhance autophagy in the face of GSD Ia (Table 7 and FIG. 27). We found several drugs with pro-autophagic effects in the face of GSD Ia symptoms, and ultimately chose the one with the least toxicity and potential for deleterious side-effects to proceed with in G6pc−/− mice, bezafibrate. This drug has the added benefit of not yet being FDA approved for any kind of therapy in the U.S., but is a well-documented drug approved for use in Europe. This makes it enticing for future research for commercialization because it could be picked up and its research funded by the pharmaceutical industry while already having many toxicity studies completed.

We found that bezafibrate shows trends in enhancing autophagy in GSD Ia mice, but the effect is not significant. However, the study is ongoing and as additional mice are added to treatment groups to increase statistical power, we anticipate the improvements becoming significant. Furthermore, hepatic lipid and glycogen accumulation assays have yet to be performed, and they are planned for the future.

Overall this study has shown that autophagy manipulation has great potential to provide therapeutic benefits for GSD Ia. Rapamycin may not be the best drug for these purposes, but it has opened the door on this new approach. Our small screen has turned up several drugs, and additional screens may reveal yet more as the field of autophagy enhancement grows and more pro-autophagic drugs become known.

Ongoing work with bezafibrate is so far promising, and our other top drug candidates, carbamazepine, lithium chloride, and mifepristone, are excellent options to further pursue this course in mouse treatments. We expect that autophagy induction will prove to be an approach rich with new GSD Ia therapies that will be brought to bear in the years to come, dramatically improving the quality of life and clinical outcomes for GSD Ia patients in the near future.

Example 8

RhGAA Reduced Glycogen Accumulation in Cultured Primary Muscle Cells Derived from the GSD IV Mice Primary myoblast cells were isolated from 7-day-old GSD IV mouse skeletal muscle. Early passage cells were seeded in 10-cm culture dishes with EMEM medium containing 10% FBS. When cells reached 90% confluence, rhGAA was added to the culture medium (final activity=1000 nmol/hr/ml). The cells were harvested 24 hours later to analyze glycogen content and GAA activity. As shown in FIG. 33A, GAA activity increased by 50%, and as shown in FIG. 33B, glycogen content decreased by 24% after the rhGAA treatment. Results have shown that recombinant human acid alpha-glucosidase (rhGAA) significantly reduced glycogen content in primary muscle cells from GSD IIIa patients (FIG. 32) and in the primary myoblasts from GSD IV mice (FIG. 33 and FIG. 34) in vitro It is believed that enhanced GAA activity leads to rapid lysosomal glycogen clearance, increased glycogen shuffling from cytoplasm into lysosomes, and a reduced overall cytoplasmic glycogen level in the affected tissues of GSD III and IV.

Reduction of glycogen deposition in GSD IV mouse myoblasts by rhGAA treatment was also confirmed by immunofluorescence staining using a mouse anti-glycogen monoclonal antibody ESG1A9mAb. As shown in FIG. 34, the untreated cells (0 hr) contained heavily stained glycogen particles of various sizes. The reduction of glycogen was obvious at 4 hours (4 hr) and became more evident at 24 hours (24 hr) following the rhGAA treatment.

Example 9

Characterization of a Mouse Model of GSD IV

Figure 35:
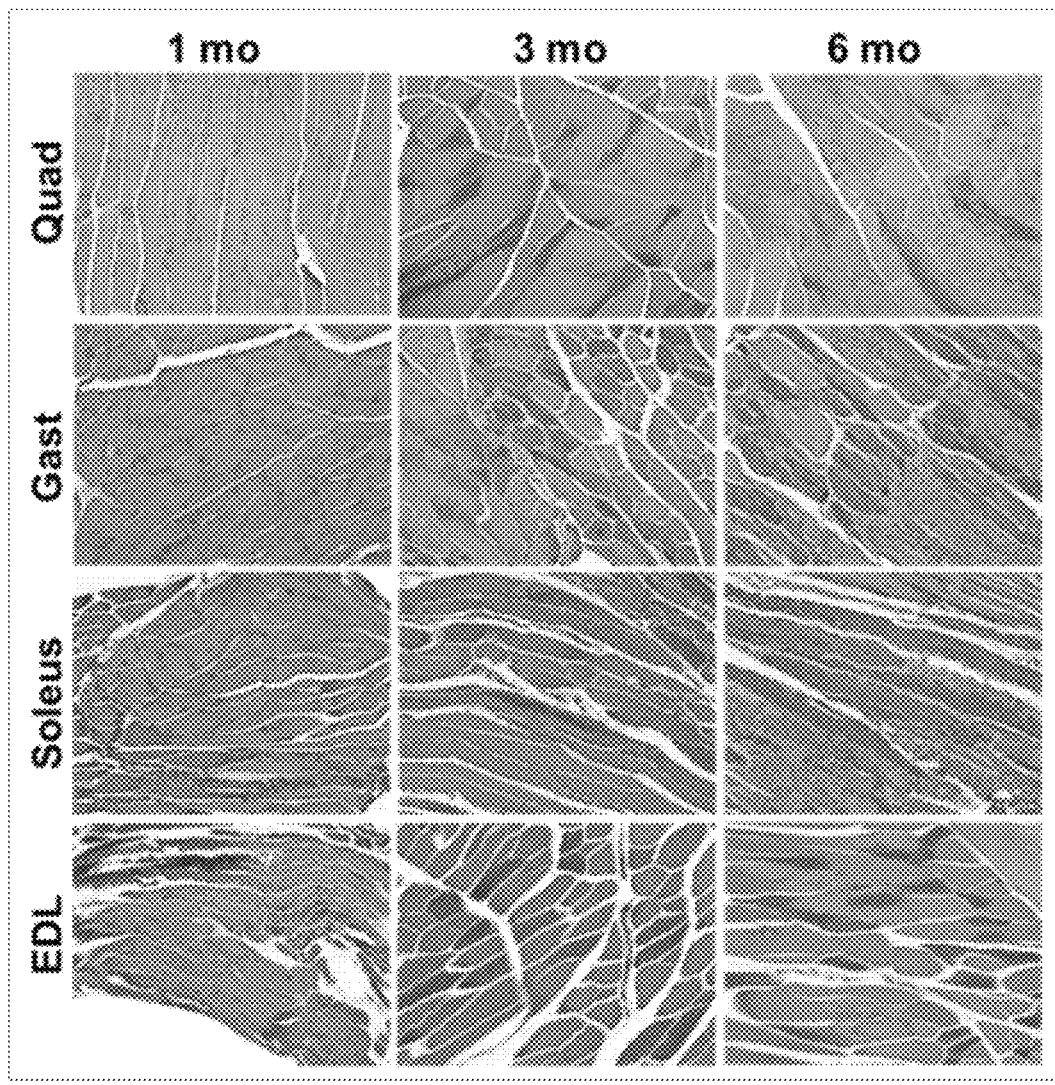
FIG. 35 illustrates progressive glycogen deposits in various muscles of GSD IV mice. There were no or very scarce PAS positive particles detected in muscles detected in muscles at 1 month of age. A significant amount of PAS positive cells were observed at 3 months and 6 months of age, indicating the progressive nature of glycogen accumulation in GSD IV.
Figure 36:
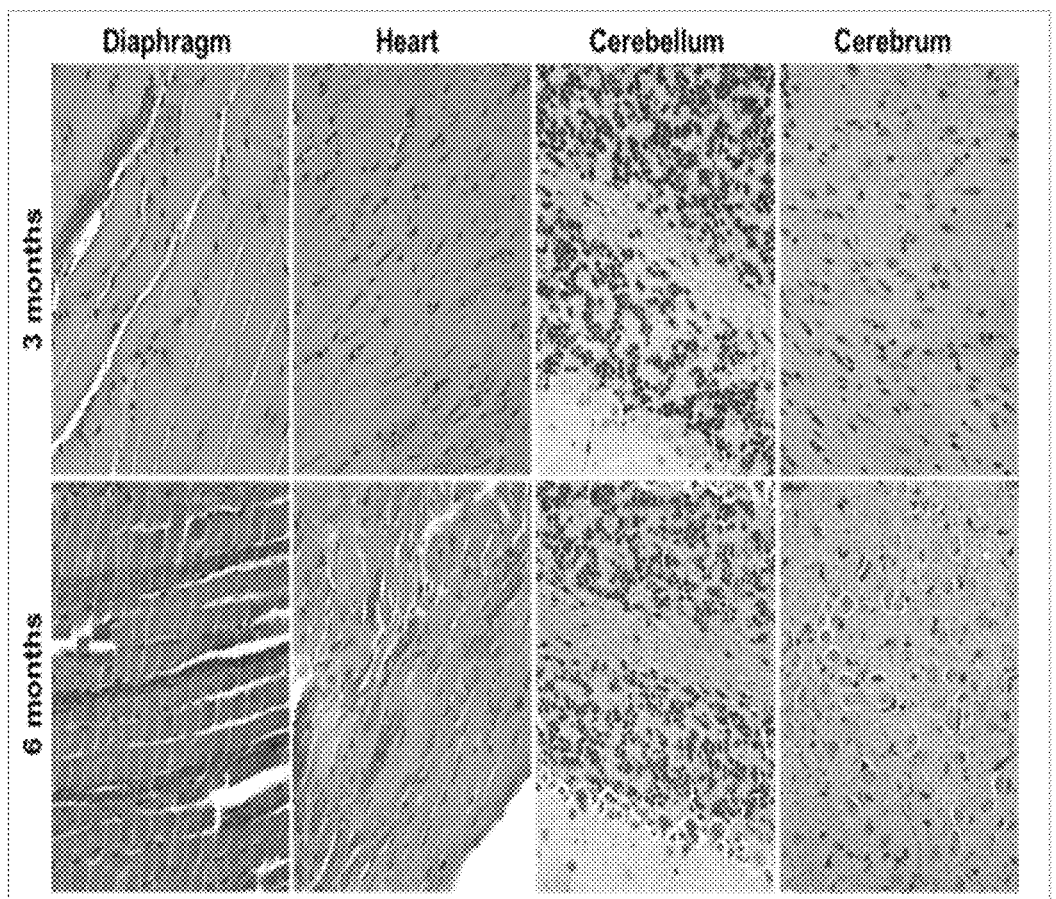
FIG. 36 illustrates glycogen deposits in the diaphragm, heart, and brain of GSD IV mice. PAS positive particles were detected in these tissues at 3 months of age and became more prevalent at 6 months of age.

GSD IV is an autosomal recessive disorder caused by deficiency of glycogen branching enzyme (GBE) which results in deposition of less-branched amylopectin-like polysaccharide in muscle, liver, and the CNS. Prior to the present embodied treatment, liver transplantation was the only treatment option for patients with progressive liver fibrosis. A mouse model (Gbe1$^{ys/ys}$, model) of GSD IV was obtained from Dr. Craigen and Dr. Akman of Baylor College of Medicine (unpublished). The affected mice (GSD IV mice) carry the Y329S mutation, the most common mutation found in patients with late-onset GSD IV or adult polyglucosan body disease (APBD). PAS stained tissue sections revealed progressive glycogen deposition in skeletal muscles of the Gbe1 mice (FIG. 35). There were less PAS positive particles in diaphragm, heart, and the brain at 3 months of age but became more prevalent at age 6 months (FIG. 36).

Figures 37A, 37B:
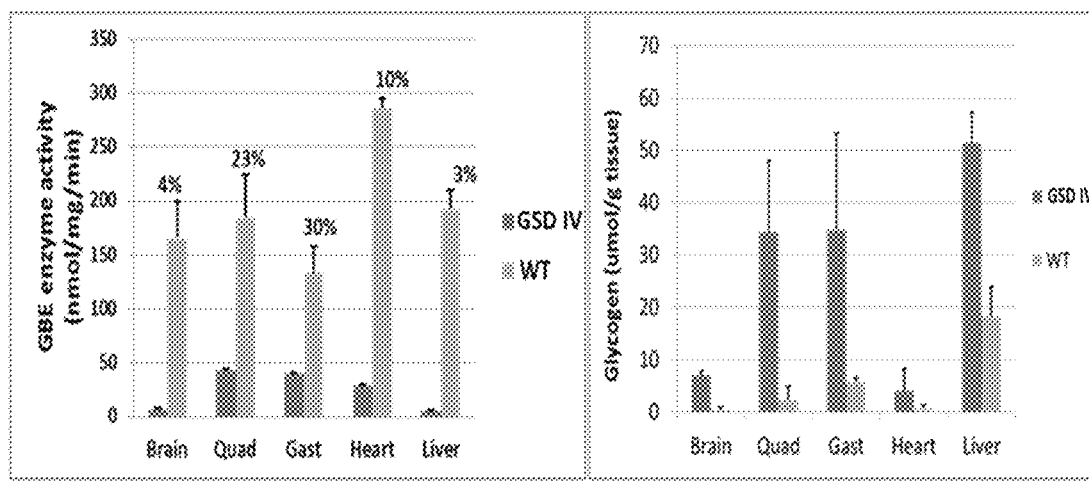
FIG. 37A illustrates the GBE enzyme activity and FIG. 37B illustrates the glycogen content in GSD IV mice and wild-type (WT) mice at age of 3 months. The percentage of residual GBE activity in the GSD IV mice to WT mice was shown in FIG. 37A. n=5.

Tissue GBE enzyme activity and glycogen content at age 3 months were compared with age-matched wild-type (WT) mice. As shown in FIG. 37, reduced GBE activity was detected in all tissues of the GSD IV mice, ranging from 3% in the liver to up to 30% in the skeletal muscle (FIG. 37A). Glycogen content was highly elevated in all tissues of the GSD IV mice in comparison with the WT mice (FIG. 37B).

Example 10

A Modified Enzymatic Method for Measurement of Glycogen Content in Glycogen Storage Disease Type IV

SUMMARY

Deficiency of glycogen branching enzyme in glycogen storage disease type IV (GSD IV) results in accumulation of less-branched and poorly soluble polysaccharides (polyglucosan bodies) in multiple tissues. Standard enzymatic method, used to quantify glycogen content in GSD IV tissues, causes significant loss of the polysaccharides during preparation of tissue lysates. We report a modified method including an extra boiling step to dissolve the insoluble glycogen, ultimately preserving the glycogen content in tissue homogenates from GSD IV mice. Muscle tissues from wild-type, GSD II and GSD IV mice and GSD III dogs were homogenized in cold water and homogenate of each tissue was divided into two parts. One part was immediately clarified by centrifugation at 4° C. (STD-prep); the other part was boiled for 5 min then centrifuged (Boil-prep) at room temperature. When glycogen was quantified enzymatically in tissue lysates, no significant differences were found between the STD-prep and the Boil-prep for wild-type, GSD II and GSD III muscles. In contrast, glycogen content for GSD IV muscle in the STD-prep was only 11% of that in the Boil-prep, similar to wild-type values. Similar results were observed in other tissues of GSD IV mice and fibroblast cells from a GSD IV patient. This study provides important information for improving disease diagnosis, monitoring disease progression, and evaluating treatment outcomes in both clinical and preclinical clinical settings for GSD IV. This report should be used as an updated protocol in clinical diagnostic laboratories.

INTRODUCTION

In animal cells, glycogen synthesis is primarily catalyzed by two enzymes, glycogen synthase (GS, EC 2.4.1.11), which adds glucose residues to a linear chain, and glycogen branching enzyme (GBE, EC 2.4.1.18), which adds branches to the growing glycogen molecule. Although the majority of glycogen is degraded in the cytoplasm by the combined action of glycogen phosphorylase and glycogen debranching enzyme (GDE, EC 2.4.1.25/EC 3.2.1.33), a small percentage of glycogen is transported to and hydrolyzed in lysosomes by acid α-glucosidase (GAA, EC 3.2.1.20).

Glycogen storage diseases (GSDs) are a group of inherited disorders caused by deficiency of a certain enzyme involved in glycogen synthesis or degradation. While the accumulation of glycogen in liver and muscle tissues is the common consequence of these diseases, the molecular structure and property of glycogen varies between specific GSDs. For example, deficiency of GAA in GSD II causes accumulation of glycogen with normal structure in the lysosomes. In GSD III, loss of GDE enzyme activity hinders further breakdown of glycogen from branching points, resulting in the accumulation of abnormal glycogen with short outer chains. In GSD IV, deficiency of GBE leads to the production of less-branched and poorly soluble polysaccharides (polyglucosan bodies, PB) in all body tissues.

Biochemical quantification of glycogen content is critical for disease diagnosis, disease progression monitoring, and therapeutic outcomes evaluation in both clinical and preclinical settings. An enzymatic method based on homogenization of tissues in cold water followed by *Aspergillus niger* amyloglucosidase (EC 3.2.1.3) digestion has become widely-used for measuring glycogen content in tissue. In the past decade, our team has had success using this method to quantify glycogen in various tissues from experimental animals with GSD type I, II, or III. Recently, in our work with a mouse model of GSD IV, we found that the measured tissue glycogen contents were at extremely low levels, which contradicts with the observation that strongly PAS-positive PB were present in these tissues. Considering the low solubility of the PB in GSD IV, we speculated that the majority of glycogen was lost during the lysate preparation. Here we describe a modified enzymatic method for glycogen quantification in GSD IV.

Materials and Methods

Animal Tissues

Muscle tissues were obtained from 3-month-old GAA knockout (GSD II) mice (Raben et al., 1998) and from 4-month-old GSD IIIa dogs. GSD IV (Gbe1ys/ys) mice were euthanized at age of 3 months following overnight fasting for collection of tissues. Muscle tissues from 3-month-old wild-type (C57BL/6) mice were used as controls. Fresh tissues were fixed in 10% neutral buffered formalin for PAS staining or frozen in −80° C. freezer until use. All animal experiments were approved by the Institutional Animal Care & Use Committee at Duke University and were in accordance with the National Institutes of Health guidelines.

Tissue Lysate Preparation

Frozen tissues (50-100 mg) were homogenized in ice-cold de-ionized water (20 ml water/g tissue) and sonicated three times for 15 seconds with 30-second intervals between pulses, using a Misonix XL2020 ultrasonicator. Homogenate of each tissue was divided into two parts and processed separately: one part was immediately clarified by centrifugation at 4° C. (STD-prep); the other part was boiled for 5 min then centrifuged at room temperature (Boil-prep).

Cell Culture and Cell Lysates

Fibroblasts derived from skin biopsies of a patient with GSD II and one with GSD IV were harvested after 3 days in culture in 10-cm plates. The cell pellet from each plate was resuspended in 300 μl cold water and sonicated three times. The STD-prep and Boil-prep cell lysates were then prepared as described above. Protein concentration of the STD-prep was determined using BCA method.

Glycogen Content Measurement

Glycogen contents in the tissue and cell lysates (both the STD-prep and the Boil-prep) were assayed.

Statistical Analysis of Glycogen Content

The significance of differences between the STD-prep and Boil-prep of the same group of samples was assessed using two-tailed, paired student T-test. Mean ±standard deviation were shown.

Results

Glycogen Staining and Quantitation in Skeletal Muscles from Wild-Type and GSD Animals PAS staining of glycogen revealed no visible PAS-positive materials in wild-type (Wt) mice. In GSD II mice, glycogen-filled lysosomes of various sizes were scattered throughout the tissue; in GSD III dogs, filamentous glycogen aggregates and large pools of glycogen were seen; in GSD IV mice, granular glycogen particles were observed in most myocytes (FIG. 38A).

When glycogen was quantified in tissue lysates, no significant differences were found between the STD-prep and the Boil-prep for wild-type (Wt), GSD II and GSD III muscles (FIG. 38B). In contrast, the GSD IV muscle showed a very low level of glycogen in the STD-prep lysates (3.17±1.15 μmol glucose/g tissue), similar to that of wild-type muscle, while the Boil-prep showed a markedly higher level (34.5±12.7), indicating significant loss of glycogen in the STD-prep lysates (FIG. 38B).

Glycogen Staining and Quantitation in Other Tissues from GSD IV Mice

PAS staining of glycogen was also performed on other tissues of GSD IV mice at age 3 months. As shown in FIG. 39A, most hepatocytes were loaded with glycogen (fasted); the diaphragm has similar glycogen accumulation pattern as the gastrocnemius muscle; clusters of glycogen particles were occasionally found in the heart; PAS-positive granules were clearly present in the brain (cerebrum). Glycogen quantitation showed significantly lower glycogen contents in the STD-preps than in the Boil-preps for all the tissues (FIG. 39B). Glycogen content in the STD-prep was 28% of that in the Boil-prep for liver (fasted), and was 21% for heart, 8% for both brain and diaphragm (FIG. 39B).

Glycogen Quantitation in Fibroblasts from Patients with GSD II and IV

Figure 40:
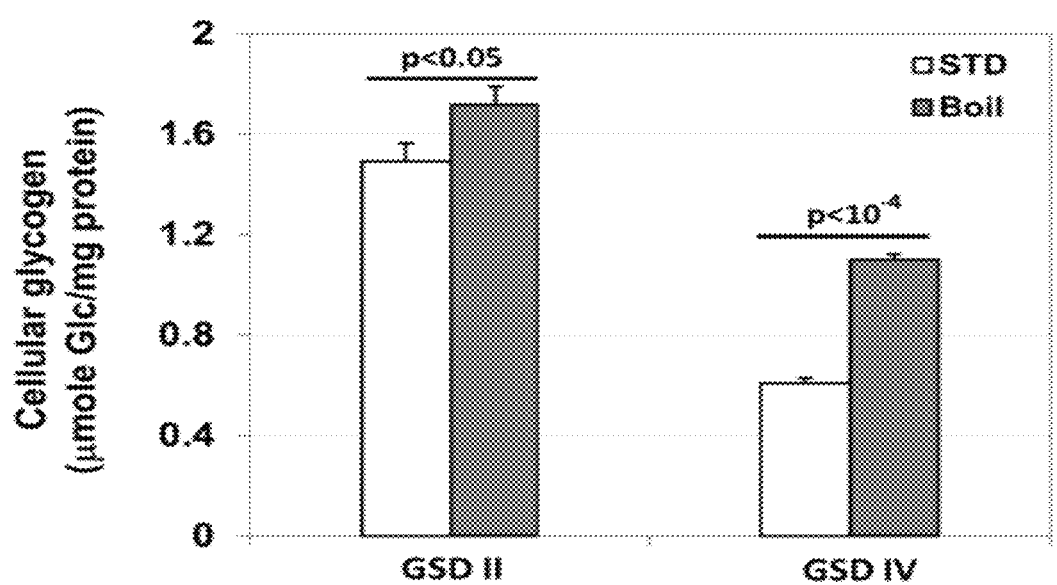
FIG. 40 illustrates a comparison of the STD-prep and the Boil-prep methods for quantitation of glycogen in cultured skin fibroblasts from a patient with GSD II and one with GSD IV. Average standard deviation of n=4 plates for each patient are shown.

In cultured human patient skin fibroblasts, the STD-prep of the GSD IV cells presented 50% less glycogen than the Boil-prep; the Boil-prep of GSD II cells presented 10% more glycogen than the STD-prep (FIG. 40).

Discussion

Mutations in the Gbe1 gene cause a complete or partial loss of GBE activity in GSD IV, which leads to an increase in the ratio of GS to GBE, a critical determinant of PB formation during the process of glycogen synthesis. The Y329S is the most common mutation found in Jewish families of Ashkenazi ancestry with adult onset GSD IV, also referred to as adult polyglucosan body disease. Recently we obtained a new mouse model of GSD IV (Gbe1ys/ys mice) carrying the knock-in Y329S mutation. The residual enzyme activity in the affected mice was approximately 24-30% of wild-type value in skeletal muscles, 10% in heart, and less than 5% in liver and brain (data not shown). PAS staining showed significant PB accumulation in all these tissues.

In a standard enzymatic method for glycogen quantitation, tissue homogenization in cold water or buffer followed by an immediate centrifugation has been a widely used procedure for its simplicity, sensitivity, and ability to analyze other metabolites and enzyme activities in the same homogenate. But this procedure is not suitable for GSD IV glycogen measurement due to the heavy loss of insoluble glycogen during sample preparation. In this study, we described a modified method that includes an extra boiling step prior to centrifugation of tissue homogenates to dissolve the insoluble glycogen in GSD IV. To determine the length of boiling time needed for complete glycogen dissolution, we quantified glycogen after boiling the homogenates (150-300 l) 3, 5, 10, and 15 minutes and saw no difference among all the time points (data not shown). This method is likely also applicable to Lafora disease, a related polyglucosan body disease caused by mutations in EPM2A or EPM2B, but this needs to be verified by experiments. Another more tedious and less sensitive method involving boiling tissue homogenate in KOH followed by ethanol-precipitation of glycogen prior to the amyloglucosidase digestion is also suitable for determining glycogen content in GSD IV, but this procedure requires larger size of tissues, which limits its clinical application.

This study provides an improved protocol for quantifying the insoluble glycogen in GSD IV without the need of glycogen isolation prior to the enzyme digestion. More importantly, the modified method allows determination of glycogen content in very small biopsy samples, which is extremely useful for clinical diagnostic laboratories. Validation with sufficient numbers of patient samples and normal controls will be necessary before applying this method to clinical diagnosis.

Example 11

Alglucosidase Alfa Enzyme Replacement Therapy as a Therapeutic Approach for GSD IV Methods: A short-term study was conducted to determine the minimum effective dose (MED) of rhGAA treatment with 3 dosages: 20 mg/kg (human equivalent dose, n=6), 40 mg/kg (n=9), and 100 mg/kg (n=8). Male GSD IV mice received weekly intravenous injections of rhGAA were conducted for 4 week starting at age of 10 weeks. A group of age-matched untreated mice (n=8) were used as controls. To prevent anaphylactic reactions, the animals were administered 25 mg/kg diphenhydramine (i.p.) 10-15 min prior to enzyme administration. All mice were sacrificed 48 hours after the last injection following overnight fasting. Fresh tissues were immediately frozen and stored at −80° C. until use for GAA activity and glycogen content analyses. Protein concentration was measured using BCA method.

Results: As shown in FIG. 41A, significant increase in GAA activity was observed in tissues of GAA-treated mice in a dose dependent manner. The greatest increase was found in liver, which had 29, 48, and 67 folds increase over untreated controls at the 3 doses from low to high, respectively. GAA activity in heart had a 1.7-fold increase in the 20 mg/kg dose group and 2.8-fold increase in the 40 mg/kg group. In quadriceps the increase in GAA activity was negligible at either dosage, while uptake by gastrocnemius was slightly more, with less than 1-fold increase of GAA activity in either treated group. Diaphragm had the highest GAA activity increase among the skeletal muscles tested, with increases of GAA activity similar to those in heart by the 40 mg/kg treatment. Enzyme uptake was less efficient in skeletal muscles as the GAA activity was increased by 1.6 folds at 100 mg/kg. Glycogen contents were significantly reduced only in liver of the 40 mg/kg (−21%) and 100 mg/kg (−25%) groups, not in any skeletal muscle (FIG. 41B). The low level of glycogen in heart of this GSD IV mouse model makes it difficult to draw a conclusion for this tissue (FIG. 41B). The 20 mg/kg GAA treatment failed to reduce glycogen in any tissue (FIG. 41B).

Consistent with reduced liver glycogen accumulation, the 40 mg/kg rhGAA treatment lowered liver/body weight ratio from 5.8±0.2% to 5.0±0.2% (p<0.05; FIG. 41C), and reduced plasma alanine aminotransferase (ALT) from 1029±87 U/L to 650±32 U/L (p<0.01; FIG. 41D) and aspartate aminotransferase (AST) from 1059±93 U/L to 849±50 U/L (p=0.074; FIG. 41E), indicating alleviation of hepatomegaly and liver damage.

Discussion: The low abundance of the M6PR has limited rhGAA uptake in skeletal muscle of GAA-KO mice. Adjunctive therapy with β2 agonists, such as clenbuterol, can improve the efficacy of rhGAA-based ERT and gene therapy in these mice by enhancing M6PR expression in skeletal muscle and the brain. Accordingly, an adjunctive therapy with clenbuterol, a selective β2 agonists, may increase M6PR expression, enhance rhGAA uptake, and improve treatment efficacy in GSD III and GSD IV mice. This result also has clinical applications for patients with GSD III and GSD IV.

Manose-6-phosphate receptor (M6PR) mediated ERT with rhGAA is an FDA approved therapy for Pompe disease. The pattern of rhGAA uptake by tissues of GSD IV mice (FIG. 41A) was similar to that observed in Pompe disease mice. The high GAA activity in liver and low activity in muscles following rhGAA treatment correlated well with the relative abundances of the M6PR in the two types of tissues. Even though the 20 mg/kg treatments led to significantly higher GAA activities in liver, the reduction of glycogen accumulation was not significant (FIG. 41B). This suggests that the insolubility of GSD IV glycogen makes it highly resistant to rhGAA digestion. Thus, it is not surprising to see the lack of effectiveness in skeletal muscles, which showed low uptake of rhGAA after treatment (FIG. 41A, FIG. 41B). Our interpretation for the reduction of liver glycogen in GSD IV mice by the high-does rhGAA treatment is that digestion of the insoluble GSD IV glycogen in lysosomes requires highly elevated rhGAA activity; clearance of lysosomal glycogen promotes glycogen trafficking into lysosomes, and thus reduces the overall glycogen accumulation. However, it is also possible that the excessive amount of rhGAA in lysosomes led to leakage of the enzyme into the cytoplasm and directly degraded the accumulated glycogen, even though the activity of GAA in the neutral pH environment is much lower than that in the acidic lysosome interior.

The typical clinical presentation of patients with hepatic GSD IV, such as hepatomegaly and elevation of liver enzymes caused by liver damage, was also observed in this GSD IV mouse model (FIGS. 41C, 41D, 41E). The biochemical correction of liver glycogen accumulation by the 40 mg/kg rhGAA treatment was accompanied by the attenuation of clinical liver symptoms, as indicated by the reduction of liver size (as determined by the liver/body weight ratio) and of liver enzymes in serum. Moreover, one apparent advantage of treating GSD IV with rhGAA is that, as patients express normal level of GAA, the therapeutic protein is unlikely to induce severe immune responses, which have been a major obstacle in treatment of Pompe disease. This data suggests that rhGAA could be a potential therapy for GSD IV and possibly other cytoplasmic GSDs.

Example 12

Investigation of Long-Term Treatment Efficacy with the Minimum Effective Dose (40 Mg/Kg) of rhGAA in GSD IV Mice, with or without the Adjunctive Therapy with Clenbuterol Clenbuterol, a β2 agonist, will be used in this study. Unlike in GAA-KO mice where glycogen is accumulated in lysosomes, treatment for GSD IV mice would require a longer course of treatment to demonstrate efficacy in reducing the cytoplasmic glycogen accumulation. All experiments will last for 3 months. There will be 4 groups, n=8-10 mice per group (Table 8):

TABLE 8

Experimental Design

| GROUP | NAME | TREATMENT |
|---|---|---|
| Group 1 | Mock-treatment group | weekly saline I.V. injection for 4 weeks |
| Group 2* | rhGAA only | weekly I.V. at MED |
| Group 3* | Clenbuterol treatment only | Clenbuterol administered ad libitum in drinking water at 30 μg/ml |
| Group 4* | Clenbuterol + rhGAA | rhGAA administered weekly I.V. at MED |

*: For each mouse, pretreatment with 15-25 mg/kg diphenhydramine by i.p. injection will be performed 10-15 min prior to rhGAA administration to prevent anaphylactic reactions.

All treatment will start at age of 3 months. Urine will be collected at ages of 3 and 6 months for testing urinary Hex4, a biomarker for Pompe disease, by stable isotope-dilution electrospray tandem mass spectrometry. Blood will be collected months from age 3 months to test anti-GAA antibody titers. Behavioral and muscle function will be tested at ages 3, 4.5, and 6 months, to assess reversal of neuromuscular involvement by treadmill, Rota-rod performance, wire-hang, and grip strength tests. All mice will be euthanized at age of 6 months for collection of 1) tissues including liver, heart, skeletal muscles, diaphragm, and the brain for histological and biochemical analysis.

Example 13

Generation and Characterization of a Mouse Model of GSD IIIA

Heterozygous AGL mutant mice (AglTm1a) carrying a mutant Agl allele (FIG. 31A) were purchased form The European Mouse Mutant Archive (EMMA). We have cross-bred this mouse line with a Cre deleter strain (CMV-Cre mice) to convert the mutant allele into an Agl-KO allele by deleting the Agl gene Exons 6-10 and the neo expression cassette (FIG. 31B). We have successfully crossed Agl+/− mice to generate homozygous Agl−/− (GSD III) mice. Once sufficient GSD III mice become available, we will characterize this model by analyzing these mice at different ages (1, 3, 6, and 9 months) for 1) tissue histology and glycogen contents; 2) muscle function performance by treadmill, Rota-rod performance, wire-hang, and grip strength tests; 3) urinary Hex4 levels.

Example 14

Alglucosidase Alfa Enzyme Replacement Therapy as a Therapeutic Approach for GSD III Methods: GSD III mice were used to test 3 dosages to determine the minimum effective dose (MED) of rhGAA treatment: 20 mg/kg (n=6), 40 mg/kg (n=5), and 100 mg/kg (n=7). Weekly intravenous injections of rhGAA were conducted for 4 week starting at age of 10 weeks. A group of age-matched untreated mice (n=8) were used as controls. To prevent anaphylactic reactions, the animals were administered 25 mg/kg diphenhydramine (i.p.) 10-15 min prior to enzyme administration. All mice were sacrificed 48 hours after the last injection following overnight fasting. Fresh tissues were immediately frozen and stored at −80° C. until use for GAA activity and glycogen content analyses. Protein concentration was measured using BCA method.

Results: GAA enzyme uptake was similar as seen in GSD IV mice: GAA activity in liver>heart>diaphragm>leg muscles (FIG. 42A).

Figure 43:
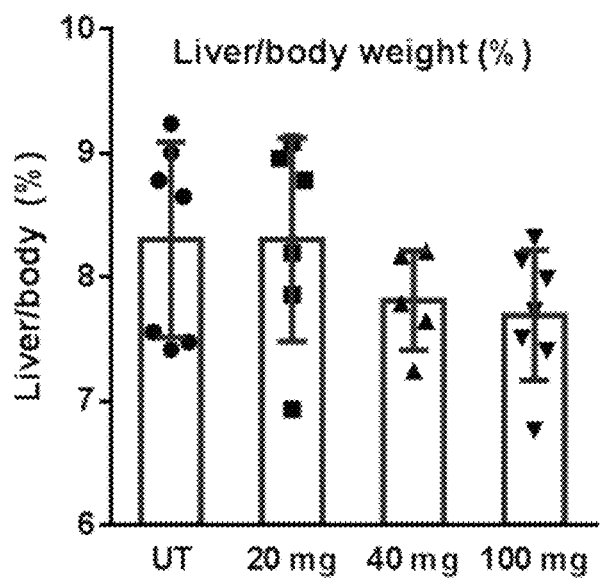
FIG. 43 illustrates the effect of rhGAA treatment on ratio of liver/body weight of GSD III mice upon weekly upon weekly intravenous administration of 20 mg/kg, 40 mg/kg, or 100 mg/kg rhGAA for 4 weeks.
Figure 44A:
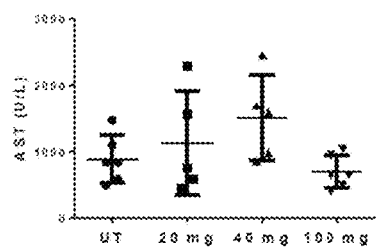
FIG. 44 illustrates the (FIG. 44A) plasma AST levels.
(FIG. 44B) plasma ALT levels.
(FIG. 44C) plasma ALP levels.
(FIG. 44D) plasma CK levels of GSD III mice upon weekly administration of 20 mg/kg, 40 mg/kg, or 100 mg/kg rhGAA for 4 weeks.
Figure 44B:
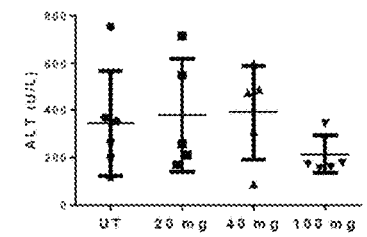
Figure 44C:
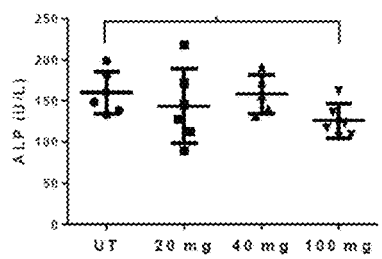
Figure 44D:
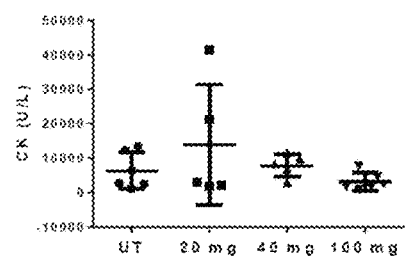

Both the 40 mg and 100 mg treatments significantly reduced glycogen contents to a similar level in liver of GSD III mice (FIG. 42B), accompanied by reduced ratio of liver/body weight (FIG. 43). In addition, both the 40-mg and 100-mg treatments significantly reduced glycogen contents in heart of GSD III mice (FIG. 42B). There was no significant change in glycogen content in skeletal muscles in the 40-mg and 100-mg treatment groups. The 20-mg treatment did not affect glycogen content in any tissues of the GSD III mice. There was also a reduction in plasma alanine aminotransferase (ALT), alkaline phosphatase (ALP), aspartate aminotransferase (AST), and creatine kinase (CK), indicating alleviation of hepatomegaly and liver damage. (FIG. 44). A long-term (up to 3 months) treatment efficacy with 40 mg/kg rhGAA will be evaluated in GSD III mice as outlined below.

Both GSD III and GSD IV mice generated significantly less anti-GAA antibodies than that reported in the GAA-KO mice, upon a short-term treatment (weekly rhGAA administration for 4 weeks) at a dose of 20 mg/kg, 40 mg/kg, or 100 mg/kg (data not shown). Both the 40 mg- and 100 mg-rhGAA treatment showed a similar impact on liver glycogen in each model, decreasing 24-25% in the GSD III (FIG. 42B) and 21-25% in the IV (FIG. 41B). In addition, both the 40 mg- and 100 mg- rhGAA treatment significantly reduced glycogen contents in the hearts of GSD III mice (FIG. 42B).

Example 15

Long Term Efficacy with rhGAA at the Minimum Effective Dose (40 Mg/Kg) of rhGAA Treatment in GSD III Mice Specific Aim: To investigate long-term treatment efficacy with rhGAA at a dose of 40 mg/kg in GSD III mice. Development of antibody response against human protein (rhGAA) in GSD III mice will reduce efficacy of Myozyme* (alglucosidase alfa) treatment. In this study Methotrexate (MTX) will be used to induce immune tolerance to rhGAA treatment in GSD III mice. There will be 2 groups, n=8 mice per group:

Group 1. Untreated group—no treatment controls;
Group 2. rhGAA treatment group*—weekly intravenous (I.V.) injection with rhGAA at 40 mg/kg for 12 weeks. Methotrexate at a dose of 10 mg/kg will be administered intraperitoneally (I.P.) at 0, 24 and 48 hour following the initial three weekly rhGAA administrations for each mouse, pretreatment with 15-25 mg/kg diphenhydramine by I.P. injection will be performed 10-15 min prior to rhGAA administration to prevent anaphylactic reactions.

All treatment will start at age of 8 weeks. Urine will be collected at ages of 8 and 20 weeks for testing urinary Hex4, a biomarker for Pompe disease, by stable isotope-dilution electrospray tandem mass spectrometry as previously described. Blood will be collected every 4 weeks to test anti-GAA antibody titers. All mice will be euthanized at age of 20 weeks. Weight of liver and whole body will be measured. Tissues including liver, heart, skeletal muscles, and diaphragm will be collected for histological and biochemical analysis. Plasma will be collected for analysis of liver enzyme activities.

Example 16

Evaluation of the Long-Term Treatment Efficacy with the Minimum Effective Dose (40 Mg/Kg) of rhGAA in GSD III Mice, with or without the Adjunctive Therapy with Clenbuterol Clenbuterol, a β2 agonist, will be used in this study. All experiments will last for 3 months. There will be 4 groups, n=8-10 mice per group (Table 9):

TABLE 9

Experimental Design

| GROUP | NAME | TREATMENT |
|---|---|---|
| Group 1 | Mock-treatment group | weekly saline I.V. injection for 4 weeks |
| Group 2* | rhGAA only | weekly I.V. at MED |
| Group 3* | Clenbuterol treatment only | Clenbuterol administered ad libitum in drinking water at 30 µg/ml |
| Group 4* | Clenbuterol + rhGAA | rhGAA administered weekly I.V. at MED |

*: For each mouse, pretreatment with 15-25 mg/kg diphenhydramine by i.p. injection, will be performed 10-15 min prior to rhGAA administration to prevent anaphylactic reactions.

All treatment will start at age of 3 months. Urine will be collected at ages of 3 and 6 months for testing urinary Hex4, a biomarker for Pompe disease, by stable isotope-dilution electrospray tandem mass spectrometry. Blood will be collected months from age 3 months to test anti-GAA antibody titers. Behavioral and muscle function will be tested at ages 3, 4.5, and 6 months, to assess reversal of neuromuscular involvement by treadmill, Rota-rod performance, wire-hang, and grip strength tests. All mice will be euthanized at age of 6 months for collection of tissues including liver, heart, skeletal muscles, diaphragm, and the brain for histological and biochemical analysis.

Example 17

Use of Alglucosidase Alfa Enzyme Replacement Therapy for Conditions Associated with PRKAG2 Mutations This example focuses on a patient initially diagnosed with Pompe disease and started on ERT with alglucosidase alfa, which improved his condition. However, over the course of the therapy, the patient began to develop inconsistent symptoms that led his physicians to question the diagnosis. Through further medical tests, the patient was diagnosed as a carrier of Pompe disease, in addition to carrying a PRKAG2 pathogenic gene mutation. This example further outlines the improvement that the patient showed while on ERT treatment, the decline to his condition when his infusions were discontinued due to his updated diagnosis, and the significant positive response when ERT was reinitiated. This example provides several key messages: 1) the importance of confirming the diagnosis of Pompe disease via gene sequencing before ERT initiation, 2) the potential of GAA as a treatment approach for cytoplasmic GSDs such as PRKAG2, and 3) the expansion of the PRKAG2 phenotype depicting the first report of a case with myopathy and no obvious cardiac involvement.

A male patient was born by caesarian section at 38 weeks gestation as a result of the nuchal cord being wrapped around his neck. At age 2½ months, the patient was noted to have hypotonia and generalized muscle weakness. He was are flexic and had feeding difficulties. At age 4 months, the patient began developing severe lower respiratory infections which led to frequent admissions to the hospital. Labs showed a mild increase in creatinine kinase (CK) at 197 IU/L (normal range: 38-174 IU/L) while other labs including ALT (15 IU/L; normal range: <45 IU/L) and AST (47 IU/L; normal range: 9-80 IU/L) were normal. Following numerous recurrent pneumonias, and the history of muscle weakness, the patient's physicians raised Pompe disease as a potential diagnosis. Blood GAA enzyme testing revealed a deficiency (4.81 units versus 18.66 units in the control sample). An ECHO revealed mild hypertrophy of the interventricular septum (IVS) and a normal sized left ventricular posterior wall (LVPW) with a normal left ventricular mass. The ECG showed that the ventricular forces were normal with a SR of 146/min and a PR interval of 0.10. Given the early findings of hypotonia and the low GAA enzyme activity, a diagnosis of non-classic infantile Pompe disease was made. The patient was initiated on ERT with alglucosdase alfa at a dose of 20 mg/kg every 2 weeks at age 11 months.

At age 11 months, the patient started ERT. He was belly crawling asymmetrically and was unable to achieve sitting from a prone or supine position. Due to weakness in his neck and trunk flexors, the patient consistently sat with his trunk completely collapsed in kyphotic position and his head propped up in capital extension in a chin poke position. This weakness also caused the patient to struggle with clearing secretions while coughing. Three months after the initiation of ERT, the patient's gross motor abilities as assessed by his physical therapist began improving and he achieved new milestones. He was able to crawl more efficiently, to achieve sitting independently from a prone or supine position, and to pull himself up into a standing posture without aid. The patient's level of endurance also improved which allowed him to be more active. At age 29 months, the patient was able to walk independently with an age appropriate gait pattern and to climb small steps as well as jump off them without support. He was also able to transition independently into and out of any position, which helped him participate more fully in activities appropriate for his age.

Interestingly at age 13 months, one month after the start of ERT, the patient began to have febrile and non-febrile seizures. An EEG completed at age 14 months revealed epileptic activity. He exhibited tremors of the head and extremities at intermittent intervals with the tremors growing worse upon awakening and while in the motion of reaching. The patient was evaluated by a neurologist and was noted to have an intention tremor, titubation, ataxia, and very mild hypotonia. At age 4 years, he developed complex partial seizures compounded by a 2-3 day period where he was completely floppy and weak, often unable to lift his head off the pillow. Based on these events, the neurologist diagnosed the patient with a complex genetic epilepsy syndrome. As the patient's medical history was somewhat unusual for one with infantile Pompe disease, further evaluation was initiated to determine if he had another diagnosis in addition to Pompe disease to explain these findings or if the initial diagnosis was incorrect. At age 2.5 years (30 months) GAA enzyme activity was done on skin fibroblasts, which was suggestive of a carrier status (50.7 nmol/h/mg with a control range of 45-180 nmol/h/mg and a patient range of 0-20 nmol/h/mg). Sequencing of the GAA gene found the patient to be heterozygous for the common splice site mutation c.-32-13 T/G, a pathogenic mutation among patients with the adult form of Pompe disease. No other mutation was identified; these findings were consistent with carrier status. ERT was discontinued for the patient at age 33 months after 22 months on ERT.

Figure 46:
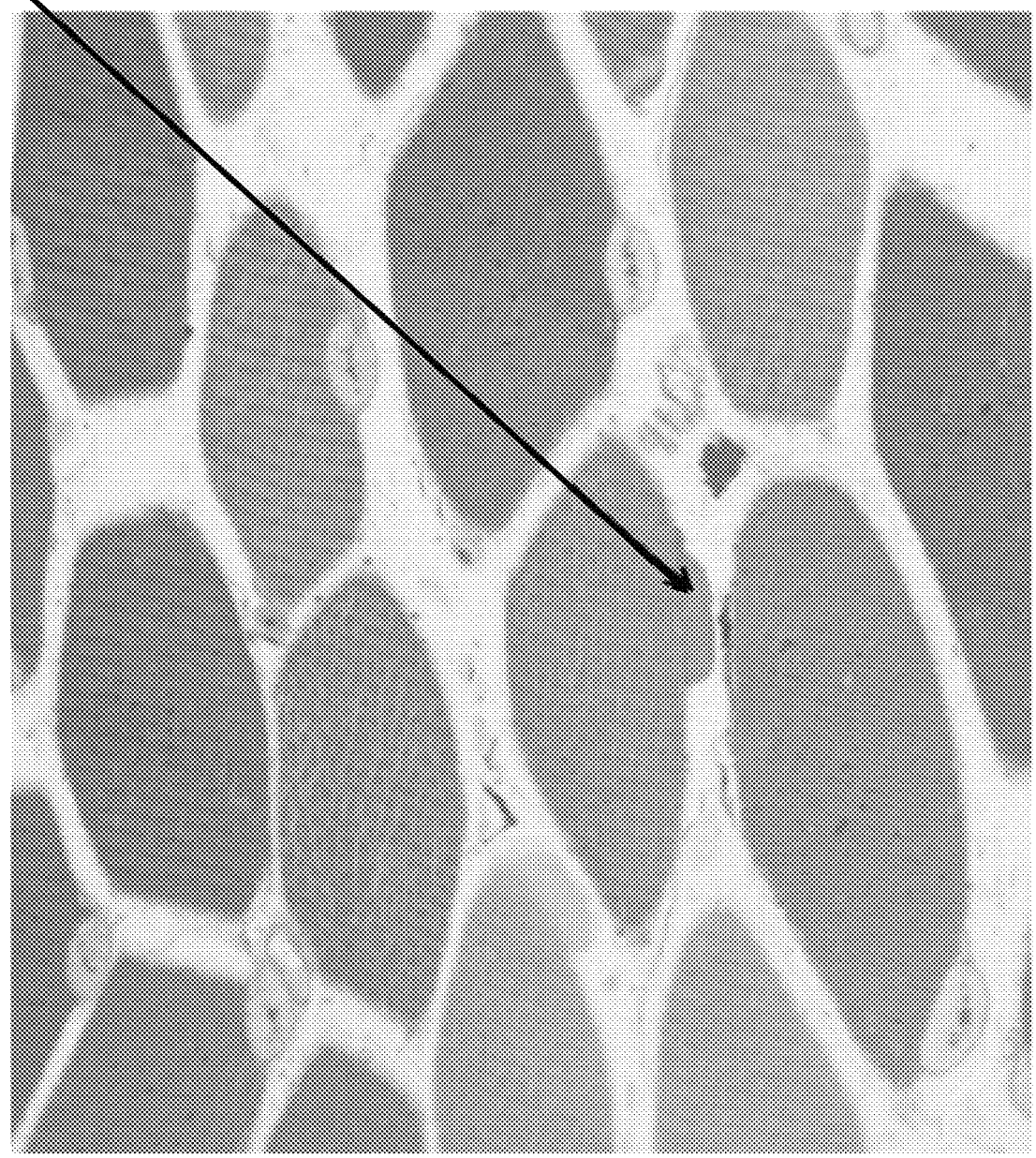
FIG. 46 illustrates a high resolution light microscopy of quadriceps muscle biopsy from a patient with PRKAG2 deficiency at age 44 months. Patient was not on ERT at the time of biopsy (off ERT for 11 months). One-micron semi-thin epon sections were stained with Richardsons/PAS stain combination. PAS positive blebs 1 (identified at the end of the arrow), are present at the periphery of some cells, suggestive of glycogen accumulation.
Figure 47:
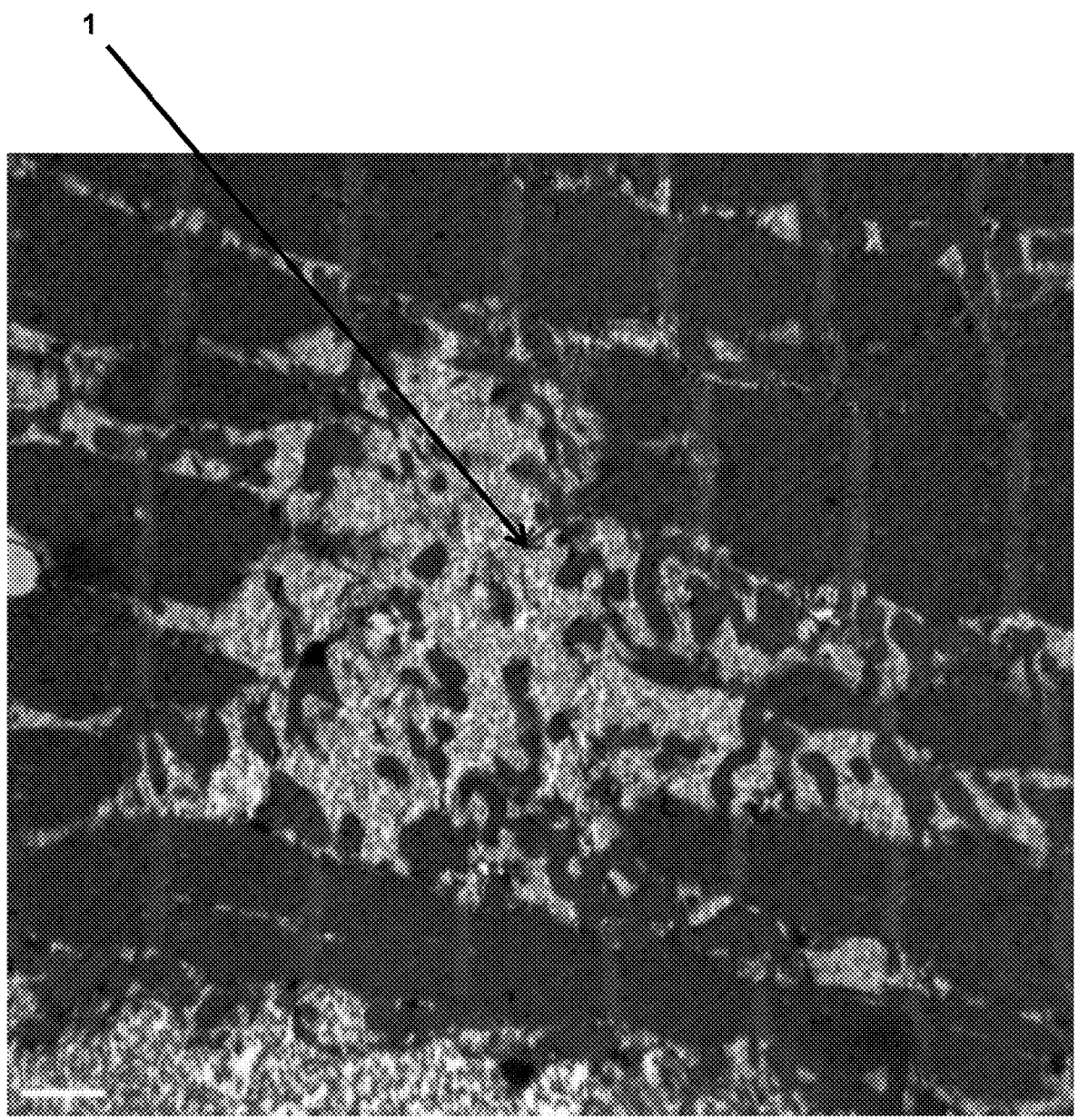
FIG. 47 illustrates electron microscopy of quadriceps muscle biopsy from a patient with PRKAG2 deficiency at age 44 months. Patient was not on ERT at the time of biopsy (off ERT for 11 months). The myofibrillar structure of the myocytes was largely intact in most fields. There were isolated foci of frayed and degenerated myofibrils interrupted by small pools of cytoplasmic glycogen 1 (identified at the end of the arrow).

A quadriceps muscle biopsy was obtained at age 44 months showed cytoplasmic glycogen, suggestive of a non-lysosomal glycogen storage disease (FIGS. 46 and 47). Muscle acid alpha glucosidase activity tested in the low normal range suggestive of carrier status; phosphorylase and phosphorylase kinase activities measured in normal ranges. Further work up included a mitochondrial myopathy enzyme panel and a mitochondrial respiratory chain panel which were normal and a glycogen storage disease sequencing panel (GCTS Pathology, London, UK) which showed that the patient had a pathogenic mutation in PRKAG2, c.298G>A p. (Gly100Ser), which had been reported previously in cases of PRKAG2 (Table 10 below). As PRKAG2 is inherited in an autosomal dominant manner, the family history was taken again with a focus on the patient's maternal cousin once removed who suddenly died at age 29 due to a cardiac event. The hospital records indicated that the EKG taken at the day of his death indicated a normal sinus rhythm with normal repolarization, normal PR and QTc with no Brugada pattern. There was mild ST segment depression in the inferior leads.

ing sessions, tended to lie on the floor or on the equipment with significant lack of energy. In addition, there was a decline in his speech and communication; the patient often mumbled and refused to answer his therapist when prompted.

Due to the patient's regressions, past clinical benefit, family request, support from his physicians, and past literature revealing a potential role of alglucosidase alpha in individuals with a cytoplasmic GSD, the patient received IV alglucosidase alfa treatment for 6 months on a trial basis with close follow up after the initiation of therapy (started at age 47 months). Baseline assessments were done which included tests for AST (44 IU/L; normal range: <45 IU/L), ALT (20 IU/L; normal range: 9-80 IU/L), along with PT measures looking at muscle strength and function measures. After five months of ERT, the patient has shown significant improvement according to his neurological, occupational therapy, and physical therapy reports. The patient no longer exhibited myopathic faces or ptosis, his tenting of his upper lip had improved, and he had more facial expression than before. Upon examination, the patient has developed more defined calf muscles, along with an improvement of his strength and power. According to his neurologist (PH), in addition to improvement in strength, the patient's seizures appear to be better controlled since the reinitiation of ERT with alglucosidase alfa; however, this is difficult to understand given that ERT does not cross the blood brain barrier. He has grown physically stronger and has not had episodes in which he lacks energy for consecutive days, becomes completely floppy, and is unable to hold his head up properly following a seizure.

TABLE 10

Literature Review of PRKAG2 Cases with Symptoms and Genotype

| Reference | Number of Cases | Ages | Resolution | Symptoms Shown | Genotype |
|---|---|---|---|---|---|
| Zhang et al. (2013) | 9 cases | 16-49 years | 3 deceased | Wolff-Parkinson-White syndrome conduction system disease, and/or hypertrophic cardiomyopathy | PRKAG2 G100S missense mutation* |
| Laforet et al. (2006) | 1 case | 38 years | Not deceased | Sinusal bradycardia, high degree of ventricular block, hypertrophic cardiomyopathy | PRKAG2 S548P missense mutation |
| Burwinkel et al. (2005) | 1 case | 34 days | deceased | Fetal bradycardia, preventricular hypertrophy, cardiomegaly, severe hypertrophic cardiomyopathy | PRKAG2 Het R531Qh mutation |
| Buhrer et al. (2003) | 1 case | 21 days | deceased | Bradycardia, atrial and biventricular hypertrophy, pericardial effusion | PRKAG2 Het R531Qh mutation |
| Arad et al. (2002) | 6 cases | 19-55 years | unknown | Cardiac hypertrophy, ventricular pre-excitation (Wolff-Parkinson-White Syndrome), progressive dysfunction of the conduction system | PRKAG2 R302G (4 cases), PRKAG2 T400N (1 case), PRKAG2 N488I (1 case) missense mutation |
| Gollob et al (2001) | 4 cases | 8-41 years | unknown | Wolff-Parkinson-White Syndrome, ventricular preexcitation, early onset of atrial fibrillation and conduction disease | PRKAG2 R531G missense mutation |
| Relgado et al. (1999) | 2 cases | Birth-2 months | deceased | Cardiomegaly, bradycardia, cardiorespiratory problems | PRKAG2 Het R531Qh mutation |
| Zhang et al. (2014) | 1 Zebrafish cases | — | — | Thicker heart wall, increased glycogen storage in heart wall | PRKAG2 G100S missense mutation* |

*denotes same mutation as patient in case report (G1000S)

During the period of 14 months without ERT (age 33 months to age 47 months), the patient was followed closely and clinical decline was noted. The physical therapist observed that the patient was struggling to participate in physical therapy (PT) sessions, which had been easily managed previously while on ERT. He was falling frequently. The patient, who had previously been very interactive during His PT reports indicated that he was learning new motor skills or improving his current skills, which were now well within the average for motor tasks (Table 11 below). The patient's physical therapy reports from before ERT reinitiation and post-5 months have recorded significant improvements based on assessment with Movement ABC (MABC) which provides quantitative and qualitative data about a child's performance of age-appropriate tasks within 3 subsections: 1) Manual Dexterity, 2) Ball Skills, and 3) Static and Dynamic Balance. At baseline, according to the MABC assessment, the patient achieved a Total Test Score of 68 ranking him in the 25$^{th}$ percentile. Five months after reinitiation of ERT, the patient achieved a Total Test Score of 73 on his MABC assessment, ranking him in the 37$^{th}$ percentile. A minimal detectable change (MDC) for the MABC has been reported as 1.21 points, representing a true change in motor function. The results in this child show an increase of 5 points over 5 months, which is greater than the minimal important difference (MID) of the MABC, which has been reported as a change of 2.5 points shown over 6 months. Overall, according to his occupational therapist, the patient presented with less fatigue on reassessment and was able to complete the full assessment, which he had initially been unable to accomplish. After five months of ERT, he also demonstrated an improvement in his visual motor, fine motor, and gross motor skills as measured by the Miller Function and Participation Scales (M-FUN) when comparing his initial assessment scores taken in his first month of ERT reinitiation to his reassessment scores five months later as shown in Table 11I below.

TABLE 11

Motor Improvements

Movement ABC (Manual Dexterity, Ball Skills, & Static and Dynamic Balance)
Initial Assessment (Pre-ERT)   Re-assessment (5 months on ERT

| | Initial Assessment (Pre-ERT) | Re-assessment (5 months on ERT) |
|---|---|---|
| Total Score | 68 | 73 |
| Percentile | 25$^{th}$ percentile | 37$^{th}$ percentile |
| | Increase of 5 points with percentile increase of 12, minimal detectable change (MDC) = 0.28 points, minimal important difference (MID) = 2.36 to 2.50.) | |

Miller Function and Participation Scales (M-FUN)

| Visual Visual Motor Score* | Initial Assessment (Pre-ERT) | Reassessment (5 months post ERT) |
|---|---|---|
| Scaled Score | 6 (considered mild or borderline delay, >1 standard deviation below the mean, but <2 standard deviations below the mean) | 9 (considered "average" or within 1 standard deviation of the mean) |
| Progress Score | 374 | 496 |
| Assessment Notes | Patient's scaled scores show a visual motor improvement from mild/borderline delay to the average range for his age. His progress score is indicative of learning new motor skills or improving his current skills. | |
| Fine Motor Score* | | |
| Scaled Score | 3 (considered "very low or severe" delay, >2 standard deviations below the mean) | 5 (considered mild/borderline delay, >1 standard deviation below the mean, but <2 standard deviations below the mean) |
| Progress Score | 292 | 394 |
| Assessment Notes | Patient's scaled scores show a fine motor improvement from very low/severe fine motor delay of >2 standard deviations below the mean to mild/borderline fine motor delay >1 but <2 standard deviations below the mean. | |
| | Patient fatigued and required maximal encouragement to continue testing. As a result, he struggled to persevere and to recruit sufficient energy for stability and strength tasks. | Patient was eager to participate. He was able to participate without excessive encouragement on the fine motor tasks. |
| Gross Motor Score* | | |
| Scaled Score | 3 (considered very low/severe delay, >2 standard deviations below the mean) | 3 (considered very low/severe delay, >2 standard deviations below the mean) |
| Progress Score | 288 | 407 |
| Reassessment Notes | Patient's scaled scores indicate that his rank relative to age level peers has not changed and remains very low/severely delayed but his progress score indicates that he is gaining new motor skills and is improving in his current skills (could not hop but now can, could not adequately participate in gross motor tasks during the initial assessment but on reassessment had sufficient energy to attempt many of the tasks). | |
| Overall Assessment | Patient presented with less fatigue on reassessment and was able to complete the full assessment which he was not able to on initial assessment. He demonstrated an improvement in his visual motor and fine motor skills, and although his scaled score on a gross motor level remained the same, he was also progressing on gross motor level. | |

The overall assessment findings at five months indicated that he presented with less fatigue and was able to complete the full assessment which he was not able to on initial assessment. These findings have led the patient's physicians to recommend the continuation of the infusions to treat his alglucosidase alfa responsive cytoplasmic GSD caused by a mutation in PRKAG2 gene. The patient continues on ERT at the age of 6 years (about 2 years on ERT). Per parental report, he continues to have gross motor gains but some fine motor fatigue with hand writing for longer periods of time and hypotonia.

Due to similar symptomatic phenotypes, rare PRKAG2 cases can be misdiagnosed with infantile Pompe disease. PRKAG2 should be in the differential diagnosis of cases with cardiomyopathy. Interestingly, the patient only exhibited mild cardiac hypertrophy, not typical of patients diagnosed with PRKAG2 as shown in Table 10. He did have a family member die of a sudden cardiac event, and based on current literature, there is a broader cardiac clinical spectrum of this disorder beyond cardiac involvement which includes myalgia, myopathy and seizures. The patient was diagnosed with a pathogenic mutation in PRKAG2, Gly100Ser. Other patients exhibiting the same PRKAG2 Gly100Ser mutation have been reported to have a variable cardiac presentation including ventricular pre-excitation, progressive conduction system disease, and ventricular hypertrophy. The family in the Zhang et al (2013) paper did not have muscle symptoms reported as documented in our patient. However, muscle symptoms have been reported in patients with PRKAG2; 7 of 40 patients (15%) with an N488I mutation in PRKAG2 had myalgia/myopathy. Four patients from this cohort of 45 also had epilepsy (generalized tonic-clonic seizures), poorly controlled with medications, including 3 who also had myalgia. The present example serves to add to the phenotypic spectrum of PRKAG2 as well as highlight the importance of confirming a diagnosis of Pompe disease by more than one method. The blood based assay to diagnose Pompe disease should be performed in a lab with experience because if not done correctly, the test can result in an incorrect initial diagnosis, as noted in this case. PRKAG2 syndrome should be considered in differential diagnosis of Pompe disease. There have been two additional cases of PRKAG2 syndrome where the patients were initially clinically misdiagnosed with Pompe disease due to significant hypertrophic cardiomyopathy at presentation in one case and muscle weakness in the other (PSK personal communication).

As evidenced by the example depicting significant musculoskeletal improvements with alglucosidase alfa, a subsequent decline when ERT was withdrawn, and then improvement following reinitiation of ERT, there seem to be implications of the effectiveness of alglucosidase alfa therapy for PRKAG2 deficiency. In the past, the diagnosis of Pompe disease was confirmed using GAA enzyme measurements in cultured fibroblasts or muscle cells. Enzyme measurement using acarbose, an inhibitor of alpha-glucosidase, can greatly improve the sensitivity and specificity of Pompe disease diagnosis in blood and has now been adapted in many labs as a rapid way to diagnose Pompe disease; however, without the addition of acarbose, there can be false positive results. Thus, the test needs to be done in labs with experience and expertise. It is important to broaden the diagnostic measures to include additional tests outside of enzyme testing in dried blood spots (DBS) such as gene sequencing and measurement of GAA activity in other tissue such as skin and muscle prior to initiation of ERT.

Among the GSDs, Pompe disease is the only exception with glycogen accumulation in lysosomes (lysosomal GSD) whereas all others have glycogen storage in the cytoplasm (cytoplasmic GSD). Furthermore, the use of ERT with alglucosidase alfa depends upon the mannose 6-phosphate receptor mediated enzyme uptake into lysosomes, which has been effective in reducing lysosomal glycogen storage in Pompe disease. Our group has demonstrated that ERT significantly reduced glycogen levels in the cultured primary myoblasts from skeletal muscle biopsies of patients with GSD III, a cytoplasmic GSD caused by the deficiency of glycogen debranching enzyme that leads to accumulation of abnormally structured cytoplasmic glycogen in liver and muscle. It is believed that administration of recombinant human acid alfa glucosidase enhanced lysosomal glycogen depletion, facilitated glycogen transport from the cytoplasm into lysosomes, and ultimately reduced cytoplasmic glycogen accumulation in the GSD III patient cells. As evidenced by the outcomes of this example depicting significant musculoskeletal improvements with alglucosidase alfa, a subsequent decline when ERT was withdrawn, and then improvement following reinitiation of ERT, there seem to be implications of the effectiveness of alglucosidase alfa therapy for PRKAG2 syndrome. It is possible that physical therapy and endurance exercise could be adding to the improvement in strength in our patient. However, this patient continued PT throughout his clinical course, even when ERT was discontinued with no clinical impact. It is also possible that being a carrier for Pompe disease which resulted in a decrease in residual endogenous GAA activity, could have resulted in an even greater clinical benefit from the administration of recombinant human GAA (ERT) in this case. However, in the preclinical work with GSD III, even with normal GAA activity, a benefit in cytoplasmic glycogen clearance was noted. Thus, the benefit is expected, even if the patient was not a carrier for Pompe disease.

Example 18

PRKAG2 Mutations Presenting in Infancy—a Possible Therapeutic Approach Using Alglucosidase Alfa Enzyme Replacement Therapy Background: PRKAG2 encodes the 72 subunit of AMP-activated protein kinase (AMPK) which is an important regulator of cardiac metabolism. Mutations in PRKAG2 cause a cardiac syndrome comprised of ventricular hypertrophy, preexcitation, and progressive conduction system disease. Significant variability exists in the presentation and outcomes of patients with PRKAG2 mutations. The features often resemble the cardiac manifestations of Pompe disease.

Methods: Here, we add three cases to the five previously described where patients with PRKAG2 mutations presented with symptoms in infancy. In all three of our cases, Pompe disease was the initial suspected diagnosis, with two patients going on to receive enzyme replacement therapy (ERT). However, Pompe disease was eventually ruled out, and a disease causing PRKAG2 mutation was identified subsequently in each case. In one case, ERT was stopped after the PRKAG2 mutation was identified. As the motor deficits progressed on standardized measures, the treating physicians restarted ERT, and a clinical benefit was noted.

Discussion: We highlight the potential for PRKAG2 mutations to mimic Pompe disease in infancy and the need for confirmatory testing via sequencing when diagnosing Pompe disease. Also, we outline the benefit a patient showed while on ERT treatment, the decline in his condition when the infusions were discontinued, and the significant positive response when ERT was reinitiated. This further supports the role of ERT in clearing cytoplasmic glycogen.

Although the present invention has been described in considerable detail with reference to certain preferred embodiments thereof, other versions are possible. Therefore the spirit and scope of the appended claims should not be limited to the description and the preferred versions contained within this specification.

The invention claimed is:

1. A method of reducing the level of cytoplasmic glycogen in a subject having a cytoplasmic glycogen storage disease, the method comprising:
administering weekly to the subject a first therapeutically effective amount of about 40 mg/kg to about 100 mg/kg acid alpha-glucosidase until a desired response is obtained, wherein the desired response is selected from the group consisting of improved hypoglycemia, reduced growth retardation, reduced hepatomegaly, improved hepatic function, improved liver function, reduced liver inflammation, reduced hepatomegaly, improved cardiac status, reduced cardiomyopathy, reduced myopathy, reduced glycogen content, and a combination thereof; and
administering at a regular interval to the subject a second therapeutically effective dose of about 20 mg/kg to about 80 mg/kg acid alpha-glucosidase,
wherein the cytoplasmic glycogen storage disease is glycogen storage disease type I (GSD I), glycogen storage disease Ill (GSD III), glycogen storage disease IV (GSD IV), glycogen storage disease V (GSD V), glycogen storage disease VI (GSD VI), glycogen storage disease VII (GSD VII), glycogen storage disease IX (GSD IX), glycogen storage disease XI (GSD XI), glycogen storage disease XII (GSD XII), glycogen storage disease XIII (GSD XIII), glycogen storage disease XIV (GSD XIV), Danon disease, Lafora disease, or a condition associated with a protein kinase gamma subunit 2-deficiency (PRKAG2).

2. The method of claim 1, wherein the regular interval is bimonthly, monthly, biweekly, weekly, twice weekly, daily, twice a day, three times a day, or more than three times a day.

3. The method of claim 1, further comprising administering to the subject an immune modulator.

4. The method of claim 3, wherein the immune modulator is methotrexate.

5. The method of claim 3, wherein the immune modulator is administered prior to administering the first therapeutically effective amount of acid alpha-glucosidase, the second therapeutically effective amount of acid alpha-glucosidase, or both.

6. The method of claim 1, wherein the condition associated with PRKAG2 deficiency is due to a PRKAG2 Het R531Qh mutation, a PRKAG2 R302G mutation, a PRKAG2 T400N mutation, a PRKAG2 N4881 missense mutation, a PRKAG2 R531G missense mutation, a PRKAG2G100S missense mutation, or a combination thereof.

7. The method of claim 1, wherein the condition associated with PRKAG2 deficiency comprises hypotonia, cardiomyopathy, cardiac hypertrophy, myopathy, cytoplasmic glycogen accumulation, ventricular hypertrophy, severe infantile hypertrophic cardiomyopathy, heart rhythm disturbances, increased left ventricular wall thickness, ventricular pre-excitation, or a combination thereof.

8. The method of claim 1, further comprising administering to the subject gene therapy.

9. The method of claim 1, wherein the acid alpha-glucosidase is selected from the group consisting of a GAA, a rhGAA, a neo-rhGAA, a reveglucosidase alpha, a rhGAA having a M6P content higher than naturally occurring GAA, a functional equivalent thereof, and a combination thereof.

10. The method of claim 1, wherein the rhGAA comprises alglucosidase alfa.

11. The method of claim 1, further comprising administering to the subject a therapeutic agent.

12. The method of claim 11, wherein the therapeutic agent is administered prior to, concurrently with, or shortly thereafter the first therapeutically effective amount of acid alpha-glucosidase.

13. The method of claim 11, wherein the therapeutic agent is administered prior to, concurrently with, or shortly thereafter the second therapeutically effective dose of acid alpha-glucosidase, or a combination thereof.

14. A method of reducing the level of cytoplasmic glycogen in a subject having a glycogen storage disease, comprising:
administering weekly to a subject a first therapeutically effective amount of acid alpha-glucosidase until a desired response is obtained,
wherein the desired response is selected from the group consisting of improved hypoglycemia, reduced growth retardation, reduced hepatomegaly, improved hepatic function, improved liver function, reduced liver inflammation, reduced hepatomegaly, improved cardiac status, reduced cardiomyopathy, reduced myopathy, reduced glycogen content, and a combination thereof,
wherein the first therapeutically effective dose is about 40 mg/kg to about 100 mg/kg, and administering at a regular interval to the subject a second therapeutically effective dose of acid alpha-glucosidase, wherein the second therapeutically effective dose is about 20 mg/kg to about 80 mg/kg, and wherein the glycogen storage disease is glycogen storage disease I (GSD I), glycogen storage disease III (GSD III), or glycogen storage disease IV (GSD IV).

* * * * *

UNITED STATES PATENT AND TRADEMARK OFFICE
CERTIFICATE OF CORRECTION

PATENT NO. : 12,036,190 B2
APPLICATION NO. : 17/408397
DATED : July 16, 2024
INVENTOR(S) : Priya Kishnani, Baodong Sun and Dwight D. Koeberl Page 1 of 1

It is certified that error appears in the above-identified patent and that said Letters Patent is hereby corrected as shown below:

In the Claims

In Claim 1, Column 69, Line 16, after "acid alpha-glucosidase" insert -- (GAA) --.

In Claim 9, Column 70, Line 16, delete "rhGAA" and insert -- recombinant human GAA (rhGAA) --.

In Claim 9, Column 70, Line 17, delete "M6P" and insert -- mannose-6-phosphate (M6P) --.

In Claim 10, Column 70, Line 19, delete "claim 1" and insert -- claim 9 --.

Signed and Sealed this
Eleventh Day of February, 2025

Coke Morgan Stewart
*Acting Director of the United States Patent and Trademark Office*